(12) United States Patent
Mattern

(10) Patent No.: US 11,903,951 B2
(45) Date of Patent: Feb. 20, 2024

(54) NASAL PHARMACEUTICAL COMPOSITIONS WITH A POROUS EXCIPIENT

(71) Applicant: M et P Pharma AG, Emmetten (CH)

(72) Inventor: Claudia Mattern, Emmetten (CH)

(73) Assignee: M et P Pharma AG, Emmetten (CH)

( * ) Notice: Subject to any disclaimer, the term of this patent is extended or adjusted under 35 U.S.C. 154(b) by 0 days.

(21) Appl. No.: 15/612,454

(22) Filed: Jun. 2, 2017

(65) Prior Publication Data

US 2018/0008615 A1 Jan. 11, 2018

Related U.S. Application Data

(60) Provisional application No. 62/345,369, filed on Jun. 3, 2016.

(51) Int. Cl.

| | | |
|---|---|---|
| *A61K 31/56* | (2006.01) | |
| *A61K 47/44* | (2017.01) | |
| *A61K 31/57* | (2006.01) | |
| *A61K 9/06* | (2006.01) | |
| *A61K 47/02* | (2006.01) | |
| *A61K 31/568* | (2006.01) | |
| *A61K 31/4458* | (2006.01) | |
| *A61K 31/381* | (2006.01) | |
| *A61K 31/165* | (2006.01) | |
| *A61K 31/496* | (2006.01) | |
| *A61K 31/13* | (2006.01) | |
| *A61K 47/69* | (2017.01) | |
| *A61K 9/00* | (2006.01) | |
| *A61K 9/16* | (2006.01) | |
| *A61K 9/50* | (2006.01) | |

(52) U.S. Cl.
CPC .......... *A61K 31/56* (2013.01); *A61K 9/0043* (2013.01); *A61K 9/06* (2013.01); *A61K 31/13* (2013.01); *A61K 31/165* (2013.01); *A61K 31/381* (2013.01); *A61K 31/4458* (2013.01); *A61K 31/496* (2013.01); *A61K 31/568* (2013.01); *A61K 31/57* (2013.01); *A61K 47/02* (2013.01); *A61K 47/44* (2013.01); *A61K 47/6923* (2017.08); *A61K 9/1611* (2013.01); *A61K 9/1635* (2013.01); *A61K 9/5015* (2013.01)

(58) Field of Classification Search
CPC ............................. A61K 31/56; A61K 47/6923
See application file for complete search history.

(56) References Cited

U.S. PATENT DOCUMENTS

| | | | |
|---|---|---|---|
| 5,002,597 A | 3/1991 | Gielow et al. | |
| 7,001,615 B1 | 2/2006 | Singh et al. | |
| 8,258,137 B2 * | 9/2012 | Augustijns | A61K 31/41 424/401 |
| 8,574,622 B2 * | 11/2013 | Mattern | A61P 11/02 424/450 |
| 8,609,043 B2 | 12/2013 | Mattern | |
| 8,784,869 B2 | 7/2014 | Mattern | |
| 8,784,882 B2 | 7/2014 | Mattern | |
| 8,877,230 B2 | 11/2014 | Mattern | |
| 9,186,320 B2 | 11/2015 | Mattern | |
| 9,238,072 B2 | 1/2016 | Mattern | |
| 9,579,280 B2 | 2/2017 | Mattern | |
| 2005/0100564 A1 | 5/2005 | Mattern | |
| 2006/0140820 A1 | 6/2006 | Mattern | |
| 2006/0154069 A1 * | 7/2006 | Lin | A61K 9/0019 428/402 |
| 2007/0149454 A1 | 6/2007 | Mattern | |
| 2009/0227550 A1 * | 9/2009 | Mattern | A61K 9/0043 514/171 |
| 2010/0311707 A1 | 12/2010 | Mattern | |
| 2011/0237562 A1 | 9/2011 | Mattern | |
| 2011/0244002 A1 * | 10/2011 | Shen | A61K 9/143 424/400 |
| 2012/0005987 A1 | 1/2012 | Mattern | |
| 2012/0277202 A1 | 11/2012 | Mattern | |
| 2013/0040922 A1 | 2/2013 | Kreppner et al. | |
| 2014/0363509 A1 * | 12/2014 | Mortera | A61K 31/4174 424/489 |
| 2015/0290217 A1 * | 10/2015 | Kreppner | A61K 31/568 514/178 |
| 2015/0297733 A1 * | 10/2015 | Oberegger | A61K 47/10 514/178 |
| 2016/0089347 A1 | 3/2016 | Mattern | |

(Continued)

FOREIGN PATENT DOCUMENTS

| | | |
|---|---|---|
| JP | 2014-513147 A | 5/2014 |
| JP | 2014-515038 A | 6/2014 |

(Continued)

OTHER PUBLICATIONS

Martinez-Carmona, et al., Smart Mesoporous Nanomaterials for Antitumor Therapy, *Nanomaterials*, vol. 5, pp. 1906-1937 (Nov. 2015).

Lai, et al., "A Mesoporous Silica Nanosphere-Based Carrier System with Chemically Removable CdS Nanoparticle Caps for Stimuli-Responsive Controlled Release of Neurotransmitters and Drug Molecules," *j. Am. Soc. Chem.*, vol. 125, No. 15, pp. 4451-4459 (Mar. 2003).

Sun, Mesoporous silica nanoparticles for applications in drug delivery and catalysis, a dissertation submitted to the graduate faculty in partial fulfillment of the requirements for the degree of Doctor of Philosophy, 118 pages (2012).

(Continued)

*Primary Examiner* — Robert A Wax
*Assistant Examiner* — William Craigo
(74) *Attorney, Agent, or Firm* — Foley & Lardner LLP

(57) ABSTRACT

Described herein are nasal pharmaceutical compositions comprising a porous excipient and an active agent, wherein the active agent is loaded onto a surface of the porous excipient located inside pores of the porous excipient, and wherein the composition is adapted for nasal administration. Also described herein are methods of making and using nasal pharmaceutical compositions.

19 Claims, 51 Drawing Sheets

(56) References Cited

U.S. PATENT DOCUMENTS

2017/0189414 A1 7/2017 Mattern
2018/0296472 A1 10/2018 Mattern

FOREIGN PATENT DOCUMENTS

| WO | WO 97/44013 | 11/1997 | |
|---|---|---|---|
| WO | WO 98/30245 | 7/1998 | |
| WO | WO-02/051379 A2 | 7/2002 | |
| WO | WO 2007/041079 A2 | 4/2007 | |
| WO | WO 2010/039560 A2 | 4/2010 | |
| WO | WO-2012/156820 A1 | 11/2012 | |
| WO | WO-2012/156821 A1 | 11/2012 | |
| WO | WO-2012/156822 A1 | 11/2012 | |
| WO | WO 2014/066856 A1 | 5/2014 | |
| WO | WO 2015/066717 A1 | 5/2015 | |
| WO | WO 2016/041992 A1 | 3/2016 | |
| WO | WO-2016041992 A1 * | 3/2016 | ........... A61K 9/0048 |
| WO | WO-2017/023162 A1 | 2/2017 | |
| WO | WO-2017/042709 A1 | 3/2017 | |

OTHER PUBLICATIONS

Vallet-Regi, et al., "Biomedical Applications of Mesoporous Ceramics: Drug Delivery, Smart Materials and Bone Tissue Engineering," 16 pages (2013).

International Search Report issued in co-pending International Patent Application No. PCT/IB2017/053288, completed Jul. 17, 2017.
Office Action dated Sep. 7, 2018 in U.S. Appl. No. 16/016,335.
Database WPI, Week 201028, Thomson Scientific (Apr. 2010) London GB, AN 2010-E08397, XP002779459.
International Search Report dated Apr. 9, 2018 in application No. PCT/IB2018/050349.
Office Action dated Jul. 17, 2019 in U.S. Appl. No. 16/016,335 (US 2018-0296472).
Office Action dated Sep. 17, 2019 in U.S. Appl. No. 16/016,335 (US 2018-0296472).
"Gastric acid," Wikipedia, en.wikipedia.org/wiki/Gastric_acid (accessed on May 8, 2020).
"Gastric mucosal barrier," Wikipedia, Available online, URL: wikipedia.org/wiki/Gastric mucosal barrier (accessed May 8, 2020).
Carrière, F., "Impact of gastrointestinal lipolysis on oral lipid-based formulations and bioavailability of lipophilic drugs," Biochemie 125: 297-305 (2016) Available online Nov. 2015).
Gizurarson, S., "The Effect of Cilia and the Mucociliary Clearance on Successful Drug Delivery," Biol. Pharm. Bull. 38(4): 497-506 (2015) (Published online Feb. 2015).
Leal et al., "Physicochemical properties of mucus and their impact on transmucosal drug delivery," International Journal of Pharmaceutics 532: 555-572 (2017) (published online Sep. 2017).
Mudie et al., "Quantification of Gastrointestinal Liquid Volumes and Distribution Following a 240 mL Dose of Water in the Fasted State," Molecular Pharmaceutics 11: 3039-47 (Aug. 2014).

* cited by examiner

NASAL PHARMACEUTICAL COMPOSITIONS WITH A POROUS EXCIPIENT

CROSS-REFERENCE TO RELATED APPLICATIONS

This application claims priority under 35 U.S.C. § 119 to U.S. provisional patent application 62/345,369, filed Jun. 3, 2016, the entire contents of which are incorporated herein by reference.

FIELD

Described herein are nasal pharmaceutical compositions comprising a porous excipient and an active agent, wherein the active agent is loaded onto a surface of the porous excipient located inside pores of the porous excipient, and wherein the composition is adapted for nasal administration. Also described herein are methods of making and using nasal pharmaceutical compositions.

BACKGROUND

Intranasal delivery of active agents is limited due to the physiological characteristics of the nasal cavity, the physicochemical properties of the active agents, and pharmaceutical factors such as the limited application volumes. The dose solubility volume, which considers the solubility of an active agent in view of its dose, is especially poor in compositions with active agents that are poorly soluble or unstable active in physiological solutions. Moreover, incorporation of additional additives such as a suspending agent, cosolvents, charge modifying agents, degradative enzyme inhibitors, antioxidants, stabilizers, membrane-penetration enhancing agents, emulsifying agents, wetting agents, adhesives, viscosity enhancing agents, and/or taste-masking agents further increases the volume of such compositions. Such high volumes are problematic, especially in the context of nasal delivery compositions. Thus, there is a need in the art for new nasal pharmaceutical compositions that effectively deliver a therapeutically effective amount of active agent.

SUMMARY

Surprisingly, Applicant discovered new nasal pharmaceutical compositions that solve problems associated with traditional nasal pharmaceutical formulations, as discussed below.

Provided are nasal pharmaceutical compositions comprising a porous excipient and an active agent, wherein the active agent is loaded onto a surface of the porous excipient located inside pores of the porous excipient, and wherein the composition is adapted for nasal administration.

In some embodiments, the porous excipient comprises a material selected from the group consisting of inorganic porous materials, organic-inorganic hybrids, organic polymers, and complexing agents. In specific embodiments, the porous excipient is an inorganic porous material selected from the group consisting of microporous silica, mesoporous silica, macroporous silica, polyorganosiloxanes, pharmaceutical clays, silicon dioxide nanotubes, silica gel, magnesium alumosilicate, anhydrous calcium phosphate, and calcium carbonate. In specific embodiments, the porous excipient is colloidal silicon dioxide. In specific embodiments, the porous excipient is an organic-inorganic hybrid that is a metal-organic framework. In specific embodiments, the porous excipient is an organic polymer formed by a carbon-carbon coupling reaction, wherein the organic-inorganic hybrid comprises non-metallic elements. In specific embodiments, the porous excipient is a complexing agent is an ion exchange resin selected from the group consisting of β-cyclodextrin-based porous silica, α-cyclodextrin-based porous silica, hydroxypropyl-β-cyclodextrin-based porous silica, and porous materials based on other ion exchange resins.

In some embodiments, the porous excipient comprises pores with a longest diameter in any dimension of up to 2 nm.

In some embodiments, the porous excipient loaded with the active agent is coated with a polymer. The composition of claim 9, wherein the polymer forms a shell around the porous excipient. In some embodiments, the polymer is selected from the group consisting of a linear polymer, a cellulose-containing polymer, a copolymer, a cross-linked polymer, a collagen-containing polymer, and combinations of any two or more thereof. In specific embodiments, the linear polymer is selected from the group consisting of polyvinylpyrrolidone, hyaluronic acid, chitosan, xanthan, alginate, polyvinyl acetate, sodium starch glycolate, and combinations of any two or more thereof. In specific embodiments, the cellulose-containing polymer is sodium carboxymethylcellulose. In specific embodiments, the copolymer is selected from the group consisting of polyvinylpyrrolidone/polyvinyl acetate, polyvinylpyrrolidone/polyvinyl alcohol, polyvinyl alcohol/PEG, polyvinyl caprolactam/polyvinyl acetate/polyethylene glycol, and combinations of any two or more thereof. In specific embodiments, the cross-linked polymer is selected from the group consisting of cross-linked polyvinylpyrrolidone, crosslinked sodium carboxymethylcellulose, and combinations of any two or more thereof. In specific embodiments, the collagen-containing polymer is gelatin. In some embodiments, pores in the porous excipient loaded with the active agent are capped with a coating.

In some embodiments, the composition comprises an active agent selected from the group consisting of aripiprazol, quetiapin, paliperidon, duloxetine, dopamine, testosterone, glatirameracetat, interferon beta-1a, interferon beta-1b, fingolimod, natalizumab, dimethylfumarat, pregnenolone, memantine, rivastigmin, donepezil, desvenlafaxine, progesterone, eszopiclone, eszopiclone, atomoxetin, guanfacine, methylphenidate, lisdexamfetamine, recombinant tissue plasminogen activator (rt-PA), methotrexate, raltitrexed, 5-fluorouracil, telomerase inhibitor, monoclonal antibodies, midazolam, lacosamide, levetiracetam, lamotrigine, valproic acid, oxycodone, pregabalin, buprenorphine, hydrocodone, fentanyl, safinamide, ropinirole, pramipexole, L-DOPA, selegiline, cabergoline, istradefylline, and combinations of two or more thereof. In some embodiments, the composition is a vaccine, and the active agent comprises an immunogen. In some embodiments, the active agent is in amorphous form.

In some embodiments, the composition comprises a therapeutically effective amount of the active agent. In some embodiments, the composition comprises from about 1% to about 50% (w/w) active agent based on the weight of the composition.

In some embodiments, the composition is in the form of a gel. In some embodiments, the loaded porous excipient is dispersed in a gel. In some embodiments, the gel comprises a vehicle comprising an oil or mixture of oils. In specific embodiments, the vehicle comprises castor oil.

Some embodiments comprise nasal pharmaceutical compositions comprising: (a) a porous excipient and an active agent, wherein the active agent is loaded onto a surface of the porous excipient located inside pores of the porous excipient; (b) a lipophilic or partly lipophilic vehicle; and (c) a viscosity-regulating agent.

Some embodiments comprise nasal pharmaceutical compositions comprising: (a) a porous excipient and an active agent, wherein the active agent is loaded onto a surface of the porous excipient located inside pores of the porous excipient; (b) a shell disposed on the porous excipient, wherein the shell contains an active agent that is the same as or different from the active agent loaded onto the porous excipient; (c) a lipophilic or partly lipophilic vehicle; (d) a viscosity-regulating agent; and (e) a surfactant. In some embodiments, the lipophilic or partly lipophilic vehicle contains an active agent.

Some embodiments comprise nasal pharmaceutical compositions comprising: (a) a mesoporous silica excipient and an active agent, wherein the active agent is loaded onto a surface of the mesoporous silica located inside pores of the mesoporous silica; (b) at least one lipophilic or partly lipophilic vehicle; and (c) at least one viscosity-regulating agent.

Some embodiments comprise nasal pharmaceutical compositions comprising: (a) from about 0.5% to about 50% w/w of a mesoporous silica excipient, based on the weight of the composition; (b) from about 0.5% to about 40% w/w of active agent, based on the weight of the composition, wherein the active agent is loaded onto a surface of the mesoporous silica located inside pores of the mesoporous silica; (b) from about 50% to about 90% w/w of castor oil, based on the weight of the composition; and (c) from about 2% to about 6% w/w of a mixture of oleoyl macrogolglycerides, based on the weight of the composition.

Some embodiments comprise nasal pharmaceutical compositions comprising: (a) about 8% w/w of a mesoporous silica excipient, based on the weight of the composition; (b) about 5% w/w of active agent, based on the weight of the composition, wherein the active agent is loaded onto a surface of the mesoporous silica located inside pores of the mesoporous silica; (c) about 80% w/w of castor oil, based on the weight of the composition; and (d) about 10% w/w of colloidal silicon dioxide, based on the weight of the composition.

Some embodiments comprise nasal pharmaceutical compositions comprising: (a) about 8% w/w of a mesoporous silica excipient, based on the weight of the composition; (b) about 5% w/w of active agent, based on the weight of the composition, wherein the active agent is loaded onto a surface of the mesoporous silica located inside pores of the mesoporous silica; (c) about 80% w/w of castor oil, based on the weight of the composition; and (d) about 4% w/w of a mixture of oleoyl macrogolglycerides, based on the weight of the composition.

In some pharmaceutical compositions described herein, the active agent is testosterone.

In some pharmaceutical compositions, the active agent is progesterone.

Some embodiments comprise methods for intranasal delivery of an active agent, comprising nasally administering to a subject in need thereof a composition as described herein.

Also provided are methods of vaccinating a subject against a condition comprising nasally administering a composition to a subject in need thereof, wherein the active agent comprises an immunogen, such as wherein: (a) the condition is influenza, and the active agent is live attenuated influenza virus, inactivated virus, or viral antigens; the condition is hepatitis B, and the active agent is Hepatitis B virus (HBV), surface hepatitis B antigens (HBsAg), and/or core hepatitis B antigens (HBcAg); or (c) The condition is meningitis, and the active agent is meningococcal polysaccharide vaccine (MPSV4, polysaccharide from the surface of the meningococcal bacteria), meningococcal conjugate vaccine (MCV4, polysaccharide chemically bonded to protein) and/or meningococcal serogroup B vaccine (MenB, which contains four proteins taken from group B *Neisseria meningitidis* bacteria). In specific embodiments, the live attenuated influenza is selected from the group consisting of A/California/7/2009 (H1N1), an A/California/7/2009 (H1N1)-like strain, A/Switzerland/9715293/2013 (H3N2), an A/Switzerland/9715293/2013 (H3N2)-like strain, B/Phuket/3073/2013, a B/Phuket/3073/2013-like strain (B/Yamagata lineage), B/Brisbane/60/2008, a B/Brisbane/60/2008-like strain (B/Victoria lineage vaccine virus), and combinations of two or more thereof. In specific embodiments, the antigens are selected from the group consisting of antigens from influenza virus A/Panama/2007/99 (H3N2), B/Guandong/2000, and/or A/Duck/Singapore/97 (H5N3).

Also provided are compositions for use in vaccinating against a condition, wherein the active agent comprises an immunogen, such as wherein: (a) the condition is influenza, and the active agent is live attenuated influenza virus, inactivated virus, or viral antigens; (b) The condition is hepatitis B, and the active agent is Hepatitis B virus (HBV), surface hepatitis B antigens (HBsAg), and/or core hepatitis B antigens (HBcAg); or (c) The condition is meningitis, and the active agent is meningococcal polysaccharide vaccine (MPSV4, polysaccharide from the surface of the meningococcal bacteria), meningococcal conjugate vaccine (MCV4, polysaccharide chemically bonded to protein) and/or meningococcal serogroup B vaccine (MenB, which contains four proteins taken from group B *Neisseria meningitidis* bacteria).

Also provided are compositions for use in making a vaccine against a condition wherein the active agent comprises an immunogen, such as wherein: (a) the condition is influenza, and the active agent is live attenuated influenza virus, inactivated virus, or viral antigens; (b) The condition is hepatitis B, and the active agent is Hepatitis B virus (HBV), surface hepatitis B antigens (HBsAg), and/or core hepatitis B antigens (HBcAg); or (c) The condition is meningitis, and the active agent is meningococcal polysaccharide vaccine (MPSV4, polysaccharide from the surface of the meningococcal bacteria), meningococcal conjugate vaccine (MCV4, polysaccharide chemically bonded to protein) and/or meningococcal serogroup B vaccine (MenB, which contains four proteins taken from group B *Neisseria meningitidis* bacteria).

Also provided are methods for treating a condition comprising nasally administering a composition as described herein to a subject in need thereof, wherein: (a) the condition is hypogonadism, female sexual dysfunction, female arousal disorder, anorgasmia, or hypoactive sexual desire disorder, and the active agent is testosterone; (b) the condition is a brain injury, and the active agent is progesterone; (c) the condition is schizophrenia, and the active agent is aripiprazol, auetiapin, or paliperidon; (d) the condition is anxiety, and the active agent is duloxetine or dopamine; (e) the condition is multiple sclerosis, and the active agent is testosterone, glatirameracetat, interferon beta-1a, interferon beta-1b, fingolimod, natalizumab, or dimethylfumarat; (f) the condition is Alzheimer's disease, and the active agent is pregnenolone, memantine, rivastigmin, or donepezil; (g) the condition is depression, and the active agent is desvenlafaxine, duloxetine, or dopamine; (h) the condition is insomnia, and the active agent is progesterone, eszopiclone or eszopiclone; (i) the condition is attention deficit hyperactive disorder, and the active agent is tomoxetin, guanfacine, methylphenidate, lisdexamfetamine, or dopamine; (j) the condition is traumatic brain injury, and the active agent progesterone or recombinant tissue plasminogen activator (rt-PA); (k) the condition is a braun tumor, and the active agent is methotrexate, raltitrexed, 5-fluorouracil, telomerase inhibitor, or monoclonal antibodies; (l) the condition is epilepsy, and the active agent is midazolam, lacosamide, levetiracetam, lamotrigine, or valproic acid; (m) the condition is pain, and the active agent is oxycodone, pregabalin, buprenorphine, hydrocodone, or fentanyl; or (n) the condition is Parkinson's disease, and the active agent is safinamide, ropinirole, pramipexole, dopamine, L-DOPA, selegiline, cabergoline, or istradefylline.

Also provided are compositions for use in treating a condition, wherein: (a) the condition is hypogonadism, female sexual dysfunction, female arousal disorder, anorgasmia, or hypoactive sexual desire disorder, and the active agent is testosterone; (b) the condition is a brain injury, and the active agent is progesterone; (c) the condition is schizophrenia, and the active agent is aripiprazol, auetiapin, or paliperidon; (d) the condition is anxiety, and the active agent is duloxetine or dopamine; (e) the condition is multiple sclerosis, and the active agent is testosterone, glatirameracetat, interferon beta-1a, interferon beta-1b, fingolimod, natalizumab, or dimethylfumarat; (f) the condition is Alzheimer's disease, and the active agent is pregnenolone, memantine, rivastigmin, or donepezil; (g) the condition is depression, and the active agent is desvenlafaxine, duloxetine, or dopamine; (h) the condition is insomnia, and the active agent is progesterone, eszopiclone or eszopiclone; (i) the condition is attention deficit hyperactive disorder, and the active agent is tomoxetin, guanfacine, methylphenidate, lisdexamfetamine, or dopamine; (j) the condition is traumatic brain injury, and the active agent progesterone or recombinant tissue plasminogen activator (rt-PA); (k) the condition is a braun tumor, and the active agent is methotrexate, raltitrexed, 5-fluorouracil, telomerase inhibitor, or monoclonal antibodies; (l) the condition is epilepsy, and the active agent is midazolam, lacosamide, levetiracetam, lamotrigine, or valproic acid; (m) the condition is pain, and the active agent is oxycodone, pregabalin, buprenorphine, hydrocodone, or fentanyl; or (n) the condition is Parkinson's disease, and the active agent is safinamide, ropinirole, pramipexole, dopamine, L-DOPA, selegiline, cabergoline, or istradefylline.

Also provided are compositions for use in making a medicament for the treatment of a condition, wherein: (a) the condition is hypogonadism, female sexual dysfunction, female arousal disorder, anorgasmia, or hypoactive sexual desire disorder, and the active agent is testosterone; (b) the condition is a brain injury, and the active agent is progesterone; (c) the condition is schizophrenia, and the active agent is aripiprazol, auetiapin, or paliperidon; (d) the condition is anxiety, and the active agent is duloxetine or dopamine; (e) the condition is multiple sclerosis, and the active agent is testosterone, glatirameracetat, interferon beta-1a, interferon beta-1b, fingolimod, natalizumab, or dimethylfumarat; (f) the condition is Alzheimer's disease, and the active agent is pregnenolone, memantine, rivastigmin, or donepezil; (g) the condition is depression, and the active agent is desvenlafaxine, duloxetine, or dopamine; (h) the condition is insomnia, and the active agent is progesterone, eszopiclone or eszopiclone; (i) the condition is attention deficit hyperactive disorder, and the active agent is tomoxetin, guanfacine, methylphenidate, lisdexamfetamine, or dopamine; (j) the condition is traumatic brain injury, and the active agent progesterone or recombinant tissue plasminogen activator (rt-PA); (k) the condition is a braun tumor, and the active agent is methotrexate, raltitrexed, 5-fluorouracil, telomerase inhibitor, or monoclonal antibodies; (l) the condition is epilepsy, and the active agent is midazolam, lacosamide, levetiracetam, lamotrigine, or valproic acid; (m) the condition is pain, and the active agent is oxycodone, pregabalin, buprenorphine, hydrocodone, or fentanyl; or (n) the condition is Parkinson's disease, and the active agent is safinamide, ropinirole, pramipexole, dopamine, L-DOPA, selegiline, cabergoline, or istradefylline.

Some embodiments comprise methods for treating nasal congestion comprising administering a composition to a subject in need thereof, wherein the active agent comprises one or more of a nasal antihistamine and a decongestant. In some embodiments, the nasal congestion is caused by one or more of dry nose/crusts, common cold, hay fever, upper respiratory tract allergies, and age. In some embodiments, the active agent comprises one or more of a corticosteroid, naphazoline, oxymetazoline, adrenaline, phenylephrine, nasal saline spray, brompheniramine, chlorpheniramine, clemastine, diphenhydramine, desloratadine, fexofenadine, loratadine, cromolyn, ectoin, and plant and/or anthroposophical substances.

Some embodiments comprise a composition for use in treating nasal congestion. Some embodiments comprise a composition for use in making a medicament for treatment of nasal congestion. In some embodiments, the nasal congestion is caused by one or more of dry nose/crusts, common cold, hay fever, upper respiratory tract allergies, and age. In some embodiments, the active agent comprises one or more of a corticosteroid, naphazoline, oxymetazoline, adrenaline, phenylephrine, nasal saline spray, brompheniramine, chlorpheniramine, clemastine, diphenhydramine, desloratadine, fexofenadine, loratadine, cromolyn, ectoin, and plant and/or anthroposophical substances.

DETAILED DESCRIPTION

Definitions

Figure 1:
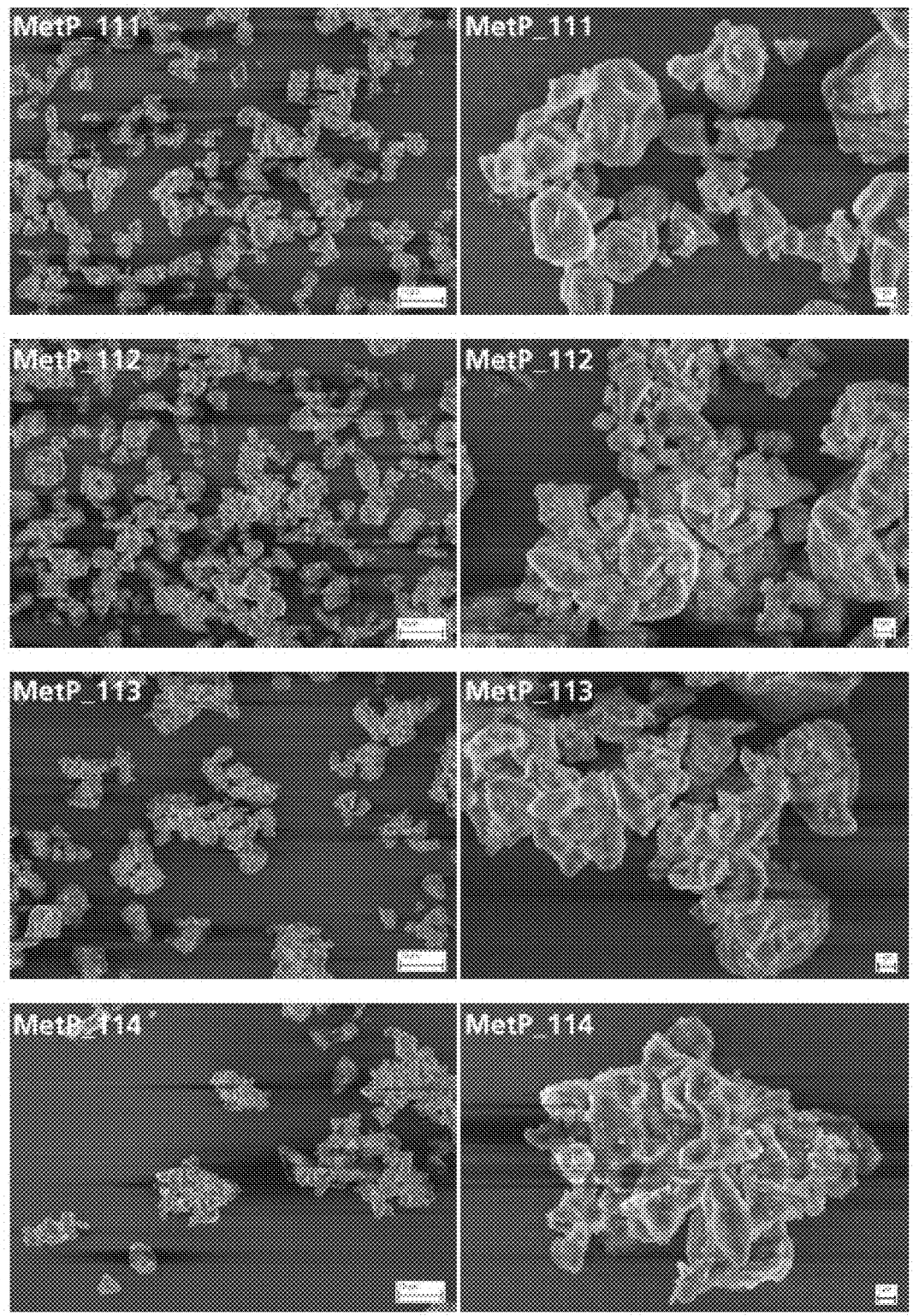
FIG. 1 shows scanning electron micrographs of various spray dried compositions as described herein with progesterone and SYLOID® 72FP particles.

Technical and scientific terms used herein have the meanings commonly understood by one of ordinary skill in the art to which the present invention pertains, unless otherwise defined. Reference is made herein to various methodologies known to those of ordinary skill in the art. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted. Publications and other materials setting forth such known methodologies to which reference is made are incorporated herein by reference in their entireties as though set forth in full.

As used herein, the singular forms "a," "an," and "the" designate both the singular and the plural, unless expressly stated to designate the singular only.

The term "about" means that the number comprehended is not limited to the exact number set forth herein, and is intended to refer to numbers substantially around the recited number while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein "subject" denotes any mammal in need of active agent therapy, including humans. For example, a subject may be suffering from or at risk of developing a condition that can be treated or prevented with an active agent, or may be taking an active agent for health maintenance purposes.

As used herein, the phrases "therapeutically effective amount" and "therapeutic level" mean that active agent dosage or plasma concentration in a subject, respectively, that provides the specific pharmacological effect for which the active agent is administered in a subject in need of such treatment. It is emphasized that a therapeutically effective amount or therapeutic level of an active agent will not always be effective in treating the conditions/diseases described herein, even though such dosage is deemed to be a therapeutically effective amount by those of skill in the art. For convenience only, exemplary dosages, active agent delivery amounts, therapeutically effective amounts and therapeutic levels are provided below with reference to adult human subjects. Those skilled in the art can adjust such amounts in accordance with standard practices as needed to treat a specific subject and/or condition/disease.

"Theoretical loading" of an active agent means the wt % of the of the active agent in a composition or porous excipient if the active agent is incorporated into the composition or porous excipient with 100% efficiency. Thus, the theoretical loading of an active agent on a porous excipient can be calculated using the following equation: theoretical loading=100×(weight of active agent added (g))/(weight of active agent (g)+porous excipient (g)).

"Actual loading" of an active agent means the actual amount of active agent incorporated into the composition or porous excipient. Thus, the actual loading of an active agent on a porous excipient can be calculated using the following equation: 100×(weight of active agent (g) in 1 gram of loaded porous excipient)/(1 g of loaded porous excipient).

"Loading efficiency" can be calculated according to the following equation: loading efficiency=100×(total amount of active agent in the yield (g))/(actual amount of active agent added during loading).

Active Agents

The active agent can include any one or more therapeutic agents that can be administered intranasally for a therapeutic effect. In some embodiments, the active agent comprises a hormone, such as testosterone, progesterone, pregnenolone, or a prodrug or derivative of any of these. In some embodiments, the active agent comprises a neurotransmitter, such as dopamine, L-DOPA, or serotonin. In some embodiments, the active agent comprises an opioid analgesic, such as fentanyl or hydromorphone. In some embodiments, the active agent comprises a benzodiazepine, such as midazolam. In some embodiments, the active agent comprises a protein, such as insulin or a growth hormone (e.g., human growth hormone). In some embodiments, the active agent comprises a cholinesterase inhibitor, such as donepezil, rivastigmine, or galantamine. In some embodiments, the active agent comprises a nasal antihistamine and/or a decongestant, such as a corticosteroid, naphazoline, oxymetazoline, adrenaline, phenylephrine, nasal saline spray, brompheniramine, chlorpheniramine, clemastine, diphenhydramine, desloratadine, fexofenadine, loratadine, cromolyn, ectoin, or plants and anthroposophical substances. In some embodiments, the active agent is selected from the group consisting of aripiprazol, quetiapin, paliperidon, duloxetine, dopamine, testosterone, glatirameracetat, interferon beta-1a, interferon beta-1b, fingolimod, natalizumab, dimethylfumarat, pregnenolone, memantine, rivastigmin, donepezil, desvenlafaxine, progesterone, eszopiclone, eszopiclone, atomoxetin, guanfacine, methylphenidate, lisdexamfetamine, recombinant tissue plasminogen activator (rt-PA), methotrexate, raltitrexed, 5-fluorouracil, telomerase inhibitor, monoclonal antibodies, midazolam, lacosamide, levetiracetam, lamotrigine, valproic acid, oxycodone, pregabalin, buprenorphine, hydrocodone, fentanyl, safinamide, ropinirole, pramipexole, L-DOPA, selegiline, cabergoline, istradefylline, and combinations of two or more thereof.

In some embodiments, the composition is useful as a vaccine, and the active agent comprises an immunogen, such as an influenza vaccine, a hepatitis B vaccine, or a meningitis vaccine. In embodiments where the composition is useful as an influenza vaccine, the active agent loaded onto the porous excipient can be immunogenic against influenza. Exemplary active agents loaded onto the porous excipient when the composition is useful as an influenza vaccine include live attenuated influenza (such as but not limited to A/California/7/2009 (H1N1) or an A/California/7/2009 (H1N1)-like strain; A/Switzerland/9715293/2013 (H3N2) or an A/Switzerland/9715293/2013 (H3N2)-like strain; B/Phuket/3073/2013 or a B/Phuket/3073/2013-like strain (B/Yamagata lineage); B/Brisbane/60/2008 or a B/Brisbane/60/2008-like strain (B/Victoria lineage vaccine virus)). In some embodiments where the composition is useful as an influenza vaccine, the active agent loaded onto the porous excipient comprises an inactivated virus or viral antigens (such as but not limited to antigens from influenza virus A/Panama/2007/99 (H3N2), B/Guandong/2000, and/or an avian strain such as A/Duck/Singapore/97 (H5N3)).

In embodiments where the composition is useful as a hepatitis B vaccine, the active agent loaded onto the porous excipient can comprise, for example, Hepatitis B virus (HBV), surface hepatitis B antigens (HBsAg), and/or core hepatitis B antigens (HBcAg).

In embodiments where the composition is useful as a meningitis vaccine, the active agent loaded onto the porous excipient can comprise, for example, meningococcal polysaccharide vaccine (MPSV4, polysaccharide from the surface of the meningococcal bacteria), meningococcal conjugate vaccine (MCV4, polysaccharide chemically bonded to protein) and/or meningococcal serogroup B vaccine (MenB, which contains four proteins taken from group B *Neisseria meningitidis* bacteria).

In some embodiments, the composition is useful in treating nasal congestion, such as may be caused by dry nose/crusts, common cold, hay fever, upper respiratory tract allergies, or age. In specific embodiments useful in treating nasal congestion, the active agent comprises a nasal antihistamine and/or a decongestant, such as a corticosteroid, naphazoline, oxymetazoline, adrenaline, phenylephrine, nasal saline spray, brompheniramine, chlorpheniramine, clemastine, diphenhydramine, desloratadine, fexofenadine, loratadine, cromolyn, ectoin, or plants and anthroposophical substances.

In some embodiments, the composition comprises active agent in amorphous form. In some embodiments, the composition comprises an active agent in crystalline form. In some embodiments, the composition comprises an active agent in both amorphous form and crystalline form. For example, amorphous active agent may be loaded onto the porous excipient inside the pores of the excipient, and crystalline active agent may be included in a coating and/or provided in a vehicle of the composition, such as being dissolved, suspended, or dispersed in the vehicle of the composition.

In some embodiments, the composition contains an active agent that is less than about 0.1%, less than about 0.5%, less than about 1%, or less than about 5% in crystalline form, such as less than 0.1%, less than 0.5%, less than 1%, or less than 5% in crystalline form. In some embodiments, the composition contains substantially no crystalline form of the active agent.

In some embodiments the active agent can be used in a form that it not typically used, such as a polymorph or salt that may not exhibit satisfactory stability in typical formulations. Without being bound by theory, it is believed that loading the active agent onto a porous excipient as described herein may stabilize the active agent, both against chemical reactions and against physical modifications (such as intropolymorph conversion). In some embodiments, the porous excipient is selected and/or prepared for this purpose, such as by using a certain quality of silicon dioxide that stabilizes the active agent at issue.

Nasal Compositions

Provided herein are nasal compositions comprising a porous excipient and an active agent. Also provided are methods of making and using nasal compositions comprising a porous excipient and an active agent.

By "nasal compositions" is meant compositions suitable for, or adapted for, nasal delivery, including intra-nasal delivery. The specific form of the nasal composition is not limited. In some embodiments, the nasal composition is in the form of a solution, suspension, dispersion, emulsion, or gel. In some embodiments, the composition is in the form of an oily liquid. In some embodiments, the composition is non-aqueous or water-free. (As used herein, "water-free" means that the composition is formulated without water, although trace amounts may be present.) In some embodiments, the composition comprises a water-free semi-liquid phase. In some embodiments, the composition is a hydrophilic gel or an emulgel (i.e., an emulsion incorporated in a gel base). In some embodiments, the composition is a hydrophobic gel, such as an oleogel or an organogel. In some embodiments, the composition comprises a three-dimensional, viscoelastic gel with small molecular weight organoregulators and/or polymeric gelators. In some embodiments, the composition is spreadable.

The nasal compositions described herein comprise (a) an active agent and (b) a porous excipient, wherein the active agent is loaded onto a surface of the porous excipient located inside pores of the porous excipient. In some embodiments, the compositions further comprise a vehicle. In some embodiments, the compositions further comprise a viscosity-regulating agent. In some embodiments, the porous excipient is provided with a shell, which may (or may not) contain an active agent (which can be the same as or different from the active agent loaded onto the porous excipient). In some embodiments, the composition comprises a surfactant. In some embodiments, the composition comprises porous excipient embedded in a gel network, such as a hydrophobic gel.

In some embodiments, at least a portion of the porous excipient loaded with active agent is in the form of particles. In some embodiments, about 10% of particles have a longest diameter in any dimension of less than about 0.2 µm, or less than about 0.1 µm. In some embodiments, about 90% of the particles have a longest diameter of less than about 15.5 µm, less than about 7.5 µm, or less than about 4.2 µm. In some embodiments, about 50% of the particles have a longest diameter of less than about 5.2 µm, less than about 2 µm, or less than about 0.9 µm.

In some embodiments, the active agent is present in the nasal composition in an amount of from about 0.1% w/w to about 70% w/w, including from about 0.5% w/w to about 40% w/w, about 5% w/w to about 40% w/w, about 10% w/w to about 30% w/w, and about 15% w/w to about 25% w/w, based on the total weight of the composition, and amounts between any of these values, including about 0.1%, about 0.5%, about 1% w/w, about 5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w or about 70% w/w. In some embodiments, the active agent is present in the nasal composition in an amount of from 0.1% w/w to 70% w/w, including from 0.5% w/w to 40% w/w, 5% w/w to 40% w/w, 10% w/w to 30% w/w, and 15% w/w to 25% w/w, based on the total weight of the composition. In some embodiments, the active agent is present in an amount of 0.1%, 0.5%, 1% w/w, 5% w/w, 10% w/w, 15% w/w, 20% w/w, 25% w/w, 30% w/w, 35% w/w, 40% w/w, 45% w/w, 50% w/w, 55% w/w, 60% w/w or 70% w/w, based on the total weight of the composition.

In some embodiments, the composition comprises at least about 1 µg of active agent per 150 mg of the composition. In some embodiments, the composition comprises from about 1 µg to about 100 mg of active agent per 150 mg of the composition, or about 1 mg to about 50 mg of active agent per 150 mg of the composition, or about 5 mg to about 20 mg of active agent per 150 mg of the composition, or about 50 µg to about 250 µg of active agent per 150 mg of the composition. In some embodiments, the composition comprises about 1 g, about 10 g, about 20 µg, about 50 µg, about 100 µg, about 250 µg, about 500 µg, about 1 mg, about 2 mg, about 5 mg about 5.5 mg, about 7 mg, about 8 mg, about 9 mg, about 10 mg, about 15 mg, about 20 mg about 25 mg, or about 50 mg of active agent per 150 mg of the composition. In some embodiments, the composition comprises 1 g, 10 g, 20 g, 50 g, 100 g, 250 g, 500 µg 1 mg 2 mg, 5 mg, 5.5 mg, 7 mg 8 mg, 9 mg, 10 mg, 15 mg, 20 mg 25 mg or 50 mg of active agent per 150 mg of the composition.

The composition may be adapted for nasal administration of any suitable amount of composition, keeping in mind the volume limitations of nasal administration. In some embodiments the composition is adapted for administration of about 0.1 ml to about 1 ml per nostril, such as from about 0.1 ml to about 0.3 ml, about 0.15 ml to about 0.25 ml, or about 0.175 to about 0.225 ml per nostril. Some embodiments are adapted for administration of 0.1 ml to 1 ml per nostril, such as from 0.1 ml to 0.3 ml, 0.15 ml to 0.25 ml, or 0.175 to 0.225 ml per nostril. In some embodiments, the composition is adapted for administration of about 0.1 ml, about 0.15 ml, about 0.2 ml, about 0.25 ml, or about 0.3 ml per nostril. Some embodiments are adapted for administration of 0.1 ml, 0.15 ml, 0.2 ml, 0.25 ml, or 0.3 ml per nostril. In some embodiments, the composition is adapted for administration of about 0.2 ml or less per nostril. In some embodiments, the composition is adapted for administration of 0.2 ml or less per nostril.

In some embodiments, the composition is adapted for once daily administration per nostril, to one or both nostrils. In some embodiments, the composition is adapted for twice daily administration per nostril, to one or both nostrils. In some embodiments, the composition is administered three, four, five, or six times per day per nostril, to one or both nostrils.

In some embodiments, the composition is stable (e.g., contains substantially no degradation-related impurities) for at least about 1 month, at least about 2 months, at least about 3 months, or at least about 6 months, such as after storage, for example, at 25° C. and 60% relative humidity, at 30° C. and 65% relative humidity, or room temperature and humidity conditions. In some embodiments, the composition is stable for at least 1 month, at least 2 months, at least 3 months, or at least 6 months, such as after storage, for example, at 25° C. and 60% relative humidity, at 30° C. and 65% relative humidity, or room temperature and humidity conditions.

Porous Excipients

As noted above, the nasal compositions described herein comprise (a) an active agent and (b) a porous excipient. The porous excipient can be any porous material onto which the active agent can be loaded. In some embodiments, the active agent is loaded onto surfaces of the porous excipient, including surfaces located inside pores of the excipient. In some embodiments, the porous excipient acts as a matrix for the active agent. In some embodiments, the composition further comprises active agent that is not loaded onto the porous excipient; for example, the composition can comprise active agent in addition to active agent that is loaded onto the porous excipient.

The porous excipient may be comprised of any material suitable for use in a nasal pharmaceutical composition and onto which active agent can be loaded in accordance with the disclosure herein. Non-limiting examples of suitable materials are provided below.

In some embodiments, the porous agent comprises an inorganic porous material, such as colloidal silicon dioxide, micro-porous silicon dioxide, meso-porous silicon dioxide, macro-porous silicon dioxide, polyorganosiloxanes, pharmaceutical clays, silicon dioxide nanotubes, silicon dioxide gel, magnesium alumosilicate (such as but not limited to VEEGUM® from Vanderbilt Minerals, LLC), activated carbon, anhydrous calcium phosphate, calcium carbonate, alumina, and combinations of any two or more thereof. Exemplary inorganic porous materials include porous silicon dioxide commercially available under the SYLOID® brand from W.R. Grace & Co. (such as but not limited to SYLOID® 244FP, 72FP, XDP6035 (also known as SIL-SOL™ 6035), XDP3050, XDP3150, AL-1FP, and combinations of any two or more thereof), porous silicon dioxide available under the AEROPERL® brand from Evonik Industries, Corp. (such as but not limited to AEROPERL® 300, which has a surface area of about 260 to 320 $m^2/g$ (such as about 300 $m^2/g$), a pore volume of about 1.5 to 1.9 ml/g, and an average particle size of about 20 to about 60 μm), silicon dioxide PARTECK® SLC from EMD Millipore, NEUSILIN® (a synthetic, amorphous form of magnesium aluminometasilicate) from Fuji Chemical Industry, Zeolite Socony Mobil-5, Mobil Composition of Matter No. 41, SBA-15, FDU-11, OMS-7, OMS-Lemon-7, and IT™-56. In some embodiments, the porous agent comprises silicon-based powders, which may be hydrophobic or hydrophilic, e.g., depending on groups chemically bonded to their surfaces.

For reference, approximate specifications of various SYLOID® inorganic porous materials are as follows:

some embodiments, microporous organic polymers are formed by carbon-carbon coupling reactions and comprised of non-metallic elements such as carbon, hydrogen, oxygen, nitrogen, and/or boron. In some embodiments, organic polymers are produced by emulsion polymerization and hyper-crosslinking followed by chemical etching of sacrificial $SiO_2$ cores. In some embodiments, networks of organic polymers are constructed from small organic building blocks.

In some embodiments, the porous excipient comprises porous materials based on complexing agents, such as an ion exchange resin (such as but not limited to cross-linked polystyrene) or an adsorbent (such as but not limited to β-cyclodextrin-based porous silica, α-cyclodextrin-based porous silica, hydroxpropyl-β-cyclodextrin-based porous silica, and porous materials based on other adsorbent resins).

In some embodiments the porous excipient comprises a material with pores with highly variable sizes and irregular shapes, such as an agent comprising polylactide and/or polylactic acid. In some embodiments, the polylactide comprises polylactides available under the RESOMER® brand available from Sigma-Aldrich (such as but not limited to RESOMER® 202H (which has a molecular weight of about 10,000 to about 18,000 Da; a viscosity of about 0.16 to about 0.24 dl/g; a $T_g$ of about 44 to about 48° C.; and free carboxylic acid end groups) and RESOMER® 202S (which has a molecular weight of about 10,000 to about 18,000 Da; a viscosity of about 0.16 to about 0.24 dl/g; a $T_g$ of about 38 to about 42° C.; and ester terminated end groups)), and combinations of two or more thereof. In some embodiments, the porous agent comprises polysaccharides, such as chitosan (such as but not limited to chitosan with 95% degree of deacylation and a viscosity of about 200 mPa). An exemplary chitosan in this regard is CHITOSCIENCE® Chitosan 95/200 from Heppe Medical Chitosan GmbH. In some embodiments, the porous agent comprises peptides and/or proteins, such as gelatin (such as but not limited to gelatin with bloom grades F15, F20, F25, or combinations of two or more thereof).

In some embodiments, the porous excipient comprises porous particles. Without being bound by theory, it is believed that even small and large particles can be effective by fixing them in a gel network using chemical and/or physical bonds, such as H-bonding and van der Walls forces. In any embodiments where the porous excipient comprises porous particles, the particles may have a longest diameter in any dimension of from about 0.5 μm to about 350 μm, such as from about 50 μm to about 300 μm, about 100 μm

| Property | AL-1FP | 72FP | 244FP | XDP3050 | XDP3150 | XDP6035 |
|---|---|---|---|---|---|---|
| $SiO_2$ (dried basis) (%) | 99.6 | 99.6 | 99.6 | 99.6 | 99.6 | 99.8 |
| Average particle size (μm) | 7.5 | 6.0 | 3.5 | 50 | 150 | 37 |
| Oil adsorption (lbs/100 lbs) | 80 | 220 | 300 | 300 | 300 | |
| Bulk density (g/l) | 566 | 112 | 70 | 275 | 275 | 420 |
| Average pore volume (cc/gm) | 0.4 | 1.2 | 1.6 | 1.7 | 1.7 | 0.98 |

In some embodiments, the porous excipient comprises an organic-inorganic hybrid, such as metal-organic frameworks (MOFs). Exemplary hybrid materials can be formed by self-assembly of polydentate bridging ligands and metal connecting points.

In some embodiments, the porous excipient comprises organic polymers, such as microporous organic polymers, polystyrene, cellulose, and/or poly(methyl methacrylate). In to about 250 μm, about 150 μm to about 200 μm, or about 3 μm to about 35 μm. In some embodiments, the longest diameter is from 0.5 μm to 350 μm, such as from 50 μm to 300 μm, 100 m to 250 μm, 150 μm to 200 μm, or 3 μm to 35 μm. In some embodiments, the particles have a longest diameter of about 0.5 μm, about 0.8 μm, about 1 μm, about 2 μm, about 3 μm, about 5 μm, about 10 μm, about 35 μm, about 60 μm, or about 150 μm. In some embodiments, the particles have a longest diameter of 0.5 µm, 0.8 µm, 1 µm, 2 µm, 3 µm, 5 µm, 10 µm, 35 µm, 60 µm, or 150 µm.

In some embodiments, the particles have a mean diameter of from about 0.5 µm to about 350 µm, such as from about 50 µm to about 300 µm, about 100 µm to about 250 µm, about 150 µm to about 200 µm, or about 3 µm to about 35 µm. In some embodiments, the mean diameter is from 0.5 µm to 350 µm, such as from 50 µm to 300 µm, 100 µm to 250 µm, 150 µm to 200 µm, or 3 µm to 35 µm. In some embodiments, the median diameter of the particles in a composition is about 0.5 µm, about 0.8 µm, about 1 µm, about 2 µm, about 3 µm, about 5 µm, about 10 µm, about 35 µm, about 60 µm, or about 150 µm. In some embodiments, the median diameter of the particles in a composition is 0.5 µm, 0.8 µm, 1 µm, 2 µm, 3 µm, 5 µm, 10 µm, 35 µm, 60 µm, or 150 µm.

For any type of porous excipient, the porous excipient may comprise pores with a longest diameter in any dimension of 2 nm or less (e.g., the porous excipient comprises micro-porous materials). In some embodiments, the porous excipient comprises pores with a longest diameter of from about 2 nm to about 50 nm, such as from 20 nm to 50 nm (e.g., the porous excipient comprises meso-porous materials). In some embodiments, the porous excipient comprises pores with a longest diameter of 50 nm or more (e.g., the porous excipient comprises macro-porous materials). In some embodiments, the porous excipient comprises pores with a longest diameter of from about 2 nm to about 20 nm, such as from 2 nm to 20 nm. In some embodiments, at least about 90% of the pores have a diameter of from about 5 nm to about 6 nm, about 5 nm to about 7.5 nm, about 5.5 nm to about 7 nm, about 6 nm to about 7.5 nm, or 6 nm to about 8 nm. In some embodiments, at least about 90% of the pores have a diameter of from 5 nm to 6 nm, 5 nm to 7.5 nm, 5.5 nm to 7 nm, 6 nm to 7.5 nm, or 6 nm to 8 nm. In some embodiments, the pores have an average volume of from about 0.5 ml/g to about 2 ml/g, such as about 1 ml/g, about 1.6 ml/g, or about 1.75 ml/g. In some embodiments, the pores have an average volume of from 0.5 ml/g to 2 ml/g, such as 1 ml/g, 1.6 ml/g, or 1.75 ml/g. In some embodiments, the pores have an average volume of greater than about 0.9 ml/g, or greater than 0.9 ml/g. In some embodiments, the pores have a surface area of about 300 m$^2$/g or greater, or from about 320 to about 1000 m$^2$/g. In some embodiments, the pores have a surface area of 300 m$^2$/g or greater, or from 320 to 1000 m$^2$/g. In some embodiments, the pores have a surface area of 1000 m$^2$/g or greater.

The porous excipient may have pores of any type of pore structure. For example, the pore cross-section may have a regular geometric shape, such as a circular, elliptical, rectangular, or square shape, or an irregular shape. In some embodiments, the porous excipient comprises pores with a regular shape and pores with an irregular shape. In some embodiments the porous excipient additionally or alternatively comprises pores with a connected pore structure, pores with an unconnected pore structure, or both. In some embodiments the porous excipient additionally or alternatively comprises ordered arrays of pores, disordered arrays of pores, or both.

The composition may comprise any suitable amount of porous excipient, such as any amount effective to provide a therapeutically effective dose of the active agent while still being suitable for nasal administration. In some embodiments, the composition comprises from about 0.01 to about 0.5 g of porous excipient, such as from about 0.01 g to about 0.4 g of porous excipient, about 0.1 g to about 0.25 g, or about 0.05 g, about 0.1 g, about 0.15 g, about 0.2 g, about 0.25 g, or about 0.3 g of porous excipient, where the weight corresponds to the amount porous excipient prior to loading it with active agent. In some embodiments, the composition comprises from 0.01 to 0.5 g of porous excipient, such as from 0.01 g to 0.4 g of porous excipient, 0.1 g to 0.25 g, or 0.05 g, 0.1 g, 0.15 g, 0.2 g, 0.25 g, or 0.3 g of porous excipient. In some embodiments, the composition comprises from about 0.5% to about 30% w/w, about 1% to about 20% w/w, about 5% to about 15% w/w, or about 8% to about 10% w/w porous excipient, based on the weight of the pre-loaded porous excipient and the total weight of the composition. In some embodiments, the composition comprises from 0.5% to 30% w/w, 1% to 20% w/w, 5% to 15% w/w, or 8% to 10% w/w porous excipient, based on the weight of the pre-loaded porous excipient and the total weight of the composition.

In some embodiments, the active agent is loaded onto the porous excipient in an amount of from about 1% w/w to about 70% w/w, including from about 5% w/w to about 40% w/w, about 10% w/w to about 30% w/w, and about 15% w/w to about 25% w/w, based on the total weight of the loaded porous excipient, and amounts between any of these values, including 1% w/w, 5% w/w, 10% w/w, 15% w/w, 20% w/w, 25% w/w, 30% w/w, 35% w/w, 40% w/w, 45% w/w, 50% w/w, 55% w/w, 60% w/w or 70% w/w.

In some embodiments, the weight ratio of porous excipient to active agent is from about 1:1 to about 10:1, such as about 1:1 to about 5:1. In some embodiments, the weight ratio of porous excipient to active agent is from 1:1 to 10:1, such as 1:1 to 5:1. In some embodiments, the weight ratio of porous excipient to active agent is about 1:1, about 2:1, about 3:1, about 4:1, or about 5:1. In some embodiments, the weight ratio of porous excipient to active agent is 1:1, 2:1, 3:1, 4:1, or 5:1.

In some embodiments, the porous excipient may be selected and/or prepared to modify the release properties of the active agent from the composition, e.g., the porous excipient may be selected and/or prepared to exhibit active agent release-modifying properties. For example, the porous excipient may be selected and/or prepared to provide delayed release of the active agent, and/or to control release of the active agent, such as to provide release of the active agent at a predetermined rate and/or to maintain a constant therapeutic level of active agent for a specified period of time, or to provide any other type of controlled release. In some embodiments, the porous excipient allows control over active agent release (even a bi-phasic release is feasible), e.g., by change in pore size and shape of the excipient and/or by functionalization of the internal or external interfaces, or both. Martinez-Carmona et al., *Nanomaterials*, 5: 1906-1937 (2015), which is incorporated herein by reference, and Vallet-Regi et al., BIOMEDICAL APPLICATIONS OF MESOPOROUS CERAMICS: DRUG DELIVERY, SMART MATERIALS AND BONE TISSUE ENGINEERING (2013), sets forth examples for how to modify release characteristics of a composition.

Exemplary release-modifying considerations are discussed in Martinez-Carmona et al., *Nanomaterials*, 5: 1906-1937 (2015), which is incorporated herein by reference, and Vallet-Regi et al., BIOMEDICAL APPLICATIONS OF MESOPOROUS CERAMICS: DRUG DELIVERY, SMART MATERIALS AND BONE TISSUE ENGINEERING (2013), which is incorporated herein by reference.

In some embodiments, the surface of the porous excipient—including the inner pore surface—can be functionalized to bind active agent and/or control release of the active agent after a certain amount of time or in response to a stimulus. For instance, in exemplary embodiments a hormone (e.g., testosterone) bound to a porous excipient can be a ligand for site-specific delivery of agents to androgen-receptor (AR) positive sites, such as AR-positive tumors or other organs like the prostate, brain, or testis. In some embodiments, the porous excipient can be functionalized to promote cellular uptake through endocytosis. In some embodiments, active agent is released from the porous excipient after cellular uptake of the porous excipient. In some embodiments, the porous excipient is functionalized with one or more organic moieties. In some embodiments, the porous excipient is functionalized with amine groups, quaternary alkyl amines, alkyl chains, alkoxysilanes, fluoenylmethoxycarbonyl-modified organosilanes, hydrophobic groups, mercaptopropyl groups, aminopropyl groups, hydroxypropyl groups, phenyl groups, or combinations of two or more thereof. Exemplary functionalization groups are set forth in Vallet-Regi et al., BIOMEDICAL APPLICATIONS OF MESOPOROUS CERAMICS: DRUG DELIVERY, SMART MATERIALS AND BONE TISSUE ENGINEERING (2013), which is incorporated herein by reference.

The porous excipient may serve one or more functions in the context of the compositions described herein. For example, the porous excipient may serve as a carrier for the active agent, may protect the active agent, and/or may delay and/or control release of the active agent. Additionally or alternatively, the porous excipient may impact the chemical, physical, physico-chemical, and/or pharmacokinetic properties of the composition, as discussed in more detail below.

In some embodiments, the porous excipient acts as a protecting agent, i.e., it protects the active agent from oxidation and/or degradation and/or reaction with other components of the composition and/or environment. This can be particularly advantageous for active agents prone to oxidation and/or degradation, such as dopamine.

In some embodiments, the porous excipient impacts the chemical, physical, physico-chemical and/or pharmacokinetic properties of the composition, such as by acting as a gelling agent, a structure-giving agent, a solubilizing agent (e.g., a solubility enhancer), a release-modifying agent, and/or a binding site of an active agent.

Without being bound by theory, it is believed that in some embodiments the active agent is loaded onto the porous excipient in a stable amorphous state, such that a supersaturated aqueous solution can be provided at an application site, which can give rise to enhanced transepithelial or transmucosal transport. Also without being bound by theory, it is believed that the number of hydroxyl groups on the porous excipient available to form inter- and intra-molecular hydrogen bonding in compositions as claimed enhance dissolution.

In some embodiments, the porous excipient comprises porous particles (such as but not limited to ordered mesoporous silica, or SYLOID® particles such as AL-1FP, 244FP, XDP3050, 72FP, XDP6035, or XDP3150) that can be loaded with an active agent. Some embodiments comprises spray dried particles with active agent loaded onto porous excipient particles. In some embodiments, the loaded particles are in a dry powder form. In some embodiments, the particles are in a granulated form.

In addition to or as alternatives to selecting and/or preparing the porous excipient and/or any coating to provide a desired release profile for the active agent, the composition as a whole may be formulated to provide a desired release profile, e.g., a desired delayed and/or controlled release profile. For example, release of the active agent from the composition can be modified by varying one or more of the amount of active agent-loaded porous excipient in the composition, the amount of active agent present in any coating, the amount of active agent present in the vehicle of the composition, and/or by including one or more release-modifying agents in composition.

In some embodiments, the compositions have one or more of the following advantages as compared to compositions without an active agent loaded onto a porous excipient: a reduction of the amount of solidifying excipients; improved bioavailability; low or no toxicity potential; rapid onset of action; suitability for relatively high active agent payloads; potential for sustained-release depot; more control over active agent release (even a bi-phasic release is feasible), e.g., by change in pore size and shape of the excipient and by functionalization of the internal or external interfaces, or both; no suspension-related problems such as Ostwald ripening or concerns with regard to uniformity (i.e., segregation); ability to possess therapeutic efficacy at variable sizes of porous excipient particles; lipophilic or hydrophilic active agents, or even both, can be incorporated into the composition; the composition is suitable for allergic patients, e.g., because the composition can lack excipients that induce an allergic response; a simple and economical manufacturing process; protection of active agents sensitive to oxygen or humidity; stabilization of the amorphous form of active ingredient; no re-crystallization of the active ingredients; an option to provide fast release of the active ingredient; ability to target systemic circulation and/or the brain and/or the spinal cord by functionalization of the excipient; the composition can be spreadable (and thus remove concerns related to propelling the active agent into a specific site of the nasal cavity and to head position, spray angle, and plume geometry); and maximal nasal mucosal surface can be covered.

Coating

In some embodiments, the porous excipient comprises a coating. In some embodiments, the coating is porous, while in other embodiments the coating is nonporous. In some embodiments, the coating surrounds the porous excipient onto which active agent is loaded (e.g., provides a shell around the loaded porous excipient). In some embodiments, the coating is in the form of a film. In some embodiments, the coating functions to cap loaded pores. In some embodiments, the coating functions to cap the pores but does not completely surround the porous excipient (e.g., the pores are capped, but a shell is not formed completely around the porous excipient).

In some embodiments, the coating provides delayed release of an active agent. In some embodiments, the coating allows sustained release of an active agent. In some embodiments, the coating functions to improve bioavailability of the active agent. In some embodiments, the coating functions to protect the active agent loaded onto the porous excipient. In some embodiments, the coating contains an active agent (e.g., the same active agent as contained in the pores or a different one).

The coating may be comprised of any material suitable for use in a nasal pharmaceutical composition. In some embodiments, the coating comprises one or more polymers, which may be selected to provide desired characteristics to the coating (e.g., delayed release, controlled release, protection, etc.). In some embodiments, the coating comprises polymers that are soluble in oil or partially soluble in oil, while in other embodiments the coating comprises polymers that are poorly soluble in oil or insoluble in oil.

In any coating embodiments, the coating may comprise linear polymers, such as polyvinylpyrrolidone, hyaluronic acid, xanthan, alginate, polyvinyl acetate, sodium starch glycolate, and combinations or copolymers of any two or more thereof. In any coating embodiments, the coating may comprise branched polymers, such as branched polyethylene glycol or acacia gum. Additionally or alternatively, the coating may comprise cellulose-containing polymers, such as sodium carboxymethylcellulose. Additionally or alternatively, the coating may comprise copolymers, such as polyvinylpyrrolidone/polyvinyl acetate, polyvinylpyrrolidone/polyvinyl alcohol, polyvinyl alcohol/PEG, polyvinyl caprolactam/polyvinyl acetate/polyethylene glycol, and combinations of any two or more thereof. Additionally or alternatively, the coating may comprise cross-linked polyvinylpyrrolidone and/or cross-linked sodium carboxymethylcellulose. Additionally or alternatively, the coating may comprise a polylactide, such as polylactic acid. Any suitable polylactide can be used, such as a polylactide that comprises RESOMER® 202H, RESOMER® 202S, Lupon DEPOR®, PLENAXIS®, and combinations of any two or more thereof. Additionally or alternatively, the coating may comprise polysaccharides, such as chitosan (such as but not limited to chitosan 95/200). Additionally or alternatively, the coating may comprise peptides and/or proteins. Additionally or alternatively, the coating may comprise gelatin (such as but not limited to F15, F20, or F25). It will be understood that a coating may comprise combinations of any of two or more of the foregoing and/or chemical modifications of any of the foregoing.

In some embodiments, the coating further comprises an active agent (e.g., the active agent is loaded into or onto the coating), which may be the same or different from the active agent loaded onto the porous excipient. Thus, in some embodiments, the active agent is present in the pores of the porous excipient and also is present in the coating. In some embodiments, the coating does not contain an active agent.

In embodiments where the pores are capped, the coating can comprise materials, such as nanoparticles, covalently bound to pore entrances. Exemplary nanoparticles include cadmium sulfide (CdS) nanocrystals, $Fe_3O_4$ nanoparticles, and cyclodextrins. Without being bound by theory, it is believed that capping loaded pores can inhibit or control release of active agent from the pores.

Thus, in some embodiments the composition comprises loaded porous excipient that comprises active agent loaded onto porous excipient particles (such as but not limited to ordered mesoporous silica, or SYLOID® particles such as 244FP, XDP3050, 72FP, XDP6035, or XDP3150), where the particles are coated with material described herein (such as but not limited to gelatin). In some embodiments coated particles with active agent loaded onto porous excipient particles are spray dried, such as to obtain a dry powder form.

Additional Components

As noted above, the nasal compositions described herein may comprise, in addition to active agent and porous excipient, a vehicle and a viscosity-regulating (e.g., gelling) agent.

The vehicle may be any vehicle suitable as a vehicle for a nasal pharmaceutical composition. In some embodiments, the vehicle for the porous excipient is a hydrophilic vehicle. In some embodiments, the vehicle is a lipophilic or partly lipophilic vehicle, such as a vehicle comprising one or more fats, oils, waxes, phospholipids, steroids (e.g., cholesterol), sphingolipids, ceramides, sphingosines, prostaglandins, and/or fat-oil vitamins. In some embodiments, the vehicle comprises an oil or a mixture of oils, such as vegetable oil, castor oil, hydrogenated castor oil, soybean oil, sesame oil, or peanut oil; fatty acid esters, such as ethyl- and oleyl-oleate, isopropylmyristate; medium chain triglycerides; glycerol esters of fatty acids; polyethylene glycol; phospholipids; white soft paraffin; or combinations of any two or more thereof.

The vehicle may be present in any suitable amount, such as an amount effective to provide desired properties for nasal administration, desired physical properties, desired release properties, desired pharmacokinetics, etc. In some embodiments, the composition comprises a vehicle in an amount of from about 15% to about 98% by weight, about 30 to about 98% by weight, about 50% to about 95% by weight, about 75% to about 95% by weight, about 80%, or about 90% by weight, based on the total weight of the composition. In some embodiments, the composition comprises a vehicle in an amount of from 15% to 98% by weight, 30 to 98% by weight, 50% to 95% by weight, 75% to 95% by weight, 80%, or 90% by weight, based on the total weight of the composition.

In some embodiments, the vehicle comprises an active agent, such as comprising active agent dissolved, suspended or dispersed in the vehicle. The active agent(s) in the vehicle can be the same as or different from the active agent(s) loaded onto the porous excipient.

The viscosity-regulating agent, if present, may be any viscosity-regulating agent suitable for use as a viscosity-regulating agent in a nasal pharmaceutical composition. In some embodiments, the viscosity-regulating agent comprises mesoporous silica (which may be loaded with active agent or unloaded). In some embodiments, the viscosity-regulating agent comprises cellulose, cellulose-containing substances, polysaccharides, carbomers, polyvinyl alcohol, povidone, colloidal silicon dioxide, cetyl alcohols, stearic acid, beeswax, petrolatum, triglycerides, lanolin, or combinations of any two or more thereof. In some embodiments, the viscosity-regulating agent comprises colloidal silicon dioxide (such as but not limited to AEROSIL® 200 (Evonik) and/or CAB-O-SIL® M5 (Cabot)). In some embodiments, the viscosity-regulating agent comprises synthetic silica, such as SYLODENT® (precipitated silica with a compacted bulk density of about 110 $kg/m^3$, a specific surface area of about 190 $m^2/g$, and an average particle size of about 18 μm) or SYLOBLANC® silicas (porous silica gel with a pore volume of about 1.6 ml/g and an average particle size of about 3 μm) from W.R. Grace & Co. In some embodiments, the viscosity-regulating agent comprises hydrophilic fumed silica, such as AEROSIL® 200 and/or lipophilic silicon dioxide, such as AEROSIL® R972 (which is fumed silica aftertreated with dimethyldichlorosilane, and which has a surface area of about 90 to about 130 $m^2/g$). Without being bound by theory, it is believed that hydrophilic fumed silica can be used to prepare a thixotropic gel composition with a high temperature stability as compared to a comparable gel produced with other viscosity-regulating agents.

The viscosity-regulating agent, if present, may be present in an amount effective to adjust the viscosity of the composition to the desired level. In some embodiments, the composition comprises from about 0.5 to about 20% by weight, about 0.5 to about 10% by weight, about 0.5 to about 7% by weight, about 1 to about 4% by weight, about 4% by weight, or about 2% by weight viscosity-regulating agent, based on the total weight of the composition. In some embodiments, the composition comprises from 0.5 to 20% by weight, 0.5 to 10% by weight, 0.5 to 7% by weight, 1 to 4% by weight, 4% by weight, or 2% by weight viscosity-regulating agent, based on the total weight of the composition.

In some embodiments, the composition has a viscosity as measured by a rotating viscometer of about 2,000 mPa·sec to about 10,000 mPa·sec, such as about 2,000 mPa·sec, about 3,000 mPa·sec, about 4,000 mPa·sec, about 5,000 mPa·sec, about 6,000 mPa·sec, about 7,000 mPa·sec, about 8,000 mPa·sec, about 9,000 mPa·sec, or about 10,000 mPa·sec. In some embodiments, the composition has a viscosity as measured by a rotating viscometer of 2,000 mPa·sec to 10,000 mPa·sec, such as 2,000 mPa·sec, 3,000 mPa·sec, 4,000 mPa·sec, 5,000 mPa·sec, 6,000 mPa·sec, 7,000 mPa·sec, 8,000 mPa·sec, 9,000 mPa·sec, or 10,000 mPa·sec.

In some embodiments, the porous excipient functions as the only viscosity-regulating agent in the composition. Thus, in some embodiments the composition does not include a viscosity-regulating agent other than the porous excipient. For example, porous excipient having silanol groups (such as but not limited to mesoporous silica such as SYLOID®) can function as a viscosity-regulating agent. In some embodiments, the porous excipient has isolated, germinal, and/or vicinal silanol groups. Even if the porous excipient comprises silanol groups, another viscosity-regulating agent may or may not be added to the composition.

The composition may or may not contain other components suitable for use a nasal pharmaceutical composition. For example, in some embodiments, the composition may independently comprise one or more of: a solubilization agent; a cosolvent; a charge modifying agent; a pH control agent; an osmotic adjusting agent; a degradative enzyme inhibitor; an antioxidant; a stabilizer; a membrane penetration-enhancing agent; an emulsifying agent; a wetting agent; a suspending agent; a surfactant; an adhesive; and/or a taste-masking agent. In some embodiments, the composition independently does not contain one or more of (i.e., one or more of the following are not present in the composition): a solubilization agent; a cosolvent, a charge modifying agent; a pH control agent; an osmotic adjusting agent; a degradative enzyme inhibitor; an antioxidant; a stabilizer; a membrane penetration-enhancing agent; an emulsifying agent; a wetting agent; a suspending agent; a surfactant; an adhesive; and a taste-masking agent. These components, if present, may be present in an amount effective to exhibit their intended functions and/or to confer desired properties to the composition. In some embodiments, the porous excipient is the only excipient in the composition.

The surfactant, if present, may be any surfactant suitable for use as a surfactant in a nasal pharmaceutical composition. In some embodiments, the surfactant is selected from anionic, cationic, amphoteric, and non-ionic surfactants, including, but not limited to, lecithin, fatty acid esters of polyvalent alcohols, fatty acid esters of sorbitanes, fatty acid esters of polyoxyethylensorbitans, fatty acid esters of polyoxyethylene, fatty acid esters of sucrose, fatty acid esters of polyglycerol, oleoyl polyoxylglycerides (such as but not limited to apricot kernel oil PEG-6-esters), oleoyl macrogolglycerides, and/or humectants such as sorbitol, glycerine, polyethylene glycol, macrogol glycerol fatty acid ester, and combinations of any two or more thereof. In some embodiments, the surfactant comprises an oleoyl macrogolglyceride (such as LABRAFIL® M 1944 CS (Gattefosse, Saint-Priest, France)) or a mixture of oleoyl macrogolglycerides.

The surfactant, if present, may be present in an amount effective to exert surfactant properties. In some embodiments, the composition comprises from about 1 to about 20% by weight, about 1 to about 10% by weight, about 1 to about 5% by weight, about 4% by weight, or about 2% by weight surfactant, based on the total weight of the composition. In some embodiments, the composition comprises from 1 to 20% by weight, 1 to 10% by weight, 1 to 5% by weight, 4% by weight, or 2% by weight surfactant, based on the total weight of the composition.

In some exemplary embodiments, the composition comprises (a) from about 0.5% to about 50% w/w of a mesoporous silica excipient, based on the weight of the composition; (b) from about 0.5% to about 40% w/w of active agent, based on the weight of the composition, wherein the active agent is loaded onto a surface of the mesoporous silica located inside pores of the mesoporous silica; (c) from about 50% to about 90% w/w of castor oil, based on the weight of the composition; and (d) from about 0.5% to about 20% w/w of colloidal silicon dioxide, based on the weight of the composition.

In some exemplary embodiments, the composition comprises (a) from about 0.5% to about 50% w/w of a mesoporous silica excipient, based on the weight of the composition; (b) from about 0.5% to about 40% w/w of active agent, based on the weight of the composition, wherein the active agent is loaded onto a surface of the mesoporous silica located inside pores of the mesoporous silica; (c) from about 50% to about 90% w/w of castor oil, based on the weight of the composition; and (d) from about 2% to about 6% w/w of oleoyl macrogolglycerides, based on the weight of the composition.

In some exemplary embodiments, the composition comprises (a) from about 6% to about 11% w/w of a mesoporous silica excipient, based on the weight of the composition; (b) from about 0.1% to about 30% w/w of active agent, based on the weight of the composition, wherein the active agent is loaded onto a surface of the mesoporous silica located inside pores of the mesoporous silica; and (c) from about 70% to about 80% w/w of castor oil, based on the weight of the composition. In some exemplary embodiments, the composition comprises from about 0.5% to about 20% of a viscosity regulating agent, based on the weight of the composition.

In some exemplary embodiments, the composition comprises (a) about 8% w/w of a mesoporous silica excipient, based on the weight of the composition; (b) about 2% w/w of active agent, based on the weight of the composition, wherein the active agent is loaded onto a surface of the mesoporous silica located inside pores of the mesoporous silica; (b) about 80% w/w of castor oil, based on the weight of the composition; and (c) about 10% w/w of colloidal silicon dioxide, based on the weight of the composition.

In some exemplary embodiments, the compositions comprises (a) a nasal gel containing from about 1% to about 50% w/w of mesoporous silica unloaded and/or loaded with an active agent based on the weight of the composition and (b) additional excipients up to 100% w/w of the weight of the composition.

Methods of Manufacturing

Also provided herein are methods of making nasal pharmaceutical compositions comprising a porous excipient and an active agent, wherein the active agent is loaded onto a surface of the porous excipient located inside pores of the porous excipient.

In some embodiments, the active agent is loaded onto the porous excipient via one or more processes selected from fluid bed impregnation, spontaneous evaporation and sublimation, spray drying, vacuum drying, hot-melt extrusion, spay congealing, co-milling, wet impregnation/solvent deposition, electrospraying technology, hybridization technology, emulsion polymerization, sol-gel encapsulation, chemically linking, coacervation, and sol-gel processes.

In some embodiments, the active agent is loaded onto the porous excipient via oil adsorption. In specific embodiments, the porous excipient is mixed with an active agent dissolved in oil, such as any one or more of plant oils, animal oils, and mineral oils. Exemplary oils include vegetable oil, castor oil, hydrogenated castor oil, soybean oil, sesame oil, peanut oil, linalool, TRANSCUTOL® HP (purified diethylene glycol monoethyl ether EP/NF from Gattefosse), CAPRYOL™ PGMC (propylene glycol monocaprylate (type I) NF from Gattefosse), and combinations of any two or more thereof. In some embodiments, the oil (with dissolved active agent) and porous excipient are mixed at a volume ratio of less than about 3:1 oil:excipient, such as about 2.5:1 oil:excipient, about 2:1 oil:excipient, about 1.5:1 oil:excipient, or about 1:1 oil:excipient. In some embodiments, the oil (with dissolved active agent) and porous excipient are mixed at a volume ratio of less than 3:1 oil:excipient, such as 2.5:1 oil:excipient, 2:1 oil:excipient, 1.5:1 oil:excipient, or 1:1 oil:excipient. In some embodiments, the oil and porous excipient are mixed at a ratio of about 10:1 oil:excipient, such as about 8:1 or about 5:1 oil:excipient. In some embodiments, the oil and porous excipient are mixed at a ratio of 10:1 oil:excipient, such as 8:1 or 5:1 oil:excipient.

In some embodiments, the active agent is loaded onto the porous excipient via a solvent, such as one or more of methylene chloride, dichloromethane, acetone, water, and ethanol. In specific embodiments, the porous excipient is mixed with an active agent dissolved in a solvent, such as an ethanol:water mixture. In some embodiments, the active agent is dissolved in an ethanol:water mixture comprising about 30:70 (v/v), about 40:60 (v/v), about 45:55 (v/v), about 50:50 (v/v), about 55:45 (v/v), about 60:40 (v/v), or about 70:30 (v/v) ethanol:water. Without being bound by theory, it is believed that ethanol:water ratios can be further varied based on the active agent used and its solubility in ethanol.

In some embodiments, a release-modifying agent is used to facilitate loading of the active agent onto the porous excipient. In some embodiments, the release-modifying agent, or a solution comprising the release-modifying agent, is added to the active agent mixture (e.g., the oil or solvent comprising the active agent), and then the active agent is loaded onto the porous excipient. The release-modifying agent, if used, may be any release-modifying agent suitable for use in loading an active agent onto a porous excipient. In some embodiments, the release-modifying agent comprises polyvinylpyrrolidone (such as but not limited to PVP K25® from Ashland, Inc., which has a molecular weight of about 24,000 Da), cellulose ethers, hyaluronic acid, polyvinyl Acetate (PVAc), polyvinyl alcohol (PVA), sodium starch glycolate, polylactide, polysaccharides, solubilizers (such as but not limited to polyethylene glycol (PEG) or tween), or combinations of two or more thereof.

In some embodiments, a solution comprising the release-modifying agent comprises the release-modifying agent mixed in an oil (such as but not limited to one or more of and vegetable oil, castor oil, hydrogenated castor oil, soybean oil, sesame oil, peanut oil, linalool, TRANSCUTOL® HP (purified diethylene glycol monoethyl ether EP/NF from Gattefosse), CAPRYOL™ PGMC (propylene glycol monocaprylate (type I) NF from Gattefosse)) or a solvent (such as but not limited to one or more of methylene chloride, dichloromethane, acetone, water, and ethanol). In some embodiments, the solution comprises about 0.01%, about 0.05%, about 0.1%, about 0.5%, 1%, about 2%, about 2.5%, about 3%, about 5%, about 10%, about 20%, or about 30% w/w release-modifying agent, such as 0.01%, 0.05%, 0.1%, 0.5%, 1%, 2%, 2.5%, 30%, 5%, 10%, 20%, or 30% w/w release-modifying agent. In some embodiments, the release-modifying agent solution is added to the active agent mixture in an amount of about 0.01%, about 0.05%, about 0.1%, about 0.5%, about 1%, about 2%, about 2.5%, about 3%, about 5%, or about 10%, such as 0.01%, 0.05%, 0.1%, 0.5%, 1%, 2%, 2.5%, 3%, 5%, or 10%.

In some embodiments, active agent is loaded onto porous excipient with a high loading efficiency. In some embodiments, at least about 60% of the active agent used in the process is loaded onto the porous excipient. In some embodiments, an active agent is loaded onto a porous excipient with a loading efficiency of at least about 60%, at least about 70%, at least about 75%, at least about 80%, at least about 85%, at least about 90%, at least about 95%, or about 100%, including about 60%, about 70%, about 75%, about 80%, about 85%, about 90%, about 95%, or about 100%. In some embodiments, an active agent is loaded onto a porous excipient with a loading efficiency of at least 60%, at least 70%, at least 75%, at least 80%, at least 85%, at least 90%, at least 95%, or 100%, including 60%, 70%, 75%, 80%, 85%, 90%, 95%, or 100%. In some embodiments, the active agent is loaded onto a porous excipient with an efficiency of at least about 95% or at least 95%.

In some embodiments, the active agent is loaded onto a surface of the porous excipient located inside the pores of the porous excipient. In some embodiments, loaded onto a surface of the porous excipient located inside the pores of the porous excipient, but is not loaded onto the external surface of the porous excipient.

Some embodiments comprise completely or partly exchanging a gelling agent (such as but not limited to fumed silica) against a porous excipient adsorbate (such as but not limited to porous silica adsorbate). In some embodiments, the active agent is loaded onto the porous excipient through interactions with active agents otherwise loaded onto the excipient, for instance through capillary forces and/or Van der Waals interactions (e.g., through interactions with active agent molecules already loaded on the porous excipient). In some embodiments, the active agent is loaded onto the porous excipient through interactions with silanol groups on the surface of the porous excipient. Without being bound by theory, it is believed that in some embodiments (e.g., embodiments with a polar active agent) active agent interacting with the silanol groups will be displaced and released from the porous excipient upon contact with highly polar substances such as body fluids.

In some embodiments, active agent is adsorbed to the porous excipient. In some embodiments, active agent is covalently bound to the porous excipient via functional groups on the porous excipient. Without being bound by theory, it is believed that covalently bound active agent can be released in response to a stimulus, such as a change in pH, temperature, presence of enzymes, etc.

In some embodiments, the porous excipient is synthesized from a precursor, such as tetraethyl orthosilicate or (3-mercaptopropyl)trimethoxysilane.

In some embodiments, compositions can be prepared without formulating a thermodynamically critical suspension.

In some embodiments, the compositions are prepared using sterile materials. In some embodiments, compositions are prepared under sterile conditions.

In some embodiments, the active agent and porous excipient are independently dissolved in an oil and/or solvent (such as ethanol, water, methylene chloride, dichloromethane, acetone, or combinations of two or more thereof) and mixed together. In some embodiments, the active agent and the porous excipient are mixed in a stepwise manner, such as by adding the active agent via pump to a stirred porous excipient. In some embodiments, the resultant mixture is dried under vacuum (such as but not limited to at a temperature from about 50° C. to about 80° C.). In other embodiments, the resultant solution is spray dried to obtain porous excipient loaded with active agent. In some embodiments, the mixture is homogenized before spray drying. In some embodiments, the spray dried particles are spray dried a second time after mixing them with a second solution with dissolved active agent.

In some embodiments, the active agent is dissolved in a solvent, and then the porous excipient is mixed into the solvent. In some embodiments, the active agent and the porous excipient are mixed in a stepwise manner, such as by adding the active agent via pump to a stirred porous excipient. In some embodiments, the resultant mixture is dried under vacuum (such as but not limited to at a temperature of from about 50° C. to about 80° C.). In other embodiments, the resultant mixture is spray dried. In some embodiments, the resultant mixture is spray dried after the active agent has been completely introduced into the porous excipient (e.g., after a maximum amount of active agent is loaded onto the porous excipient).

In some embodiments, the loaded porous excipient is mixed with additional components, such as a vehicle, a surfactant (such as but not limited to an emulsifying agent), unloaded active agent, and a viscosity-reducing agent prior to spray drying. For instance, in some embodiments the loaded porous excipient is mixed with an emulsifying agent. The emulsifying agent, if present, may be any emulsifying agent suitable for use as an emulsifying agent in a nasal pharmaceutical composition. In some embodiments, the emulsifying agent comprises sodium oleate, TWEEN® 20, Natriumoleat, LUTROL® F68, or combinations of any two or more thereof. The emulsifying agent, if present, may be present in an amount effective to emulsify components of the composition. In some embodiments, the compositions comprise from about 0.01% w/w to about 2% w/w, from about 0.02% w/w to about 1% w/w, about 0.03% w/w, about 0.04% w/w, or about 0.08% w/w emulsifying agent, based on the total weight of the mixture. In some embodiments, the compositions comprise from 0.01% w/w to 2% w/w, from 0.02% w/w to 1% w/w, 0.03% w/w, 0.04% w/w, or 0.08% w/w emulsifying agent, based on the total weight of the mixture.

In some embodiments, the methods result in a yield of greater than 25%, such as from about 25% to about 100%, from about 50% to about 99%, about 60% to about 98%, about 70% to about 95%, about 50%, about 60%, about 70%, about 80%, about 90%, about 95%, about 98%, or about 99%. In some embodiments, the methods result in a yield of from 25% to 100%, from 50% to 99%, 60% to 98%, 70% to 95%, 50%, 60%, 70%, 80%, 90%, 95%, 98%, or 99%.

In some embodiments, a coating is added to the loaded porous excipient. In some embodiments, the material used to prepare the coating is dissolved in a solvent, and then a loaded porous excipient is added to the solution. In some embodiments, active agent and the coating material are independently dissolved in an oil and/or solvent (such as ethanol, water, methylene chloride, dichloromethane, acetone, or combinations of two or more thereof), mixed together, and then a loaded porous excipient is added to the resultant solution. The solution with both loaded porous excipient and coating material can then be spray dried. In some embodiments, the coating material and loaded porous excipient are spray dried together without being mixed together first.

In some embodiments, the porous excipient loaded with active agent is coated as described above via spray-drying or co-processing together with a coating substance (e.g., polymers insoluble in oil or other substances described above). In some embodiments, the loaded porous excipient and coating substance are spray dried in a one-phase system. In some embodiments, the loaded porous excipient and coating material are spray-dried in an emulsion. In some embodiments, the coated porous excipient loaded with active agent is mixed with additional components, such as a vehicle, a surfactant, unloaded active agent, and a viscosity-enhancing agent.

As discussed above, in some embodiments the loaded pores are capped, for example, to inhibit or control release of the active agent from the pores. The pores can be capped by any suitable method, such as by covalently bonding nanocrystals (such as but not limited to cadmium sulfide nanocrystals) to the pore entrances. Exemplary methods of pore-capping are discussed in Lai et al, *J. Am. Soc. Chem.* 125(15): 4451-4459 (2003) and Sun, "Mesoporous silica nanoparticles for applications in drug delivery and catalysis," *Graduate Theses and Dissertations*, Paper 12812 (2012), both of which are incorporated herein by reference.

Methods of Using

Also provided herein are methods for intranasal delivery of an active agent to a subject in need thereof. In some embodiments, a composition as described herein comprising a therapeutically effective amount of an active agent is nasally administered to a subject in need thereof, such as by applying an amount of the composition to the nasal cavity or administering an amount of the composition into the nasal cavity. The composition may be administered from any device suitable for administering nasal compositions, such as a multi-dose device or a single-dose device.

In some embodiments, the compositions achieve therapeutic levels of the active agent in blood and/or brain for up to 2 hours post-administration, up to 3 hours post-administration, up to 4 hours post-administration, up to 5 hours post-administration, or up to 6 hours post-administration. In some embodiments, the compositions achieve therapeutic levels in the blood and/or brain for 6 hours or more.

Conditions that can be treated using compositions described herein depend on the active agent(s) formulated in the composition. Intranasal delivery may be particularly useful for treating disorders of the central nervous system (such as but not limited to spina bifida), disorders of the brain, and/or disorders of the spinal cord. In some embodiments, compositions described herein are useful in methods of treating neurological or psychiatric disorders. In some embodiments, compositions described herein are useful in methods of treating: diseases caused by faulty genes, such as Huntington's disease or muscular dystrophy; degenerative diseases, such as Parkinson's disease or Alzheimer's disease; diseases related to blood vessels, such as stroke; injuries to the spinal cord and/or brain; seizure disorders, such as epilepsy; cancer, such as brain tumors; and infections, such as meningitis.

In specific embodiments, compositions described herein comprising testosterone are useful in methods of treating hypogonadism (such as primary hypogonadism or secondary hypogonadism), female sexual dysfunction, female arousal disorder, anorgasmia, or hypoactive sexual desire disorder, Multiple sclerosis (MS). In specific embodiments, compositions described herein comprising progesterone are useful in methods of treating insomnia and brain injuries. In specific embodiments, compositions described herein comprising aripiprazol, auetiapin, or paliperidon are useful in methods of treating schizophrenia. In specific embodiments, compositions described herein comprising duloxetine or dopamine are useful in methods of treating depression and/or anxiety. In specific embodiments, compositions described herein comprising testosterone, glatirameracetat, interferon beta-1a, interferon beta-1b, fingolimod, natalizumab, or dimethylfumarat are useful in methods of treating multiple sclerosis. In specific embodiments, compositions described herein comprising pregnenolone, memantine, rivastigmin, or donepezil are useful in methods of enhancing memory or treating Alzheimer's disease. In specific embodiments, compositions described herein comprising desvenlafaxine, duloxetine, or dopamine are useful in methods of treating depression. In specific embodiments, compositions described herein comprising eszopiclone or eszopiclone are useful in methods of treating insomnia. In specific embodiments, compositions described herein comprising tomoxetin, guanfacine, methylphenidate, lisdexamfetamine, or dopamine are useful in methods of treating attention deficit hyperactive disorder. In specific embodiments, compositions described herein comprising progesterone or recombinant tissue plasminogen activator (rt-PA) are useful in methods of treating traumatic brain injury. In specific embodiments, compositions described herein comprising methotrexate, raltitrexed, 5-fluorouracil, telomerase inhibitor, or monoclonal antibodies are useful in methods of treating a brain tumor. In specific embodiments, compositions described herein comprising midazolam, lacosamide, levetiracetam, lamotrigine, or valproic acid are useful in methods of treating epilepsy. In specific embodiments, compositions described herein comprising oxycodone, pregabalin, buprenorphine, hydrocodone, or fentanyl are useful in methods of treating pain. In specific embodiments, compositions described herein comprising safinamide, ropinirole, pramipexole, dopamine, L-DOPA, selegiline, cabergoline, or istradefylline are useful in methods of treating Parkinson's disease.

In some embodiments, compositions as described here can be used to vaccinate a subject. For example, compositions as described herein can be used to vaccinate a subject against influenza, hepatitis B, or meningitis.

The following examples are included as illustrative of the compositions described herein. These examples are in no way intended to limit the scope of the invention. Other aspects of the invention will be apparent to those skilled in the art to which the invention pertains.

EXAMPLES

Example 1—Testosterone-Loaded Beads: Loading Via Spray Drying

Spray dried testosterone-loaded beads were prepared using the following protocol.

First Spray Drying Step 90 ml of ethanol (abs.) were added to 1.0 g of mesoporous SYLOID® 244FP particles, and the resultant dispersion was homogenized with a magnetic stirrer operated at 500 rpm. Separately, 10 ml of ethanol (abs.) was added to 0.428 g of testosterone, and the testosterone was dissolved on vibrating shaker operated at 900 rpm. After the testosterone was dissolved, the testosterone solution was added to the particle dispersion, and the mixture was stirred for 20 hours at 500 rpm.

The mixture was then spray dried using a Mini Spray Dryer B-290 (Büchi) with a 0.7 mm diameter nozzle tip, which was operated in closed-loop mode with nitrogen as the dispersion gas (inert loop B-295). The instrument was run in sucking mode. During spray drying, the dispersion was stirred at 500 rpm. Spray drying parameters are set forth in Table 1A:

TABLE 1A

Spray-drying parameters for first spray-drying step in testosterone loading experiment

| Parameter | Setting | Flow rate |
| --- | --- | --- |
| Inlet temperature Tin (° C.) | 81 | — |
| Feed rate (%) | 10 | ~3.3 mL/min |
| Aspirator flow (%) | 100 | 35 m$^3$/h |
| Spray gas flow (rotameter) (mm) | 45 | 536 L/h |
| Nozzle Cleaner | 1 | — |

The spray dried particles were collected in a high efficiency cyclone, and then dried in a vacuum drying oven at 40° C. and 10 mbar for six days.

Second Spray Drying Step 0.250 g of testosterone were dissolved in 4 ml of ethanol using a vibrating shaker at 900 rpm. 1.000 g of gelatin F15 was dissolved in 55 ml of water using a thermo shaker operated at 200 rpm and 37° C. for two hours. The testosterone solution was added to the gelatin solution, and the mixture was stirred at 500 rpm. Then, 0.500 g of the previously spray dried particles (i.e., the testosterone/244FP particles) were added to the solution, and dispersed at 500 rpm. In some cases, the dispersion was homogenized further with sonication.

The dispersion was spray dried using a Mini Spray Dryer B-290 (Büchi) with a standard two-fluid nozzle with a 0.7 mm diameter nozzle tip, which was operated in closed-loop mode with nitrogen as the dispersion gas (inert loop B-295). The instrument was run in sucking mode. During spray drying, the dispersion was stirred at 500 rpm. Spray drying parameters are set forth in Table 1B.

TABLE 1B

Spray-drying parameters for second spray-drying step in testosterone loading experiment

| Parameter | Setting | Flow rate |
| --- | --- | --- |
| Inlet temperature Tin (° C.) | 135 | — |
| Feed rate (%) | 10 | ~3.3 mL/min |
| Aspirator flow (%) | 100 | 35 m$^3$/h |
| Spray gas flow (rotameter) (mm) | 45 | 536 L/h |
| Nozzle Cleaner | 1 | — |

The final testosterone-loaded particles were dried in a vacuum drying oven at 40° C. and 10 mbar. The particles have a theoretical loading of 22.9% testosterone.

Example 2—Testosterone-Loaded Particles: Free-Flowing Powder

A free-flowing powder of testosterone-loaded particles was prepared using the following protocol.

0.2143 g of testosterone were added to 1.5 g of linalool oil and then mixed using a vortex mixer for 10 minutes. Then, 0.5 g of SYLOID® particles (both 244FP and XDP3050 were used in independent experiments) were added to 0.75 g of the dissolved testosterone mixture, which was then stirred with a magnetic stirrer at 700 rpm for 10-15 minutes. The SYLOID®/testosterone mixture was then mixed with a spatula to reintroduce portions of the mixture adhered to the wall of the mixing container, and then stirred again with a magnetic stirrer for 10-15 minutes. The particles have a theoretical loading of about 7.5% testosterone.

Example 3—Testosterone-Loaded Particles: Free-Flowing Powder, Loading by Oil Adsorption Method Testosterone-loaded particles were prepared using the following protocol.

0.2143 g of testosterone was added to 1.5 g of linalool oil and then mixed using a vortex mixer for 10 minutes. Then, 0.5 g of SYLOID® particles (both 244FP and 72FP were used in independent experiments) were added to 1.5 g of the dissolved testosterone mixture, which was then stirred with a magnetic stirrer at 700 rpm for 10-15 minutes. The SYLOID®/testosterone mixture was then mixed with a spatula to reintroduce portions of the mixture adhered to the wall of the mixing container, and then stirred again for a magnetic stirrer for 10-15 minutes. The particles have a theoretical loading of about 9.4% testosterone.

Example 4—Progesterone-Loaded Beads: Loading Via Spray Drying

Spray dried progesterone-loaded beads were prepared using the following protocol.

60 ml of ethanol (abs.) were added to 1.0 g of mesoporous SYLOID® 244FP particles, and the resultant dispersion was homogenized with a magnetic stirrer operated at 500 rpm. Separately, 40 ml of ethanol (abs.) was added to 0.666 g of progesterone, and the progesterone was dissolved on a vibrating shaker operated at 900 rpm. After the progesterone was dissolved, the progesterone solution was added to the particle dispersion, and the mixture was stirred for 20 hours at 500 rpm.

The mixture was spray dried using a Mini Spray Dryer B-290 (Büchi) with a standard two-fluid nozzle with a 0.7 mm diameter nozzle tip, which was operated in closed-loop mode with nitrogen as the dispersion gas (inert loop B-295). The instrument was run in sucking mode. During spray drying, the dispersion was stirred at 500 rpm. Spray drying parameters are set forth in Table 2.

TABLE 2

Spray-drying parameters for progesterone loading experiment

| Parameter | Setting | Flow rate |
| --- | --- | --- |
| Inlet temperature Tin (° C.) | 81 | — |
| Feed rate (%) | 10 | ~3.3 mL/min |
| Aspirator flow (%) | 100 | 35 m³/h |
| Spray gas flow (rotameter) (mm) | 45 | 536 L/h |
| Nozzle Cleaner | 1 | — |

The spray dried particles were collected in a high efficiency cyclone, and then dried in a vacuum drying oven at 40° C. and 10 mbar for six days. The particles have a theoretical loading of about 40% progesterone.

Example 5—Loading of Progesterone

Spray dried progesterone particles were prepared using the protocol set forth in Example 4, but with component amounts varied to produce particles with theoretical loadings of 30%, 40%, 50%, and 60% progesterone. Yields were determined based on the mass of the composition after spray drying into a vial as compared to the combined mass of the progesterone and SYLOID® particles before spray drying. Residual moisture was calculated as a change in mass after vacuum drying the spray dried particles.

Progesterone compositions prepared with SYLOID® 72FP as set forth in Table 3A.

TABLE 3A

Spray dried compositions with progesterone + SYLOID ® 72FP.

| Batch | Amount of Progesterone | Theoretical Progesterone Loading (%) | Yield (%) | Residual Moisture (%) |
| --- | --- | --- | --- | --- |
| MetP_111 | 0.428 g | 30 | 76.8 | 4.0 |
| MetP_112 | 0.666 g | 40 | 73.6 | 3.1 |
| MetP_113 | 1 g | 50 | 75.6 | 2.6 |
| MetP_114 | 1.5 g | 60 | 74.4 | 1.8 |

Scanning electron micrographs of the progesterone+SYLOID® 72FP compositions, which are provided in FIG. 1, were obtained to examine the morphology and size of the particles. In the sub-figures on the left side of FIG. 1, the bar represents a 10 µm distance, and in the sub-figures on the right side of FIG. 1, the bar represents a 1 µm distance.

Spray dried particles were also prepared using a similar protocol, but with SYLOID® 244FP instead of SYLOID® 72FP. These compositions are set forth in Table 3B.

TABLE 3B

Spray dried compositions with progesterone + SYLOID ® 244FP.

| Batch | Amount of Progesterone | Theoretical Progesterone Loading (%) | Yield (%) | Residual Moisture (%) |
| --- | --- | --- | --- | --- |
| MetP_106 | 0.428 g | 30 | 58.5 | 3.1 |
| MetP_107 | 0.666 g | 40 | 67.9 | 2.6 |
| MetP_108 | 1 g | 50 | 68.0 | 2.4 |
| MetP_109 | 1.5 g | 60 | 72.1 | 1.8 |

Figure 2:
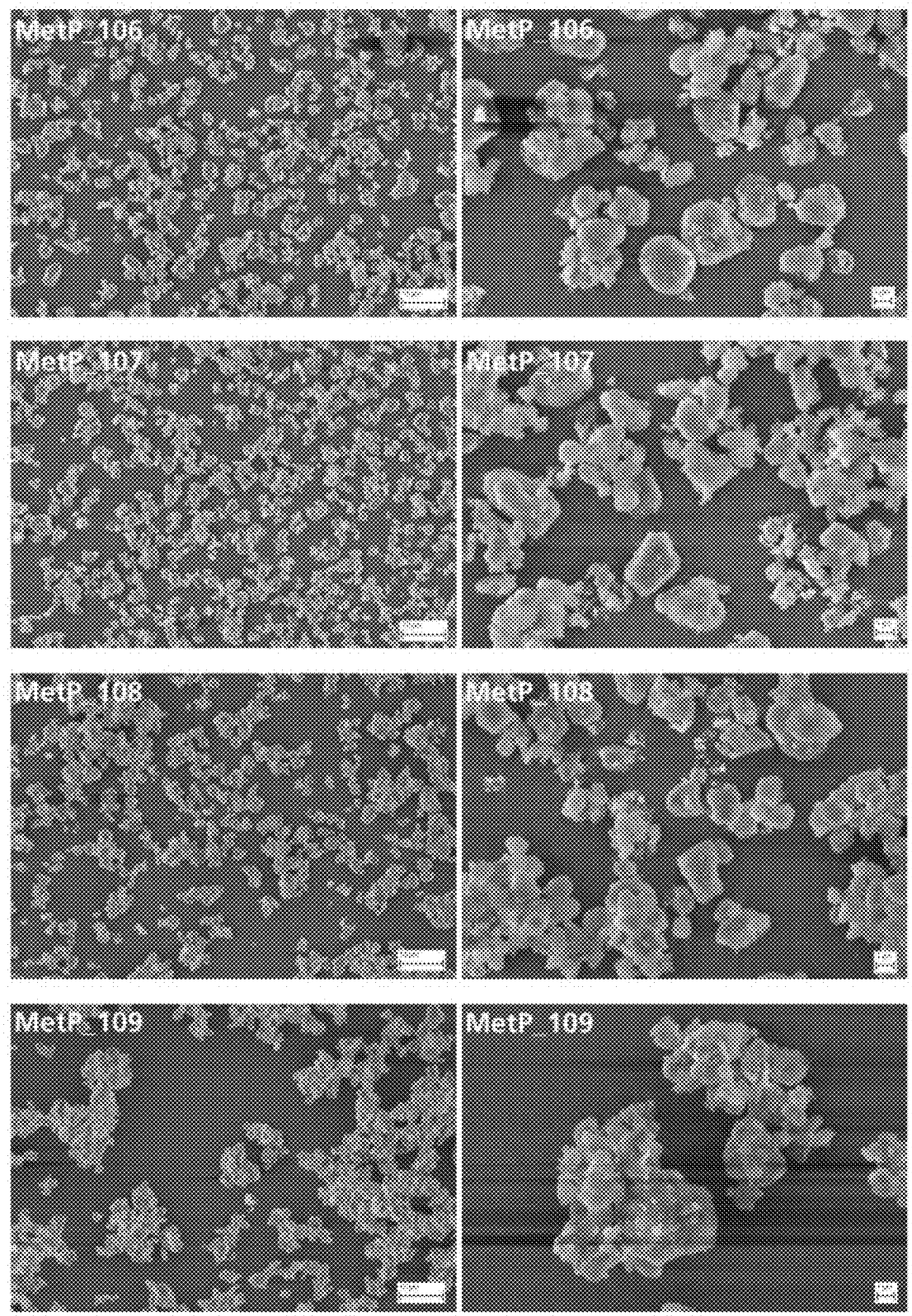
FIG. 2 shows scanning electron micrographs of various spray dried compositions as described herein with progesterone and SYLOID® 244FP particles.

Scanning electron micrographs of the progesterone+SYLOID® 244FP compositions, which are provided in FIG. 2, were obtained to examine the morphology and size of the particles. The scanning electron micrographs were taken at two separate focal lengths; in the sub-figures on the left side of FIG. 2, the bar represents a 10 µm distance, and in the sub-figures on the right side of FIG. 2, the bar represents a 1 µm distance.

For reference, compositions with SYLOID® 72FP or SYLOID® 244FP but without progesterone were prepared via spray drying. These compositions are set forth in FIG. 3C.

TABLE 3C

Spray dried reference compositions with SYLOID ® 72FP or SYLOID ® 244FP.

| Batch | Material | Amount of Material | Volume | $T_{in}$ (° C.) | Yield (%) |
| --- | --- | --- | --- | --- | --- |
| MetP_46 | SYLOID ® 244FP | 0.5 g | 50 ml | 110 | 60.1 |
| MetP_110 | SYLOID ® 72FP | 1 g | 100 ml | 81 | 91.2 |

Figure 3:
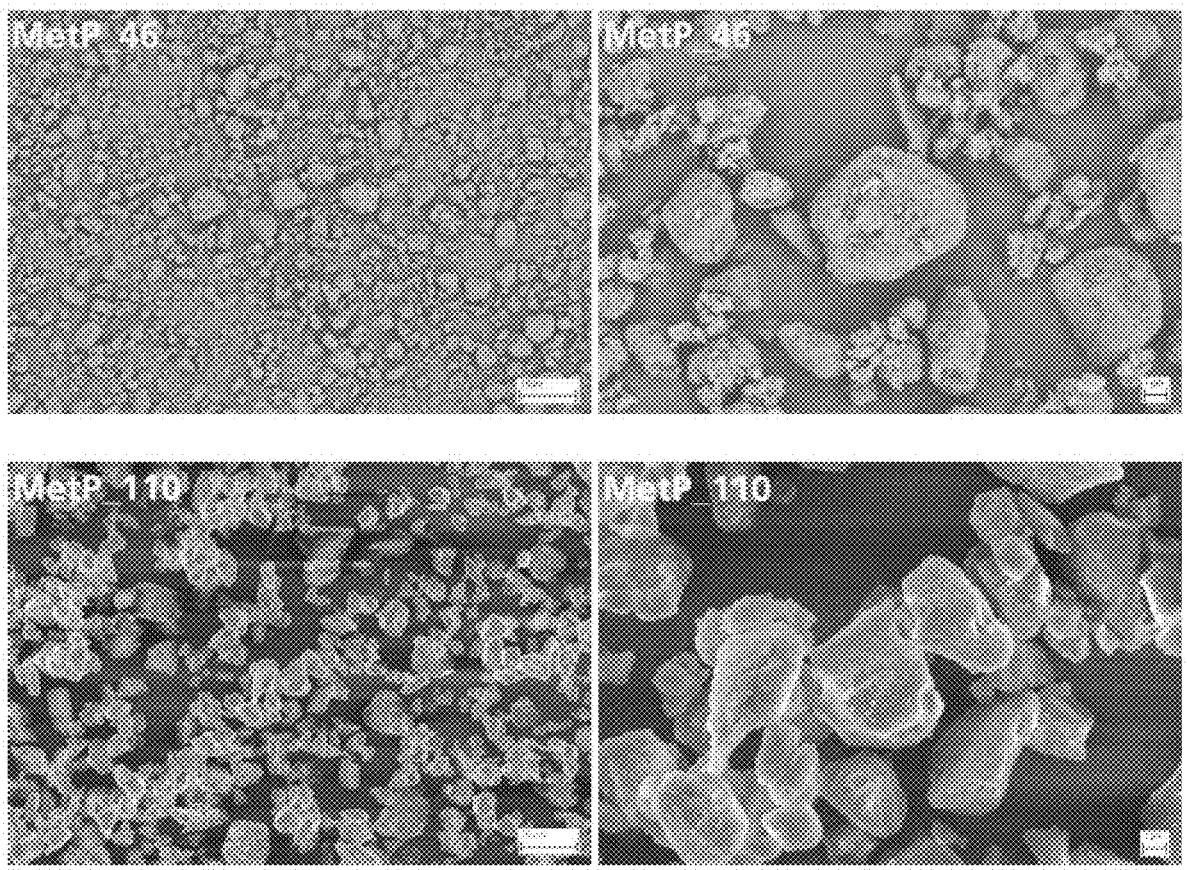
FIG. 3 shows scanning electron micrographs of spray dried compositions as described herein with SYLOID® 72FP particles and 244FP particles.

Scanning electron micrographs of the reference compositions, which are provided in FIG. 3, were obtained to examine the morphology and size of the particles. The scanning electron micrographs were taken at two separate focal lengths; in the sub-figures on the left side of FIG. 3, the bar represents a 10 µm distance, and in the sub-figures on the right side of FIG. 3, the bar represents a 1 µm distance.

Figure 4:
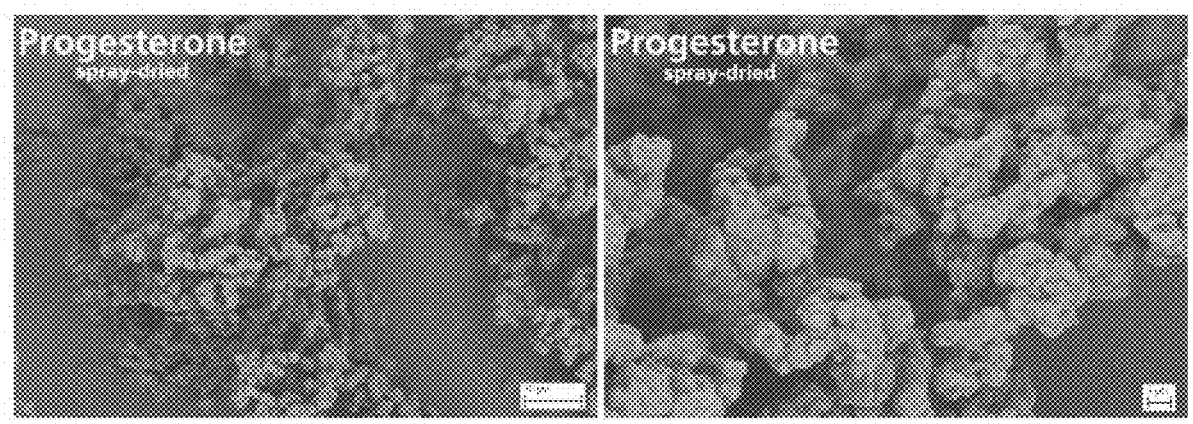
FIG. 4 shows scanning electron micrographs of spray dried progesterone.

As a separate reference, progesterone dissolved in ethanol—i.e., not loaded onto SYLOID® particles—was prepared by dissolving 0.214 g of progesterone in 50 ml of ethanol. The progesterone reference composition was spray dried with a Mini Spray Dryer B-290 (Büchi) with a two-fluid nozzle in the closed cycle system. The settings were constant with the aspirator rate at 100%, spray gas flow at 45 mm, pump rate at 10%, nozzle cleaner at 1, and $T_{in}$ a 81° C. The yield was determined to be 17.3% by comparing the weight of an empty glass vial to the glass vial containing spray dried particles. Scanning electron micrographs of the progesterone reference, which are provided in FIG. 4, were obtained to examine the morphology and size of the particles. The scanning electron micrographs were taken at two separate focal lengths; in the sub-figure on the left side of FIG. 4, the bar represents a 10 µm distance, and in the sub-figure on the right side of FIG. 4, the bar represents a 1 µm distance.

Example 6—Determination of Actual Progesterone Content

Actual progesterone content of spray dried progesterone+SYLOID® particles in Example 5 was determined by monitoring release of progesterone over about 7 days (it was assumed that 100% of encapsulated progesterone was released during this time). 3×10 mg of each batch of progesterone-loaded particles were weighed into small glass vials, and 20 ml of ethanol water (45/55 (v/v)) were added to the vials. The dispersions were stirred at 400 rpm and room temperature for about 7 days. The samples were then centrifuged at 15,000 rpm for 10 minutes and diluted. Mass concentration of the samples was determined using ultraviolet spectroscopy at 247 nm. Actual progesterone content and loading efficiency were calculated and are set forth in Table 4.

TABLE 4

Comparison of theoretical and actual progesterone loading in SYLOID ® particles.

| Batch | SYLOID ® | Theoretical progesterone loading (%) | Actual progesterone loading (%) | Loading efficiency (%) |
|---|---|---|---|---|
| MetP_106 | 244FP | 30.0 | 24.8 ± 0.3 | 82.9 |
| MetP_107 | 244FP | 40.0 | 37.1 ± 0.5 | 92.8 |
| MetP_108 | 244FP | 50.0 | 47.4 ± 1.2 | 95.0 |
| MetP_109 | 244FP | 60.0 | 58.0 ± 0.6 | 96.7 |
| MetP_111 | 72FP | 30.0 | 21.4 ± 0.8 | 71.6 |
| MetP_112 | 72FP | 40.0 | 31.1 ± 0.4 | 77.8 |
| MetP_113 | 72FP | 50.0 | 42.1 ± 0.6 | 84.4 |
| MetP_114 | 72FP | 60.0 | 57.5 ± 1.0 | 95.8 |

Example 7—Thermal Behavior of Encapsulated Progesterone

Figure 5:
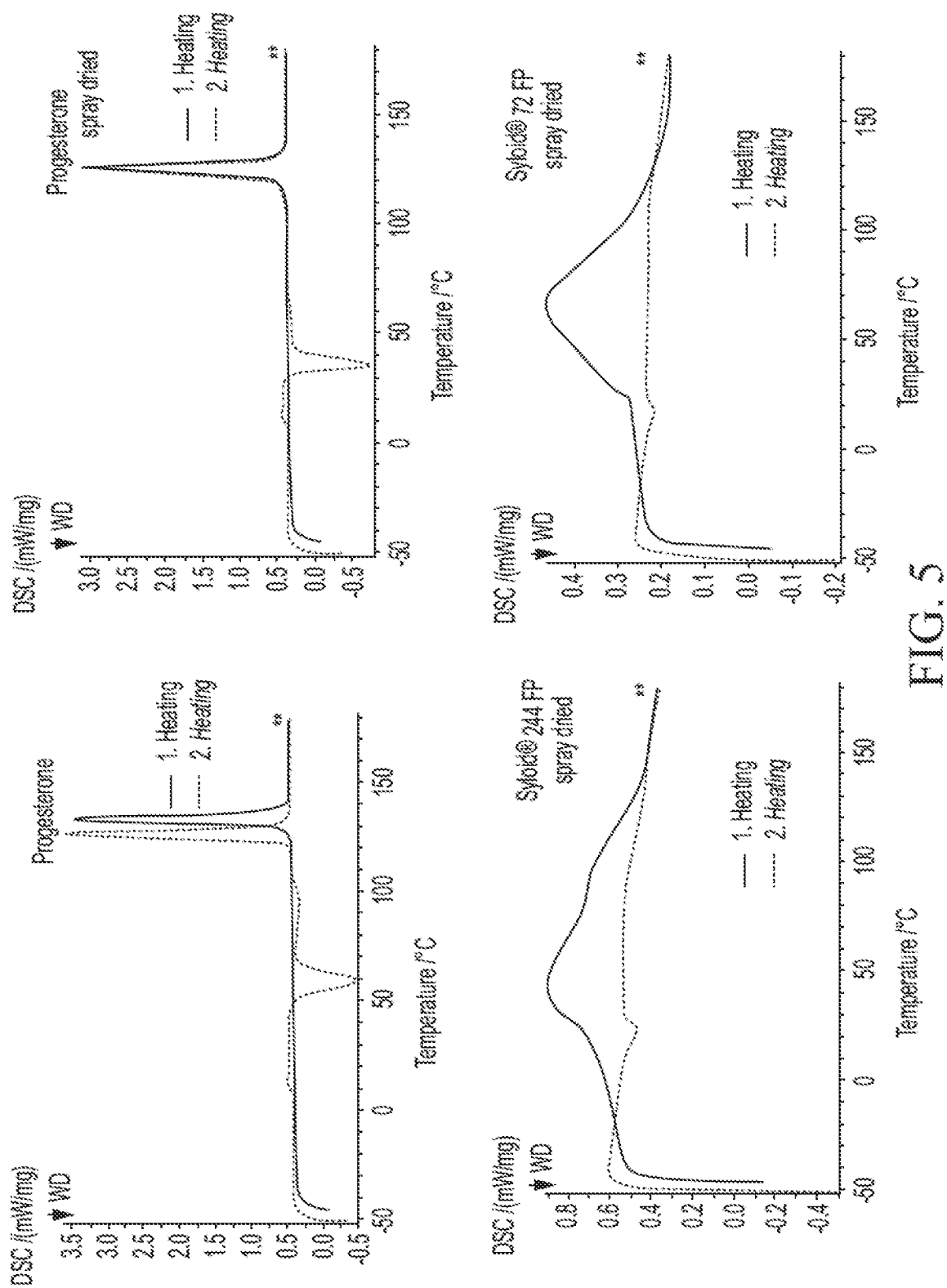
FIG. 5 shows differential scanning calorimetry measurements of spray-dried progesterone, spray-dried SYLOID® 72FP, and spray-dried SYLOID® 244FP.

Thermal behavior of the spray dried progesterone+SYLOID® particles in Example 5 was assessed via differential scanning calorimetry. All samples were measured twice from −50° C. to 180° C. with a heating and cooling rate of 10 K/min, on a DSC 200 F3 MAIA® (Netzch). Progesterone dissolved in ethanol was spray dried under the same conditions as the progesterone+SYLOID® particles, and was used as a reference. Also used as a references were non-spray dried progesterone, and spray dried SYLOID® 72FP particles or SYLOID® 244FP particles without progesterone. DSC curves for the references are shown in FIG. 5. For the progesterone references, melting points (peak temperature), glass transition temperature (onset), and recrystallization (peak temperature) of the two heating cycles were determined and are set forth in Table 5.

TABLE 5

Thermal behavior of progesterone from DSC curves obtained with reference samples.

| Progesterone | 1. Heating melting point (° C.) | 2. Heating glass transition (° C.) | 2. Heating recrystallization (° C.) | 2. Heating melting (° C.) |
|---|---|---|---|---|
| non-spray-dried | 133.1 | 7.7 | 59.2 | 126.3 |
| spray-dried | 126 | 6.9 | 35.4 | 125.1 |

Figure 6:
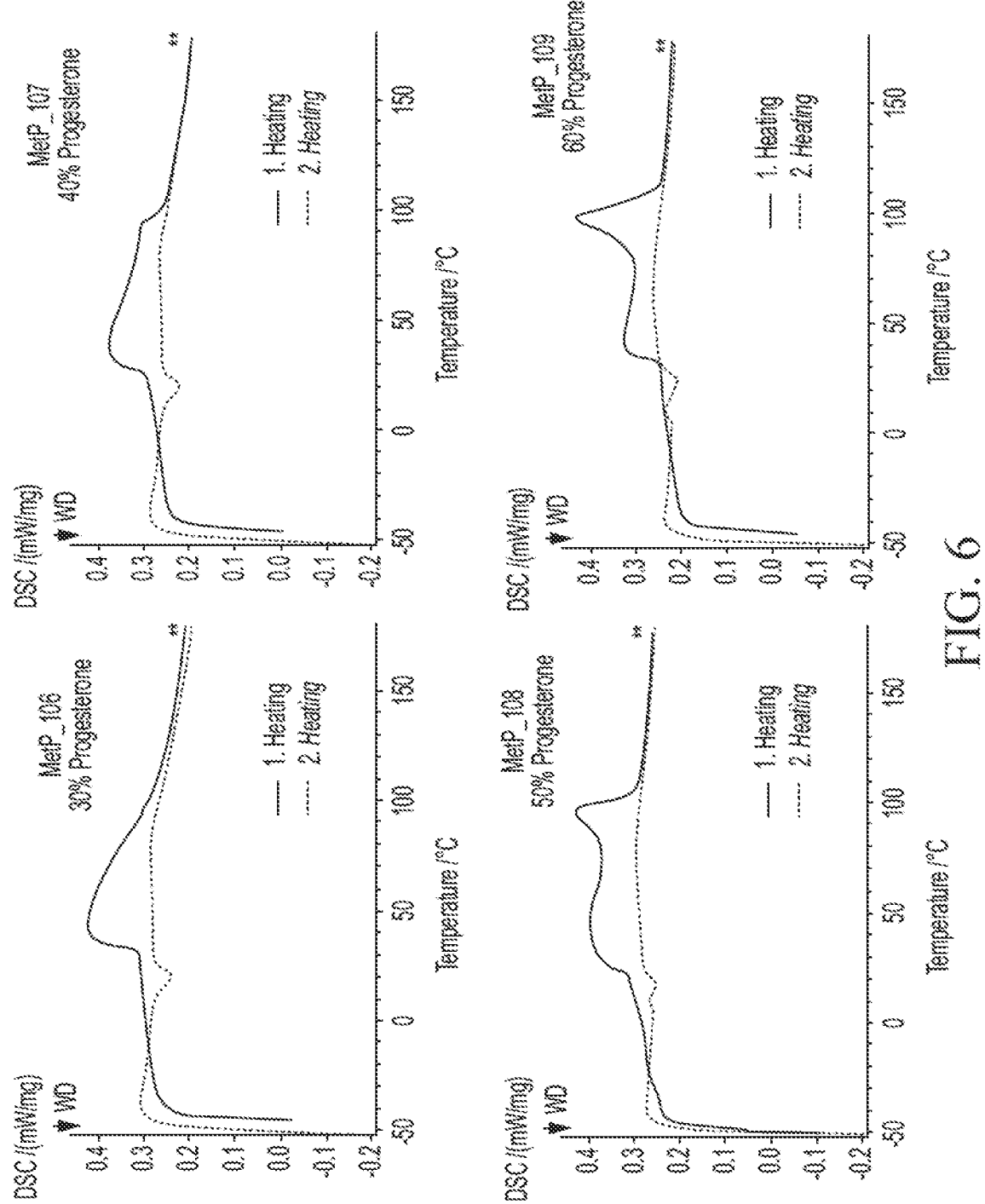
FIG. 6 shows differential scanning calorimetry measurements of spray-dried compositions as described herein with progesterone and SYLOID® 244FP.

Thermal behavior of the spray dried progesterone+SYLOID® 244FP particles is demonstrated by DSC measurements shown in FIG. 6. FIG. 6 shows that in SYLOID® 244FP compositions with an actual loading of 37% progesterone, a melting peak begins to appear at just below 100° C. (MetP_107). Without being bound by theory, it is believed that this peak represents a polymorph form (e.g., a V-form) of progesterone. FIG. 6 also demonstrates that with an increase in progesterone, rising peaks were detected at 96.5° C. (MetP_108) and 99.2° C. (MetP_109).

Figure 7:
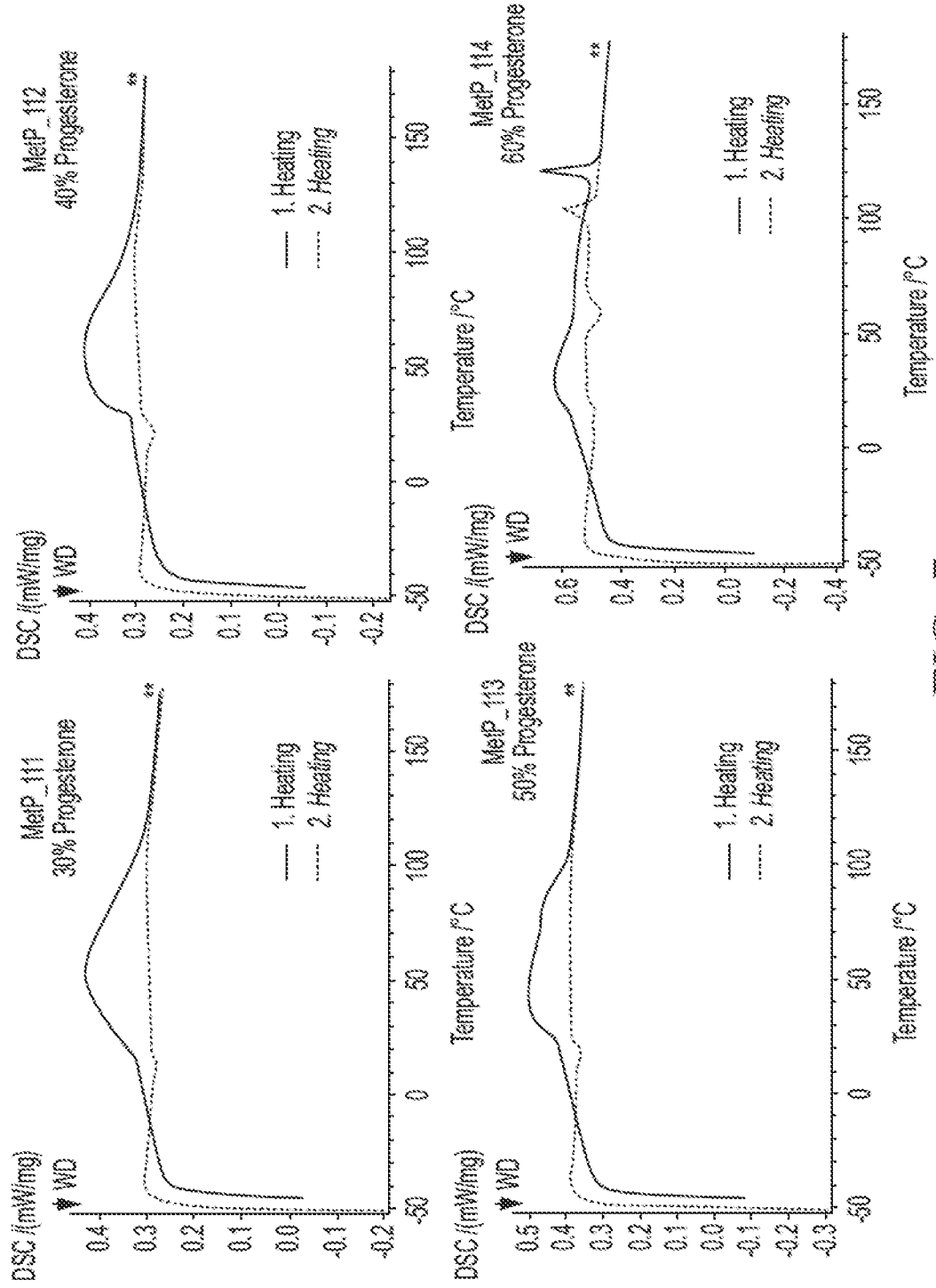
FIG. 7 shows differential scanning calorimetry measurements of spray-dried compositions as described herein with progesterone and SYLOID® 72FP.

Thermal behavior of the spray dried progesterone+SYLOID® 72FP particles is demonstrated by DSC measurements shown in FIG. 7. FIG. 7 shows that in SYLOID® 72FP compositions with an actual loading of 42% (MetP_113), a shoulder appears below 100° C. FIG. 7 also shows a melting point of 125° C. in the first heating cycle and a peak at about 100° C. in the second cycle with compositions that have an actual progesterone loading of 57.5% (MetP_114). Without being bound by theory, it is believed that these two melting points result from progesterone crystal forms II and V.

Example 8—Progesterone-Loaded Ordered Mesoporous Silica

Figure 8:
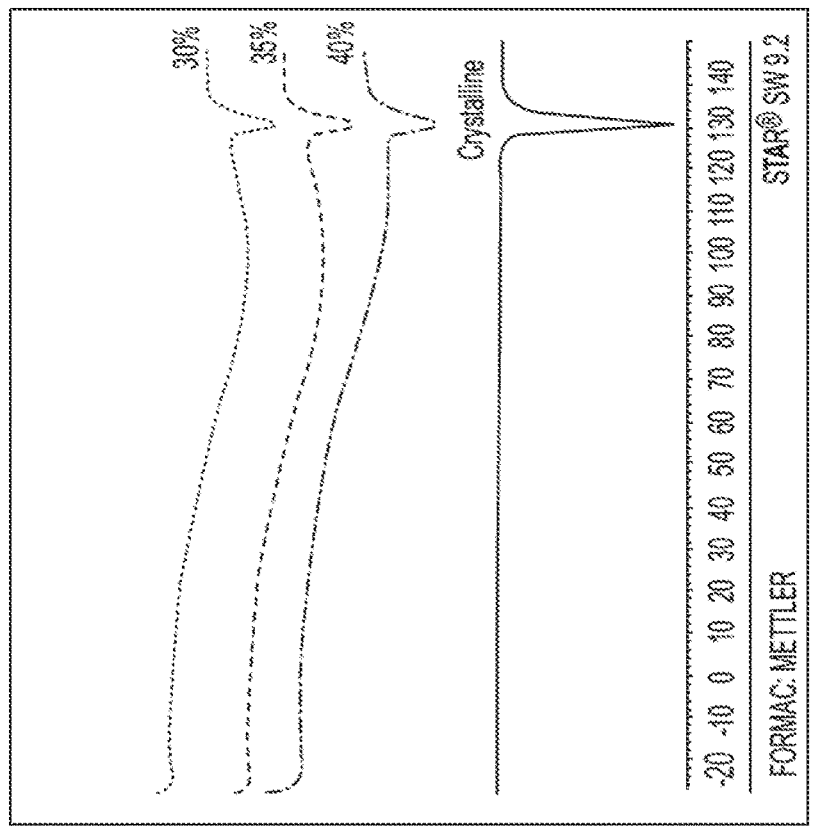
FIG. 8 shows differential scanning calorimetry thermograms of compositions as described herein with progesterone loaded onto ordered mesoporous silica OSM-7.
Figure 8:
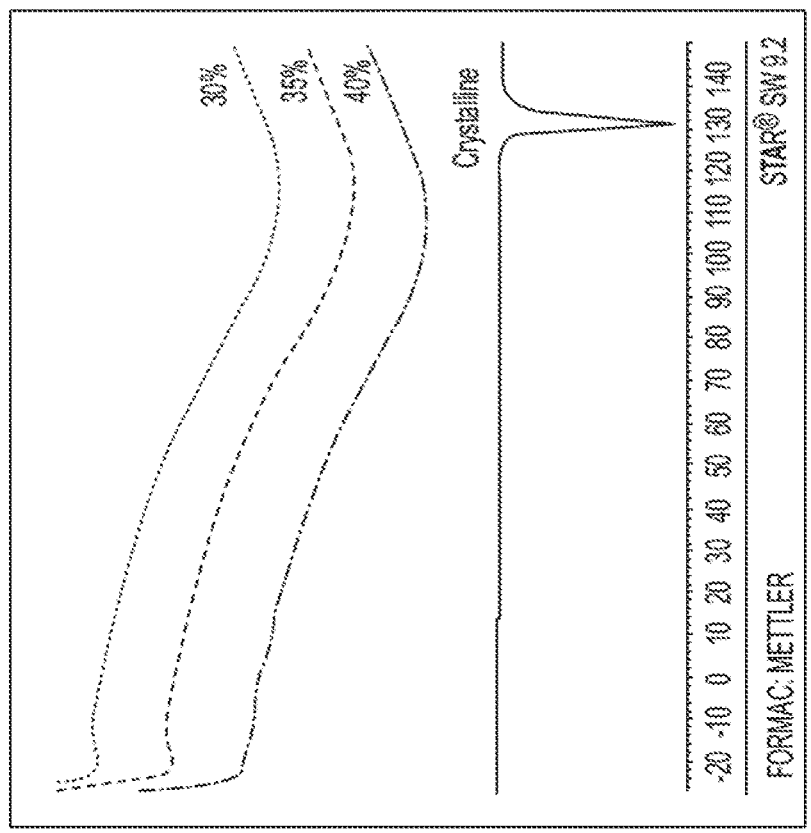

Progesterone was impregnated on ordered mesoporous silica (OMS-7) powder using either 200 mg/ml solutions of progesterone in methylene chloride or 100 mg/ml solutions of progesterone in acetone to obtain loadings of 30%, 35%, and 40% (w/w) progesterone. Subsequent to impregnation, the loaded silica powders were dried under vacuum for at least 24 hours at 40° C. to remove excess solvent. Morphology of the samples was assessed using differential scanning calorimetry thermograms, which are shown in FIG. 8. FIG. 8 demonstrates that samples prepared with methylene chloride appeared amorphous, whereas samples prepared with acetone were in crystalline form.

Figure 9:
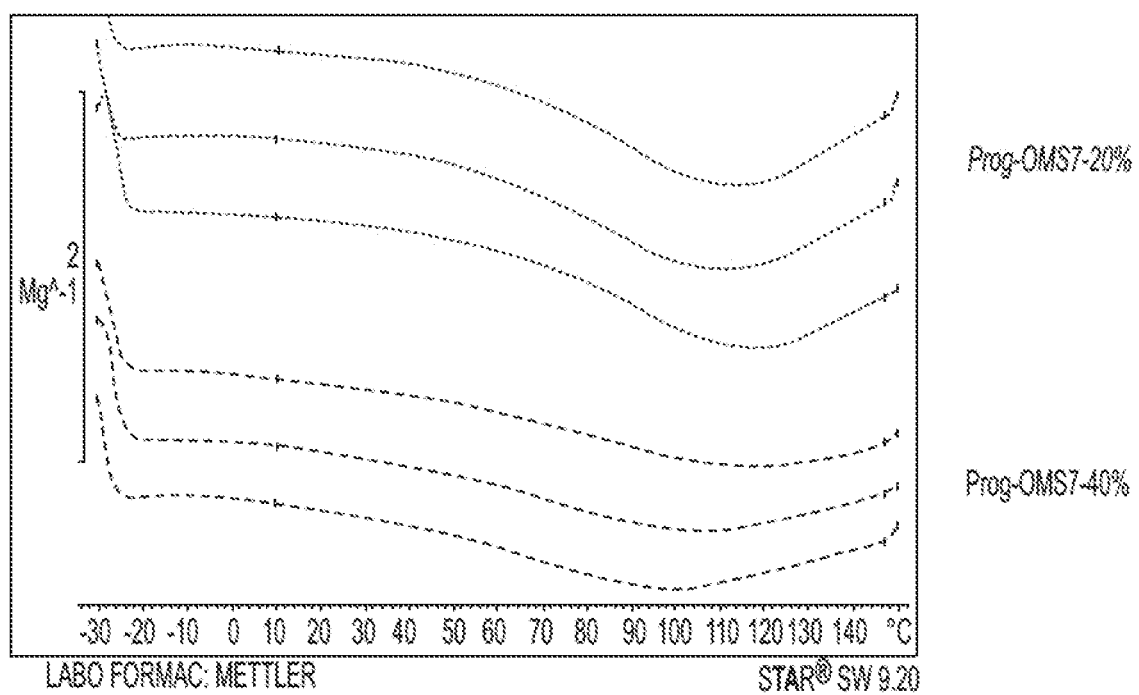
FIG. 9 shows differential scanning calorimetry thermograms of compositions as described herein with 20% and 40% progesterone loaded onto ordered mesoporous silica OSM-7.

In a separate experiment, progesterone was loaded onto OMS-7 at target concentrations of 20% and 40% (w/w) using methylene chloride, and the samples were dried as set forth above. Actual progesterone content was determined to be 20.2±0.2% (w/w) (n=3) and 38.3±0.9% (w/w) (n=3), respectively. Differential scanning calorimetry thermograms show that the progesterone in all samples is in amorphous form, as shown in FIG. 9.

Figure 10:
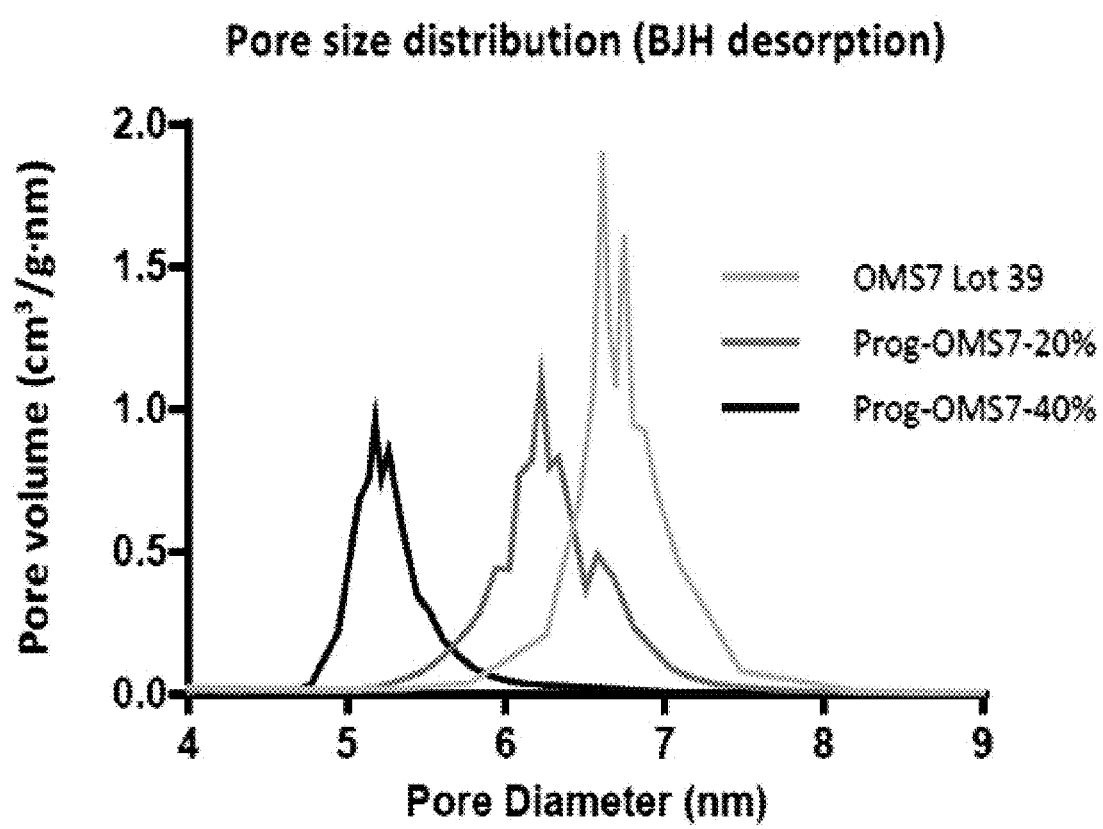
FIG. 10 shows the pore size distribution of OSM-7 particles with and without progesterone absorbed to the OSM-7.

Nitrogen physisorption experiments confirmed that progesterone was adsorbed into the pores of OMS-7. In particular, the data demonstrate a consistent decrease in pore volume and surface area following progesterone loading. These results are summarized in Table 6, and depicted visually in FIG. 10, where "OMS-7 Lot 39" is OMS-7 without progesterone, "Prog-OMS-7-20%" is OMS-7 with about 20% progesterone, and "Prog-OMS-7-40%" is OMS-7 with about 40% progesterone. The pore size distribution was calculated from the desorption branches of the isotherm using the Barrett-Joyner-Halenda (BJH) model. The total surface area was calculated via the Brunauer-Emmett-Teller (BET) model. The total pore volume was derived directly from the isotherm at $p/p_0=0.95$. The data indicate a progressive decrease in pore diameter with loading, indicative of layer wise deposition of progesterone onto the OMS-7 surface. Without being bound by theory, it is believed that progesterone is interacting with both the OMS-7 and also with other progesterone moieties, for instance through capillary forces or Van der Waals interactions.

TABLE 6

Porosity Data from nitrogen physisorption experiments.

| Sample | Total Pore Volume ($cm^3/g$) | Total Surface Area ($m^2/g$) | Mean Pore Diameter (nm) |
|---|---|---|---|
| OMS-7 Lot 39 | 1.14 | 925 | 6.6 |
| Prog-OMS-7-20% | 0.80 | 509 | 6.2 |
| Prog-OMS-7-40% | 0.48 | 286 | 5.2 |

Example 9—Testosterone-Loaded Ordered Mesoporous Silica

Figures 11A, 11B:
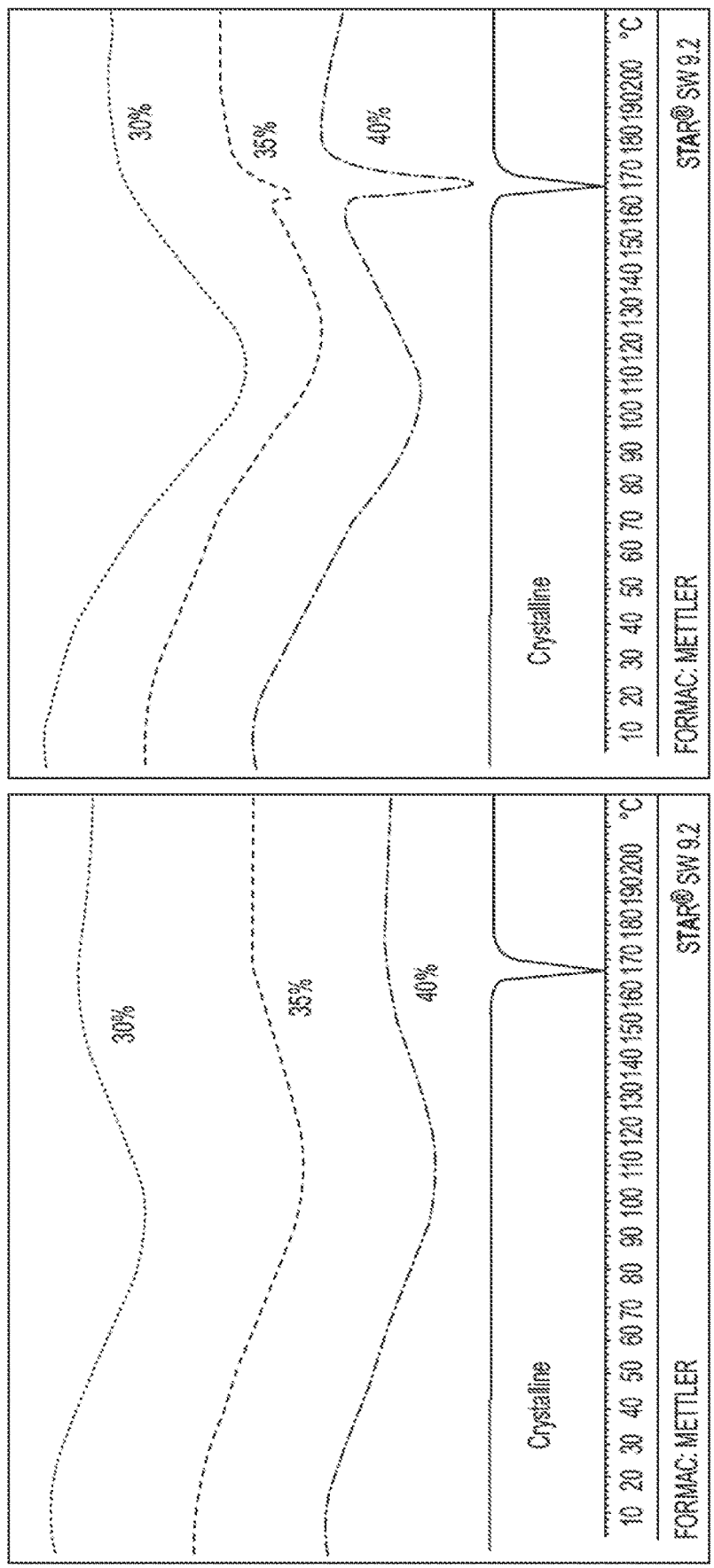
FIG. 11 (FIGS. 11A-B) shows differential scanning calorimetry thermograms of compositions as described herein with testosterone loaded onto ordered mesoporous silica OSM-7.

Testosterone was impregnated on ordered mesoporous silica (OMS-7) powder using either 200 mg/ml solutions of testosterone in methylene chloride or 100 mg/ml solutions of testosterone in ethanol to obtain loadings of 30%, 35%, and 40% (w/w) testosterone. Subsequent to impregnation, the loaded silica powders were dried under vacuum for at least 24 hours at 40° C. to remove excess solvent. Morphology of the samples was assessed using differential scanning calorimetry thermograms, which are shown in FIGS. 11A-B. FIGS. 11A-B demonstrates that samples prepared with methylene chloride appeared amorphous, whereas samples prepared with ethanol were in crystalline form.

Figure 12:
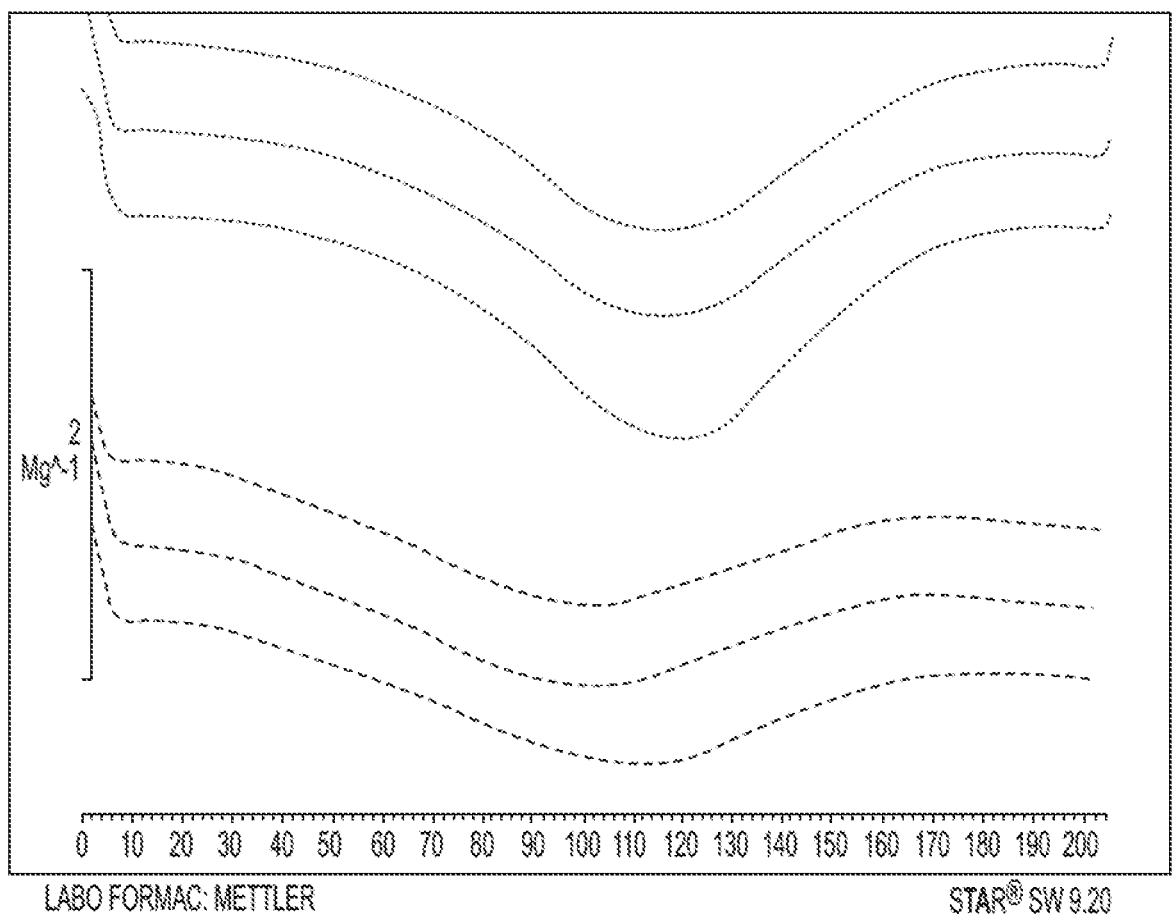
FIG. 12 shows differential scanning calorimetry thermograms of compositions as described herein with 20% and 40% testosterone loaded onto ordered mesoporous silica OSM-7.

In a separate experiment, testosterone was loaded onto OMS-7 at target concentrations of 20% and 40% (w/w) using methylene chloride, and the samples were dried as set forth above. Actual testosterone content was determined to be 20.1±0.4% (w/w) (n=3) and 37.9±1.9% (w/w) (n=3), respectively. Differential scanning calorimetry thermograms show that the testosterone in all samples is in amorphous form, as shown in FIG. 12.

Figure 13:
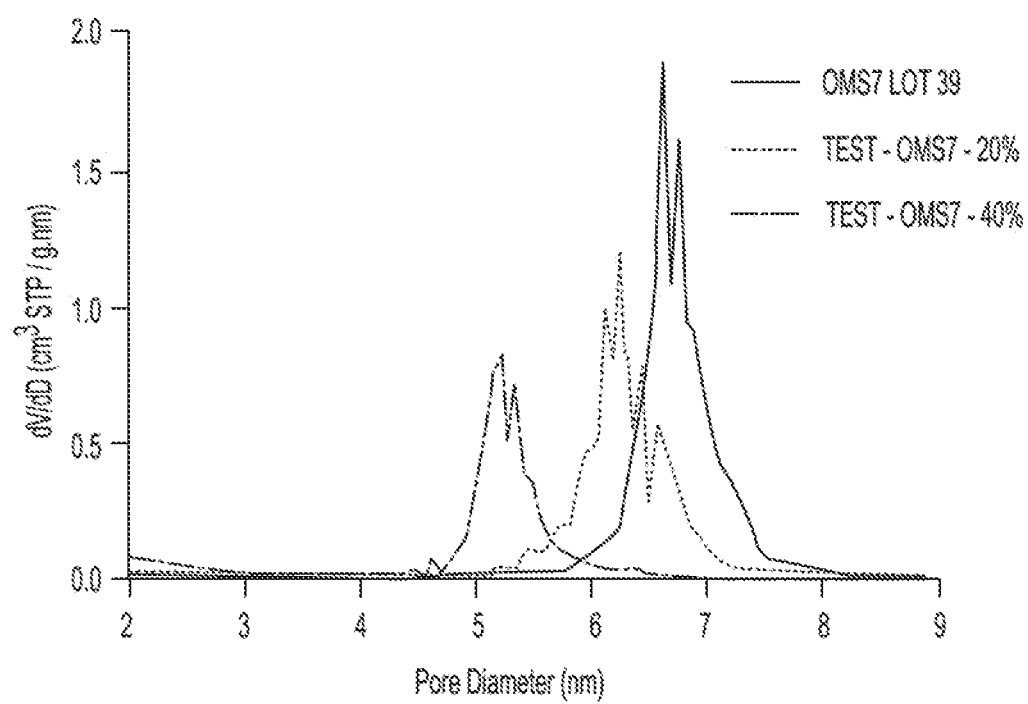
FIG. 13 shows the pore size distribution of OSM-7 particles with and without testosterone absorbed to the OSM-7.

Nitrogen physisorption experiments confirmed that testosterone was adsorbed into the pores of OMS-7. In particular, the data demonstrate a consistent decrease in pore volume and surface area following progesterone loading. These results are summarized in Table 7, and depicted visually in FIG. 13, where "OMS-7 Lot 39" is OMS-7 without testosterone, "Test-OMS-7-20%" is OMS-7 with about 20% testosterone, and "Test-OMS-7-40%" is OMS-7 with about 40% testosterone. The pore size distribution was calculated from the desorption branches of the isotherm using the Barrett-Joyner-Halenda (BJH) model. The total surface area was calculated via the Brunauer-Emmett-Teller (BET) model. The total pore volume was derived directly from the isotherm at $p/p_0=0.95$. The data indicate a progressive decrease in pore diameter with loading, indicative of layer wise deposition of testosterone onto the OMS-7 surface.

TABLE 7

Porosity Data from nitrogen physisorption experiments.

| Sample | Total Pore Volume ($cm^3/g$) | Total Surface Area ($m^2/g$) | Mean Pore Diameter (nm) |
|---|---|---|---|
| OMS-7 Lot 39 | 1.14 | 925 | 6.6 |
| Test-OMS-7-20% | 0.82 | 518 | 6.2 |
| Test-OMS-7-40% | 0.46 | 271 | 5.2 |

Example 10—Progesterone Gel Compositions

Progesterone gel compositions with encapsulated progesterone were prepared as set forth in Table 8. In composition 1, additional colloidal anhydrous silica was added to improve viscosity, resulting in a composition with component amounts that exceed 100% (the % weights in Composition 1 total 102%).

TABLE 8

Progesterone Gel Compositions

| Component | Composition 1 Component Amount (%) | Composition 2 Component Amount (%) | Procedure |
|---|---|---|---|
| Castor Oil | 70.3 | 76.8 | During manufacture, avoided air bubbles and warming |
| Oleoyl Polyoxylglycerides | 4.0 | 4.0 | Added to castor oil and mixed for 1 min at 13000 rpm |
| Micronized progesterone | 6.4 | 4.6 | Added and mixed for 2 min at 13000 rpm |
| Progesterone-adsorbate 40% | 17.3 | 8.6 | Added and homogenized slightly by hand; mixed for 2 min at 13000 rpm |
| Colloidal anhydrous silica | 2.0 | 6.0 | Added and homogenized slightly by hand; mixed for 10 min at 13000 rpm |

Example 11—Testosterone Gel Compositions

Testosterone gel compositions with encapsulated testosterone were prepared as set forth in Table 9.

TABLE 9

Testosterone Gel Compositions

| Component | Composition 1 Component Amount (%) | Composition 2 Component Amount (%) | Procedure |
|---|---|---|---|
| Castor Oil | 76.08 | 83.56 | During manufacture, avoided air bubbles and warming |
| Testosterone Adsorbate 20% | 15.92 | — | Added to castor oil and mixed for 2 min at 13000 rpm |
| Testosterone Adsorbate 40% | — | 8.44 | Added to castor oil and mixed for 2 min at 13000 rpm |
| Oleoyl Polyoxylglycerides | 4.00 | 4.00 | Added and mixed for 2 min at 13000 rpm |
| Colloidal anhydrous silica | 4.00 | 4.00 | Added and homogenized slightly by hand; mixed for 10 min at 13000 rpm |

Example 12—Spray Drying of Testosterone

To test the extent to which the active agent testosterone was altered due to the spray process, it was spray dried in pure ethanol. To this end, 0.214 g of testosterone was dissolved in 50 mL of ethanol. This concentration represents that employed for a 30% testosterone loading. The solutions were sprayed in the Mini Spray Dryer using a closed system of suction. Settings were 10% pump power, 100% aspirator power, dispersion gas at 45 mm and the nozzle cleaner held constant at 1. The variable parameters are shown in Table 10.

TABLE 10

Inlet temperatures $T_{in}$ of the spray-drying experiments with the perspective testosterone batches and their yields.

| Testosterone | $T_{in}$ (° C.) | Yield (%) |
|---|---|---|
| first delivery (MetP_99) | 110 | 19.9 |
| second delivery (MetP_103) | 81 | 10.9 |

Figure 14:
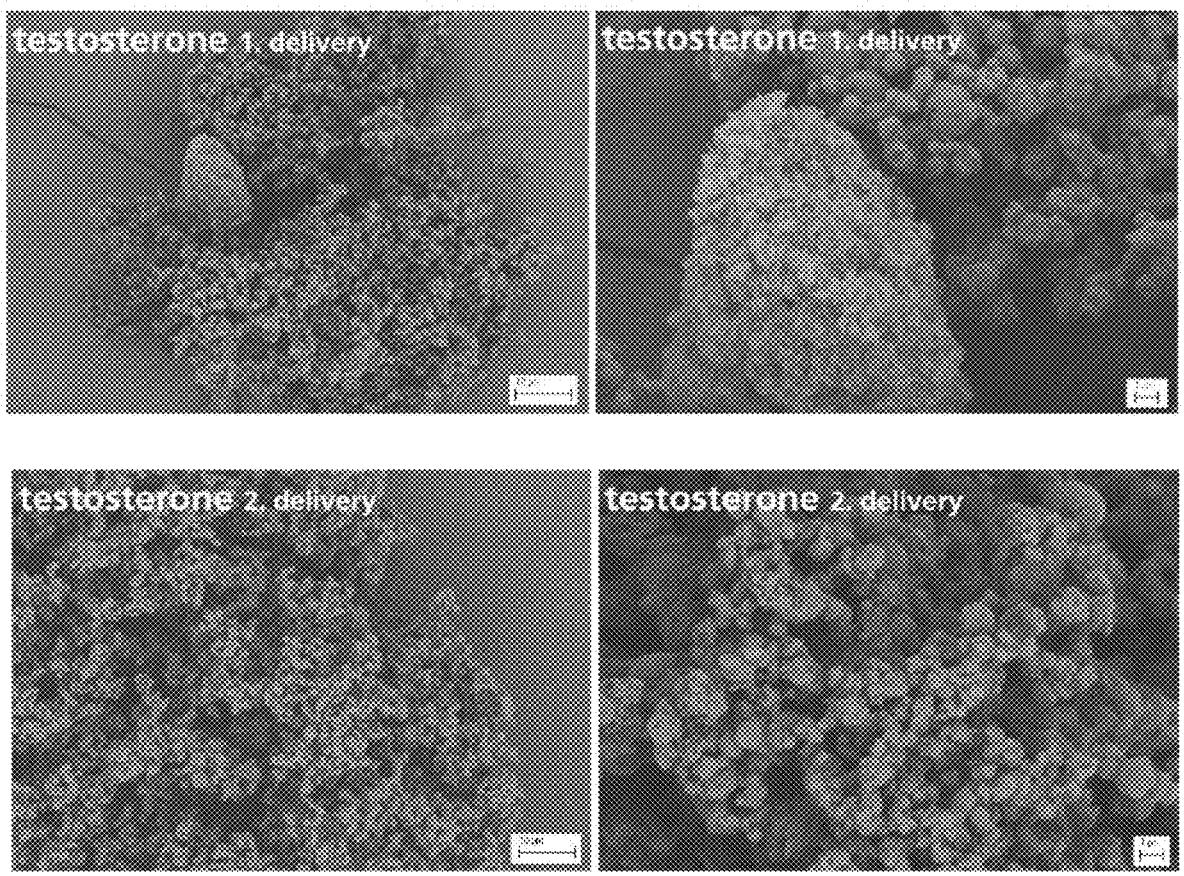
FIG. 14 shows scanning electron micrographs of spray dried testosterone.

The yields of pure testosterone from spray drying were relatively small, likely due to large amounts of the testosterone found in the cyclone, i.e., not deposited into the product collection vessel. Scanning electron microscope photographs (SEM images) are shown in FIG. 14, which shows that testosterone is present in particulate form following spray drying. In the figure, "1. delivery" represents a first batch of testosterone, and "2. delivery" represents a second batch of testosterone.

Example 13—Loading of Testosterone in Polymeric Matrices

Compositions were prepared with testosterone encapsulated in the presence of the following polymers: polylactide, chitosan, or gelatin.

Polylactide Loading

Polylactide polymers RESOMER® 202H and RESOMER® 202S (Evonik) were dissolved in dichloromethane, and testosterone was added at either 10% or 30% weight based on the total weight of testosterone+RESOMER®. The solutions were sprayed in a Mini Spray Dryer using a two-fluid nozzle in a closed system of suction. During this step, the aspirator power remained constant at 100%, the dispersion gas at 50 mm and the nozzle cleaner at 1. $T_{in}$ temperatures resulted from existing room temperature. Yields obtained with these experiments are set forth in Table 11.

TABLE 11

Parameters of spray-drying experiments with polylactide and resulting yields.

| Batch | Material | Amount of PLA (%) in dichloromethane solution | Theoretical loading (testosterone) (%) | Feed rate (%) | $T_{in}$ (° C.) | Yield (%) |
|---|---|---|---|---|---|---|
| MetP_05 | 202H | 1 | — | 14 | 50 | 4.8 |
| MetP_02 | 202H | 1 | — | 14 | 60 | 4.7 |
| MetP_06 | 202S | 1 | — | 14 | 50 | 3.6 |
| MetP_07 | 202S | 1 | — | 14 | 60 | 4.0 |
| MetP_27 | 202H | 5 | — | 14 | 50 | 10.2 |
| MetP_28 | 202H | 5 | 10 | 14 | 50 | 4.2 |
| MetP_45 | 202H | 10 | — | 14 | 50 | 25.3 |
| MetP_60 | 202H | 10 | — | 24 | 50 | 53.1 |
| MetP_61 | 202H | 10 | — | 14 | 25 | 63.8 |
| MetP_74 | 202H | 10 | 10 | 14 | 29 | 60.4 |
| MetP_75 | 202H | 10 | 30 | 14 | 28 | 52.2 |
| MetP_85* | 202H | 10 | 30 | 14 | 38 | 44.1 |

*MetP_85 was prepared analogously to MetP_75, but in duplicate batch size.

The yield was increased from 4.8% to 25.3% by increasing the PLA quantity added, and from 25.3% to 63.8% by additionally reducing the entry temperature $T_{in}$. Without being bound by theory, it is believed that increased deposition of the particles in the cyclone might have occurred due to the low glass transition temperature of the polylactides and the initially excessive temperatures. A small reduction in yield to 52.2% resulted from the addition of the testosterone to the polymer solution.

Figure 15A:
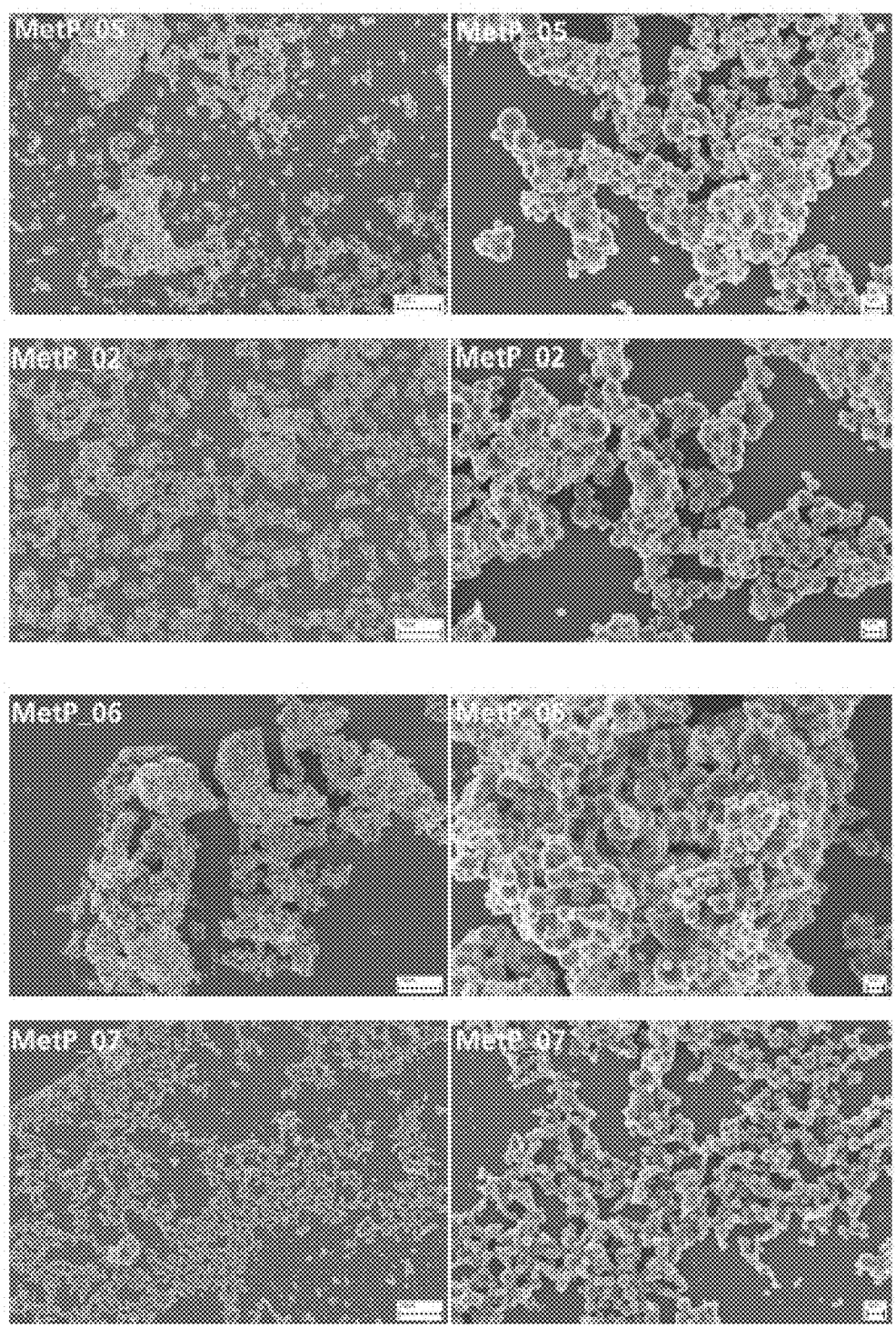
FIG. 15 (FIGS. 15A-C) shows scanning electron micrographs of spray dried compositions as described herein with testosterone and polylactide.
Figure 15B:
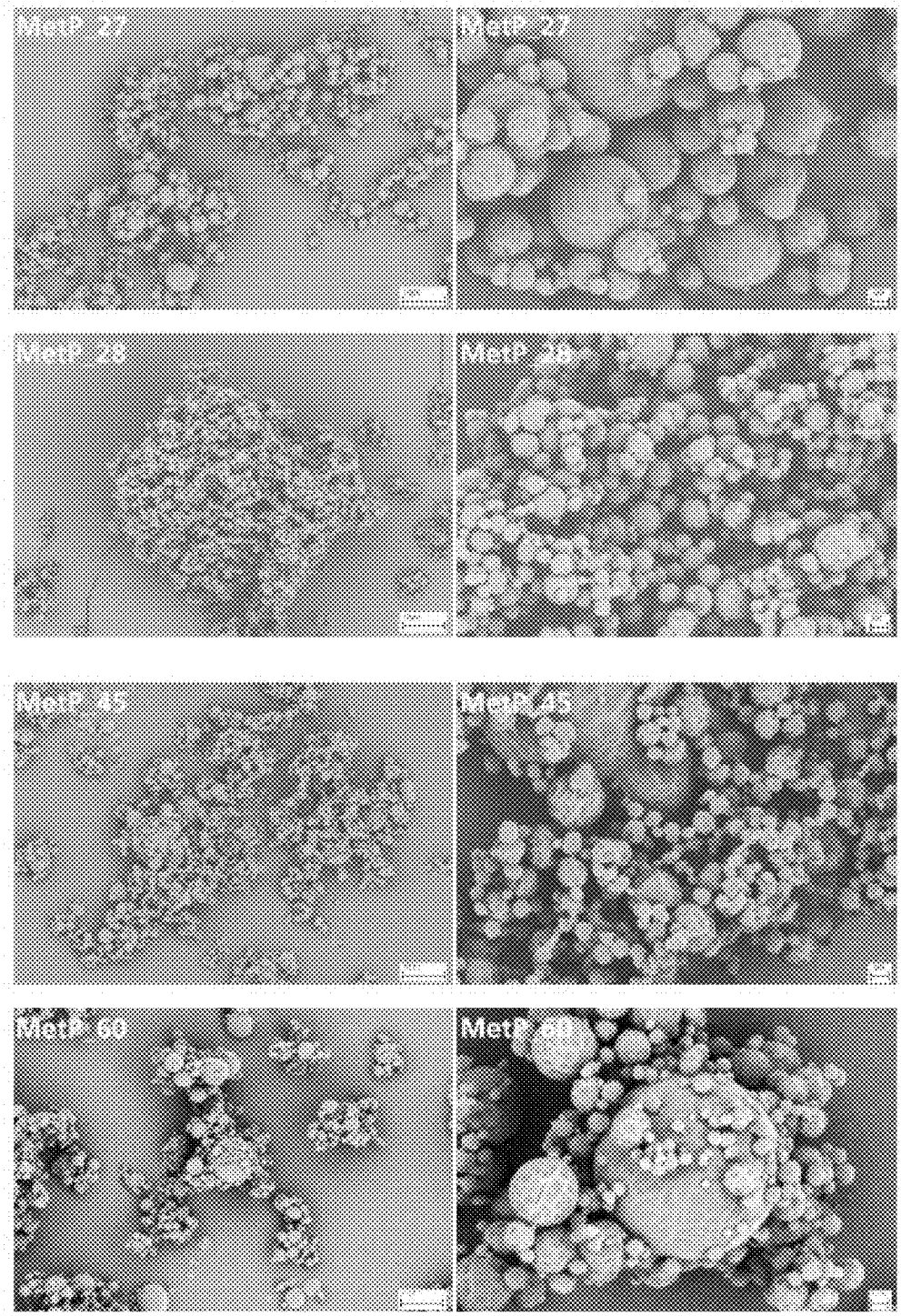
Figure 15C:
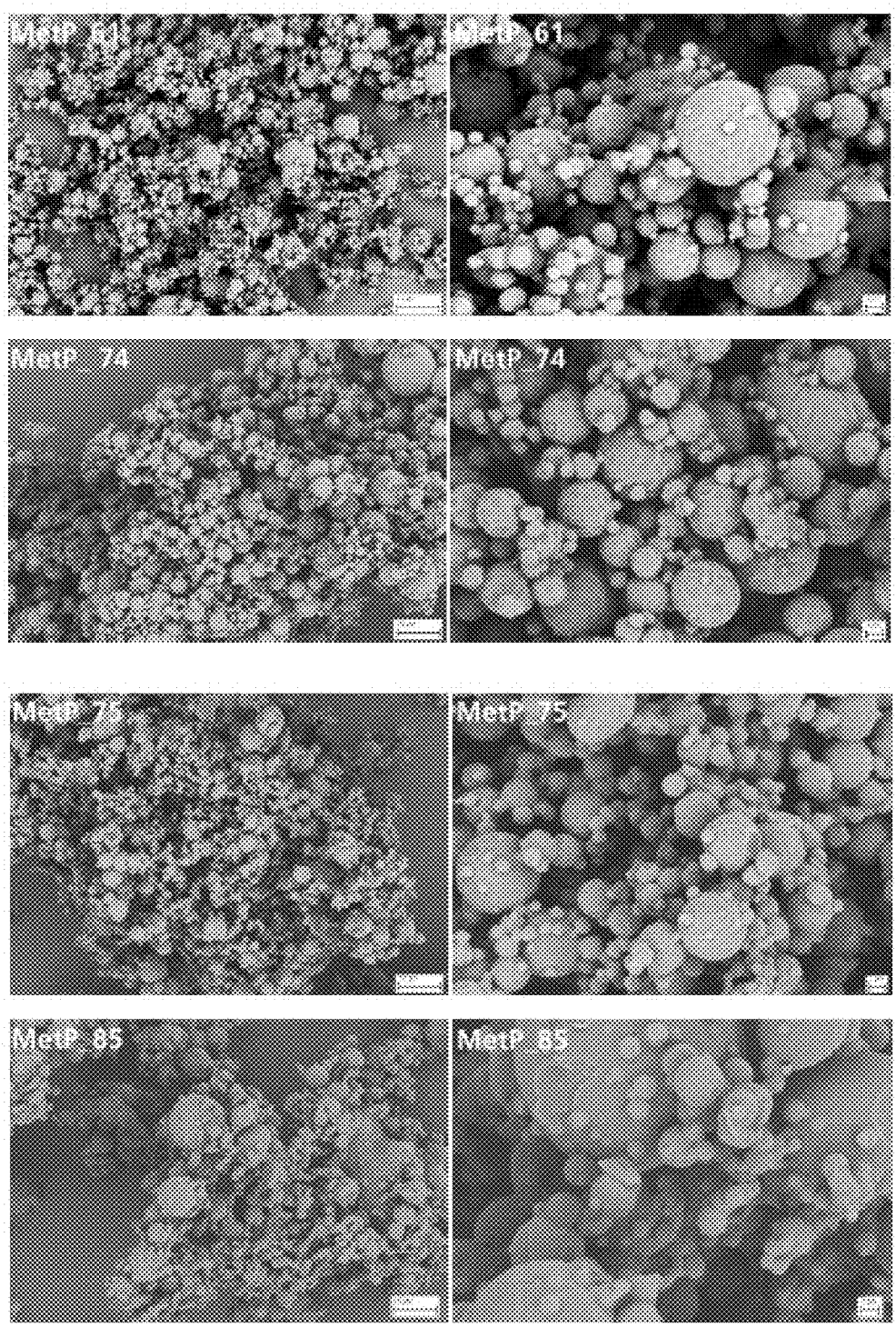

The morphology of the particles are shown in the SEM images in FIGS. 15A-C. In the initial experiments, it was shown that non-aggregated, more uniform particles could be produced using RESOMER® 202H (MetP_05/MetP_02) compared to RESOMER® 202S (MetP_06/MetP_07), perhaps due to the differing glass transition temperatures (Tg) of the two amorphous polylactides. RESOMER® 202H, which has a higher Tg than RESOMER® 202S, was used for further experiments.

Increasing the quantities of PLA added by 5% (MetP_27) and 10% (MetP_45) resulted in an increased in particle size and distribution of sizes. Increasing the pumped speed the spray solution (MetP_60) and reducing the entry temperature (MetP_61) had no significant influence on the morphology. The addition of testosterone (10%:MetP_74, 30%: MetP_75) also had no significant influence. Doubling the quantity of composition produced (MetP_85) appeared to result in a further increase in particle size.

Chitosan Loading

A chitosan solution was formed by dissolving 0.5 g of pharmaceutical-grade chitosan 95/200 (deacetylation level 95%, viscosity in 1% acetic acid: 151-350 mPa) in 50 ml of 2% acetic acid. For control experiments, 50 ml of ethanol was added to the chitosan solution. In testosterone compositions, 48 ml of ethanol was added to the chitosan solution; testosterone was dissolved in 2 ml of ethanol, and then added to the chitosan/ethanol solution. The solutions were spray-dried in a Mini Spray Dryer using a two-fluid nozzle in a closed system of suction and stir speed of 200 rpm. Dryer settings were as follows: entry temperature 140° C., 10% pump power, 100% aspirator power, dispersion gas at 50 mm and the nozzle cleaner at 1 remained constant. Yields obtained with these experiments are set forth in Table 12.

TABLE 12

Parameters of spray-drying experiments with chitosan and their resultant yields.

| Batch | Theoretical loading (testosterone) [%] | Yield [%] |
|---|---|---|
| MetP_40 | — | 72.4 |
| MetP_41 | 10 | 60.0 |
| MetP_42 | 30 | 68.6 |

Figure 16:
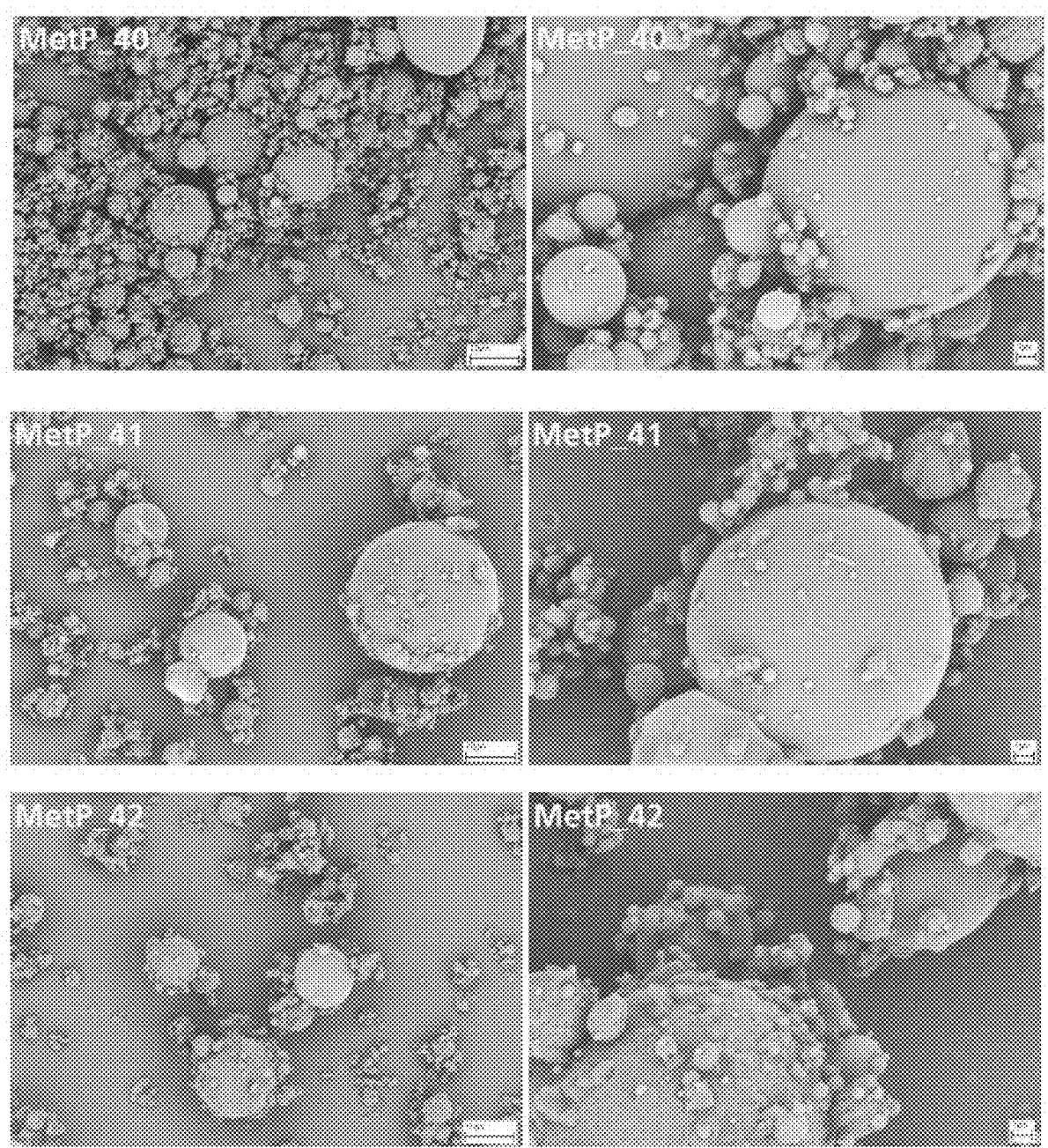
FIG. 16 shows scanning electron micrographs of spray dried compositions as described herein with testosterone and chitosan.

The yields of the particles produced were between 60.0% and 72.4%. The morphology of the particles are shown in the SEM images of FIG. 16, which shows particles with a broad distribution of sizes.

In separate experiments, chitosan was electrostatically cross-linked with tripolyphosphate (TPP) to increase the stability of the material and thereby induce a retardation effect (i.e., a delayed release effect). To do this, 2% TPP solution (2% acetic acid and ethanol in a ratio of 1:1, v/v) was added to the chitosan solution. However, the chitosan solution immediately agglomerated with the addition of the TPP, the solution could not be sprayed in a single phase through the two-fluid nozzle.

To circumvent this prior cross-linking, an attempt to achieve cross-linking in situ, i.e. cross-linking during the spray process was carried out in the next step. For this purpose, the three-fluid nozzle was employed for the spray drying to simultaneously spray a chitosan and a TPP solution in one jet. Different spray parameters were varied for this purpose, but they could not be set during the feasibility study in such a way that enabled cross-linking to be carried out by means of the three-fluid nozzle.

Gelatin Microencapsulation

Three different gelatins derived from fish, and that differ in Bloom grade, were used for encapsulating testosterone: F15 (Bloom grade: 150), F20 (Bloom grade: 200), and F25 (Bloom grade: 300).

To produce unloaded gelatin particles, gelatin was dissolved in water and sprayed as (i) a single-phase or (ii) an emulsion of water and dichloromethane. For MetP_08 to MetP_10 in Table 13A, 0.5 g of gelatin each was dissolved in 50 mL of water; for MetP_11 to MetP_13 in Table 13A, 0.5 g of gelatin each was dissolved in 47.5 mL of water. The mixtures were agitated in an incubating shaker at 37° C. to achieve complete dissolution and subsequently brought to room temperature. For MetP_11 to MetP_13, 0.175 g of TWEEN® 20 and 2.5 mL of dichloromethane was also added. The mixtures were subsequently homogenized by a rotor/stator set-up for 10 minutes at 30,000 rpm while cooling it by means of ice.

The gelatin solutions and emulsions were subsequently sprayed in the Mini Spray Dryer using a two-fluid nozzle in a closed system with suction. Settings remained constant with aspirator power 100%, dispersion gas 45 mm, nozzle cleaner at 1, pump power at 10%, and entry temperature $T_{in}$ of 135° C. The variable parameters are shown in Table 13A.

TABLE 13A

Overview of gelatin particles spray-dried in a one-phase system in comparison to spray-dried in emulsion.

| Batch | Gelatin | Experiment | Yield [%] |
|---|---|---|---|
| MetP_08 | F15 | One-phase | 73.2 |
| MetP_09 | F20 | One-phase | 71.5 |
| MetP_10 | F25 | One-phase | 79.1 |
| MetP_11 | F15 | Emulsion | 3.0 |
| MetP_12 | F20 | Emulsion | 4.3 |
| MetP_13 | F25 | Emulsion | 12.8 |

Yields depended on the type of system to be sprayed; thus, the yields for gelatin particles spayed in emulsion were lower than for gelatin particles sprayed as single-phase. Without being bound by theory, it is believed that a reduction of emulsifier content might lead to an increase in yield.

Figure 17A:
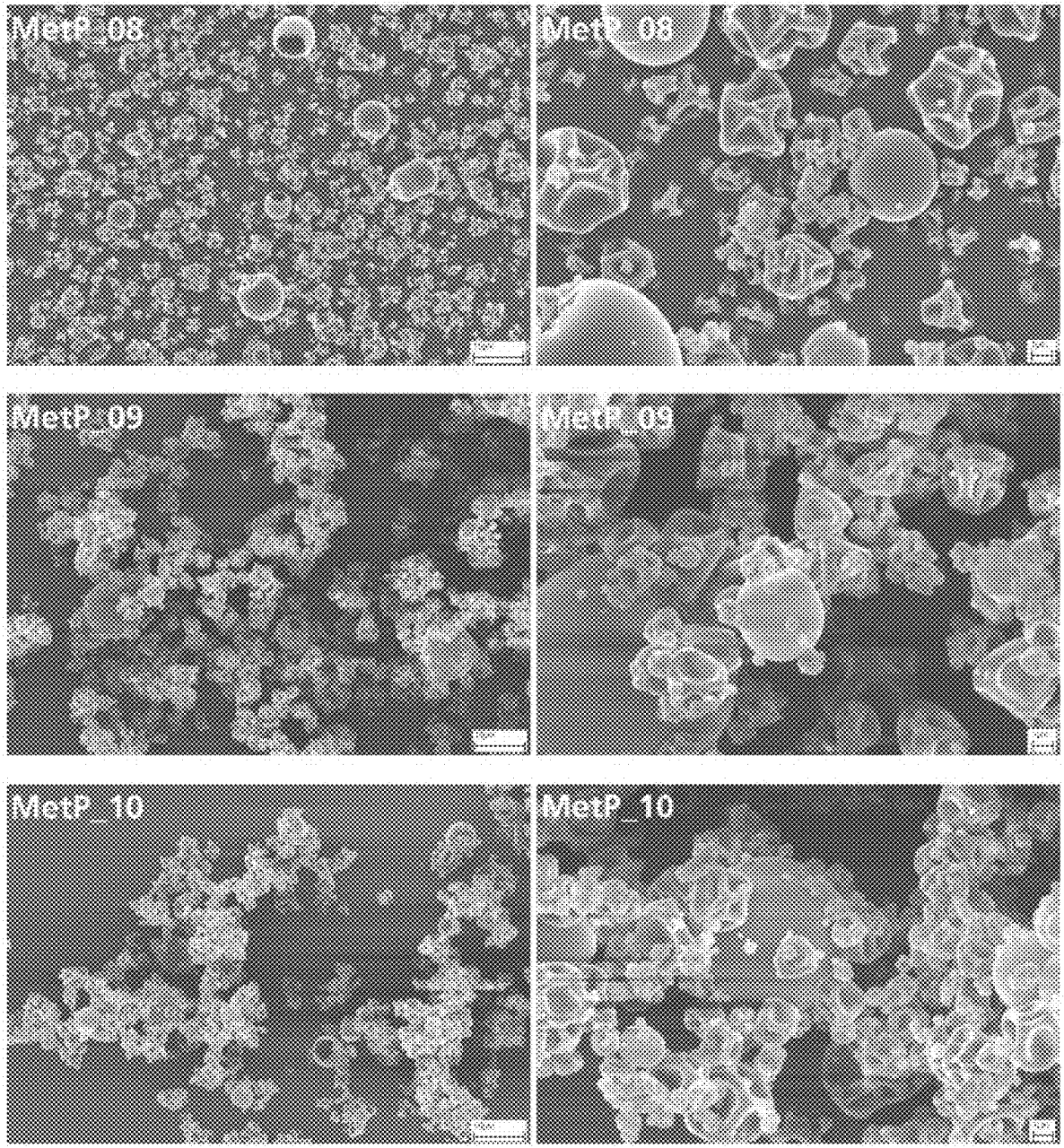
FIG. 17 (FIGS. 17A-B) shows scanning electron micrographs of spray dried compositions as described herein with testosterone and gelatin.
Figure 17B:
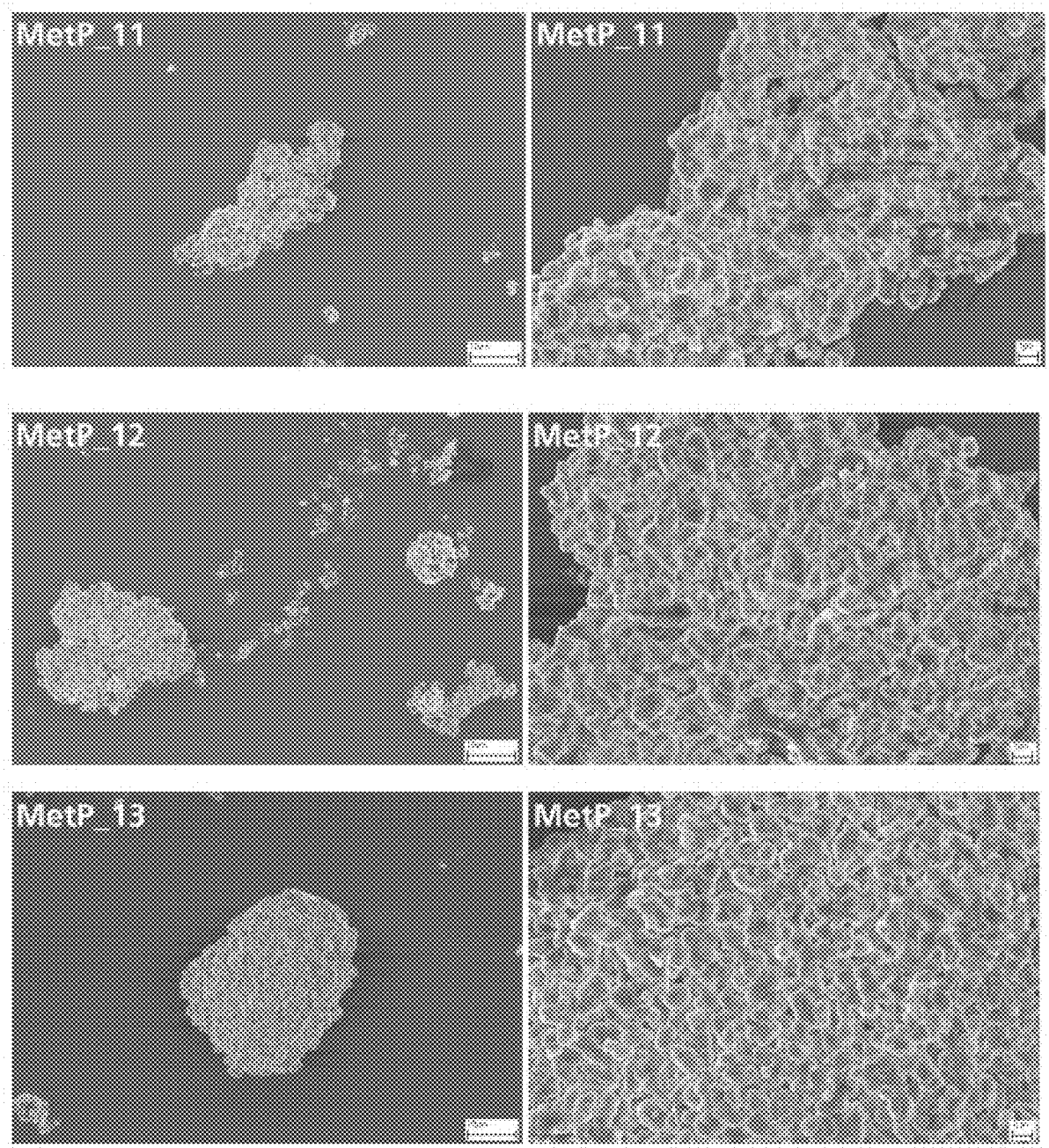

The morphology of the particles are shown in the SEM images in FIGS. 17A-B. Particles sprayed as single-phase (pure gelatin/water solution) and the particles sprayed as an emulsion possessed different morphologies. In particular, agglomerates were formed from smaller primary particles as an emulsion during spray drying processes, whereas individual particles with relatively a broad particle size distribution were produced by single-phase spraying.

Emulsifiers LUTROL® F68 and sodium oleate were tested as substitutes for TWEEN® 20 in compositions obtained with F25 gelatin. Casein was also tested as an emulsifier, but it did not dissolve in either water or dichloromethane. The parameters of the Mini Spray Dryer remained unchanged from the last experiments and the variable parameters are shown in Table 13B.

TABLE 13B

Parameters of the spray-drying experiments in emulsion with variable emulsifier and variable amount of emulsifier and the resulting yields.

| Batch | Gelatin | Emulsifying agent | Emulsifying agent (g) | Yield (%) |
|---|---|---|---|---|
| MetP__14 | F15 | TWEEN ® 20 | 0.08 | 3.4 |
| MetP__15 | F15 | TWEEN ® 20 | 0.04 | 4.2 |
| MetP__16 | F20 | TWEEN ® 20 | 0.08 | 3.8 |
| MetP__17 | F20 | TWEEN ® 20 | 0.04 | 3.7 |
| MetP__18 | F25 | TWEEN ® 20 | 0.08 | 2.8 |
| MetP__19 | F25 | TWEEN ® 20 | 0.04 | 14.0 |
| MetP__23 | F25 | Sodium oleate | 0.04 | 46.9 |
| MetP__24 | F25 | LUTROL ® F68 | 0.04 | 3.2 |

While a relatively high yield was obtained with sodium oleate as an emulsifier, the emulsifier gelled shortly after emulsification. Following the spraying there was also gelled residue in the collection vessel. For the most part, reducing the amount of emulsifier or changing the emulsifier used did not significantly alter the yield. Without being bound by theory, it is believed that the yields in Table 13 were increased by spray-drying the compositions in a single phase.

Figure 18:
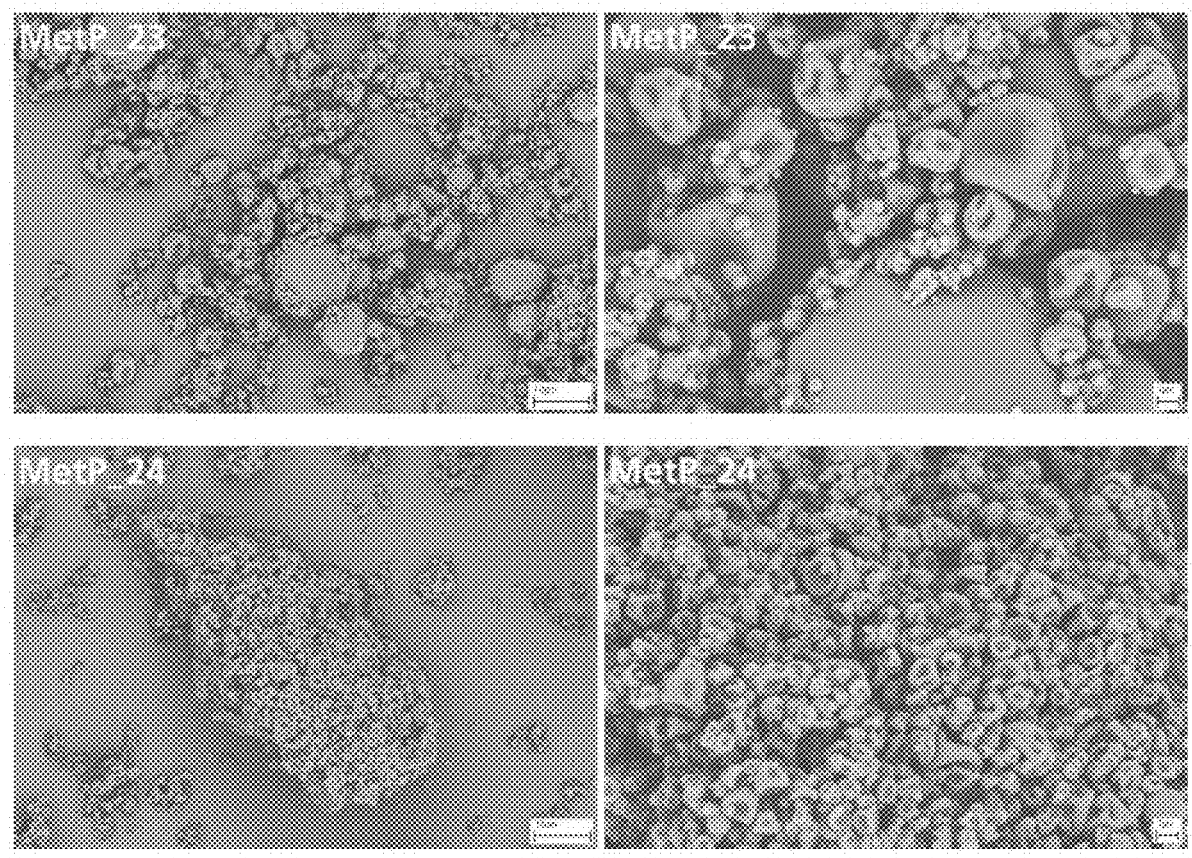
FIG. 18 shows scanning electron micrographs of spray dried compositions as described herein with testosterone, gelatin, and an emulsifying agent.
Figure 19A:
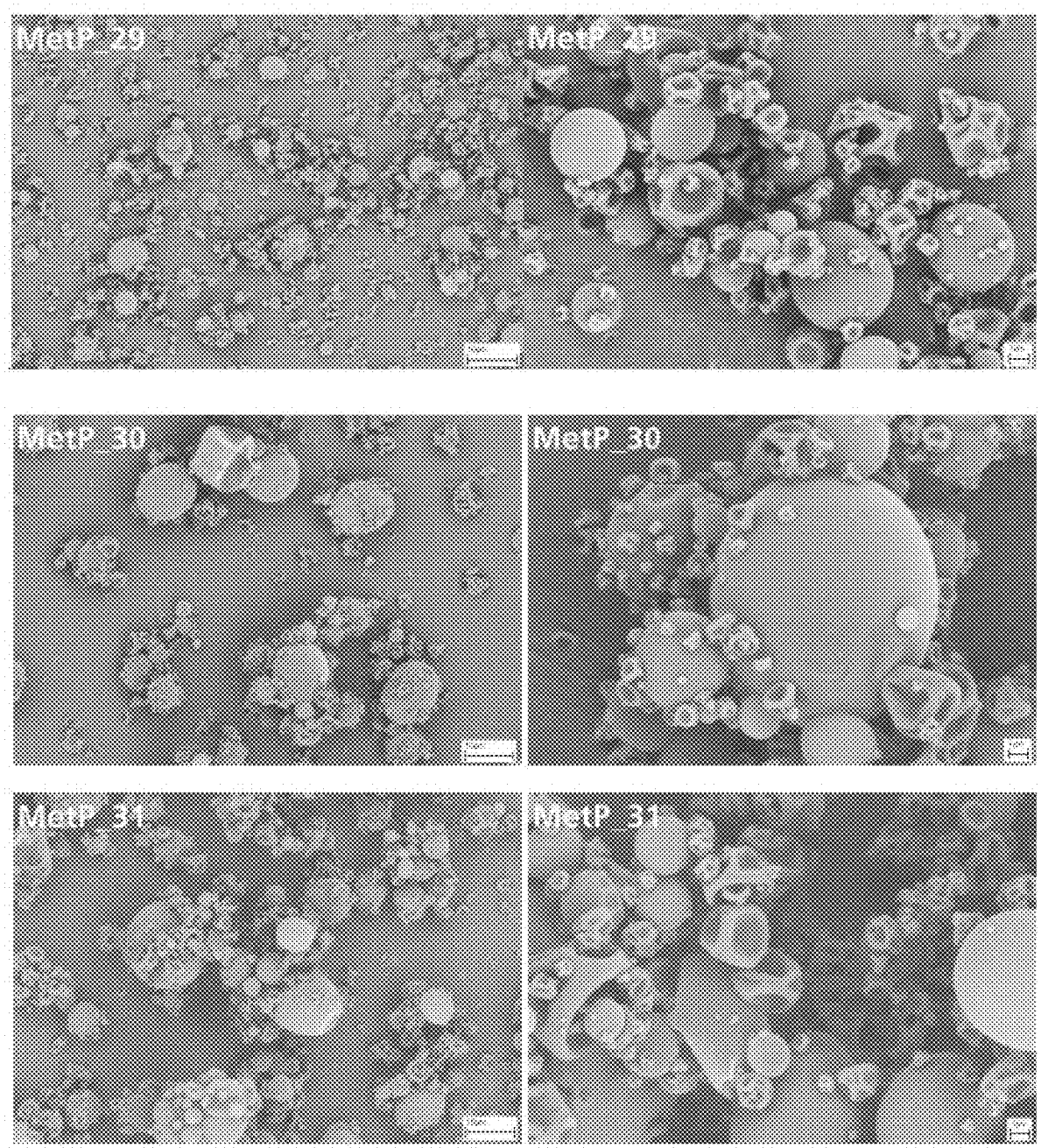
FIG. 19 (FIGS. 19A-E) shows scanning electron micrographs of gelatin particles sprayed in ethanol/water mixtures with various ethanol:water ratios.
Figure 19B:
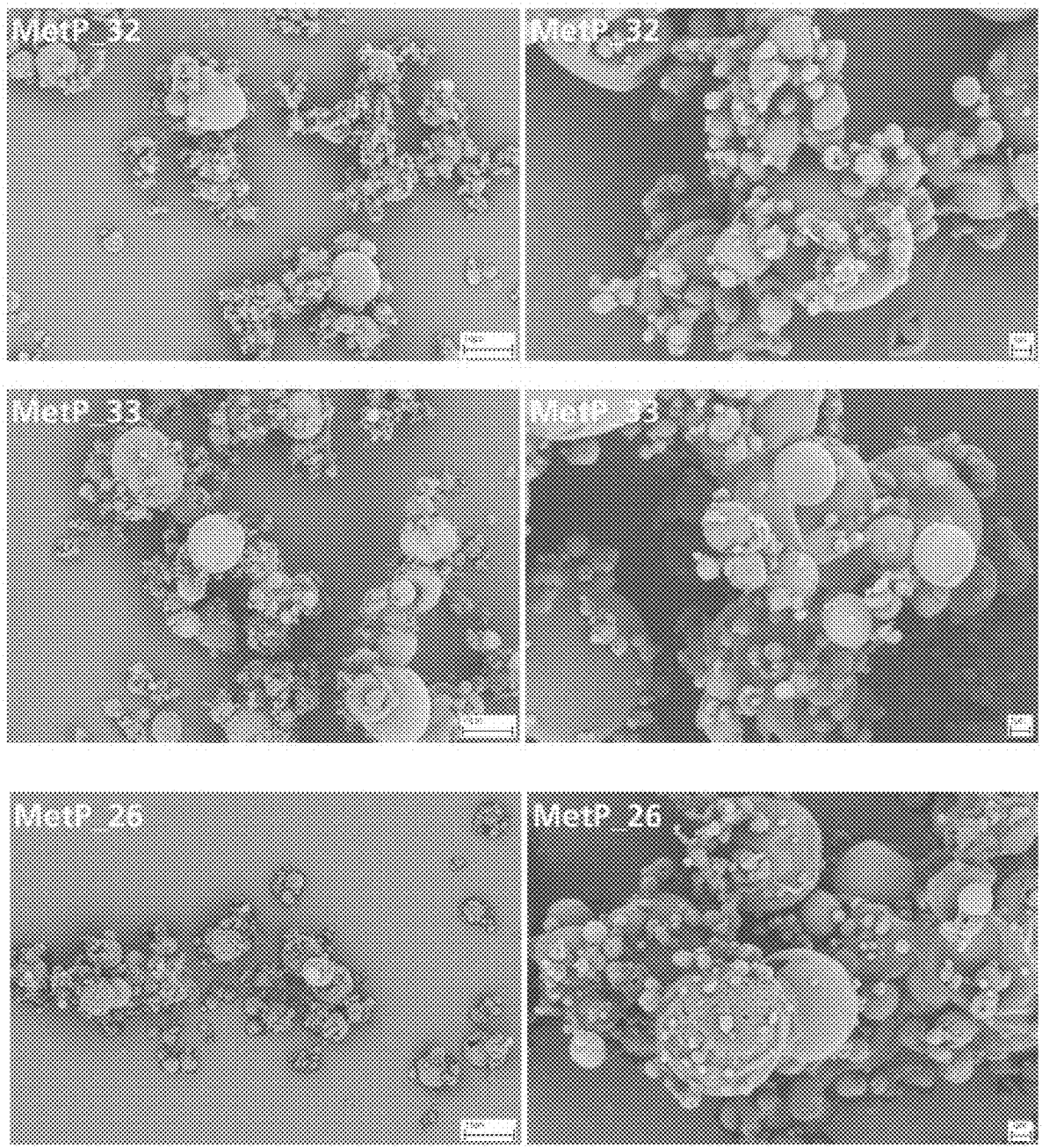
Figure 19C:
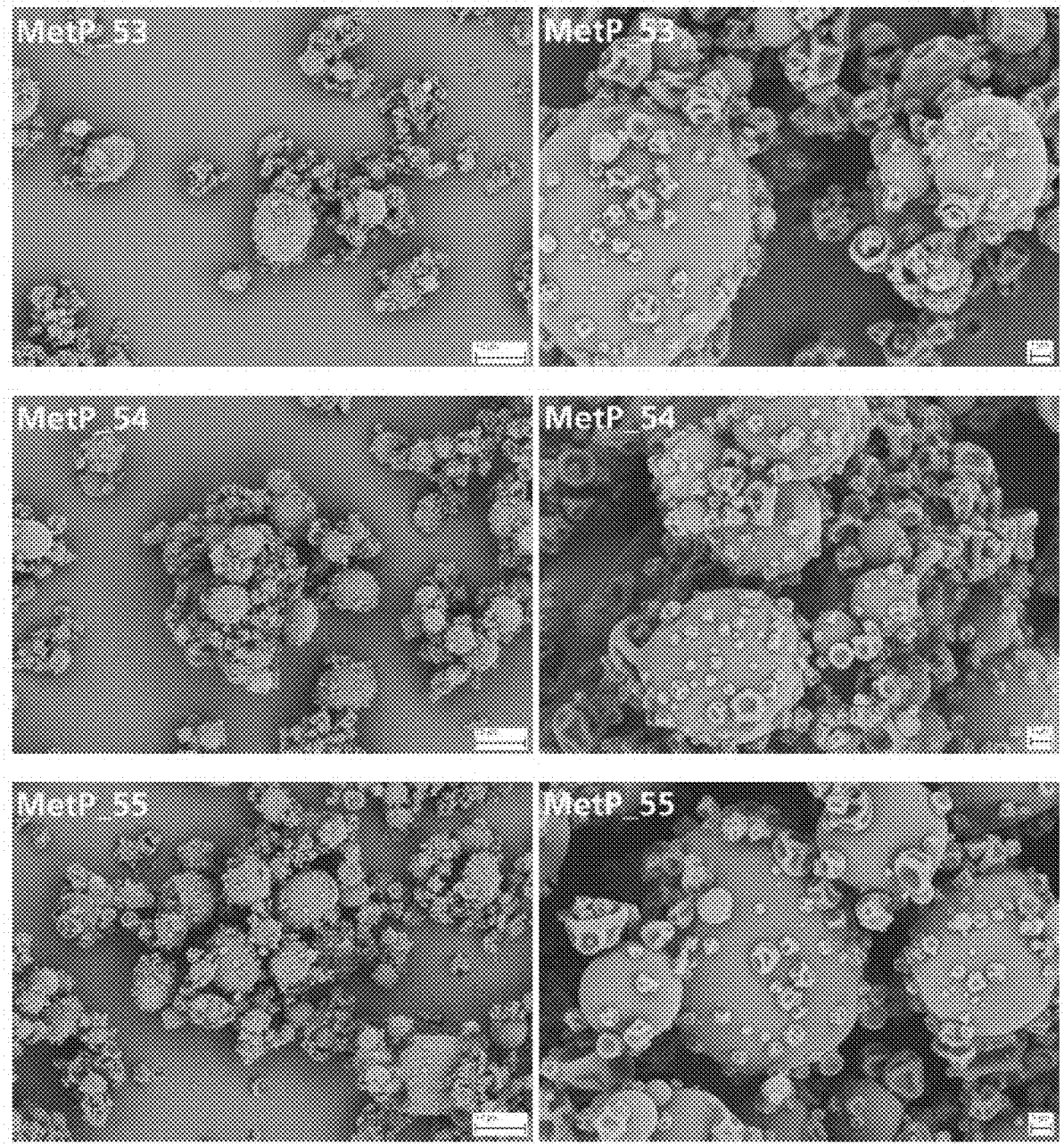
Figure 19D:
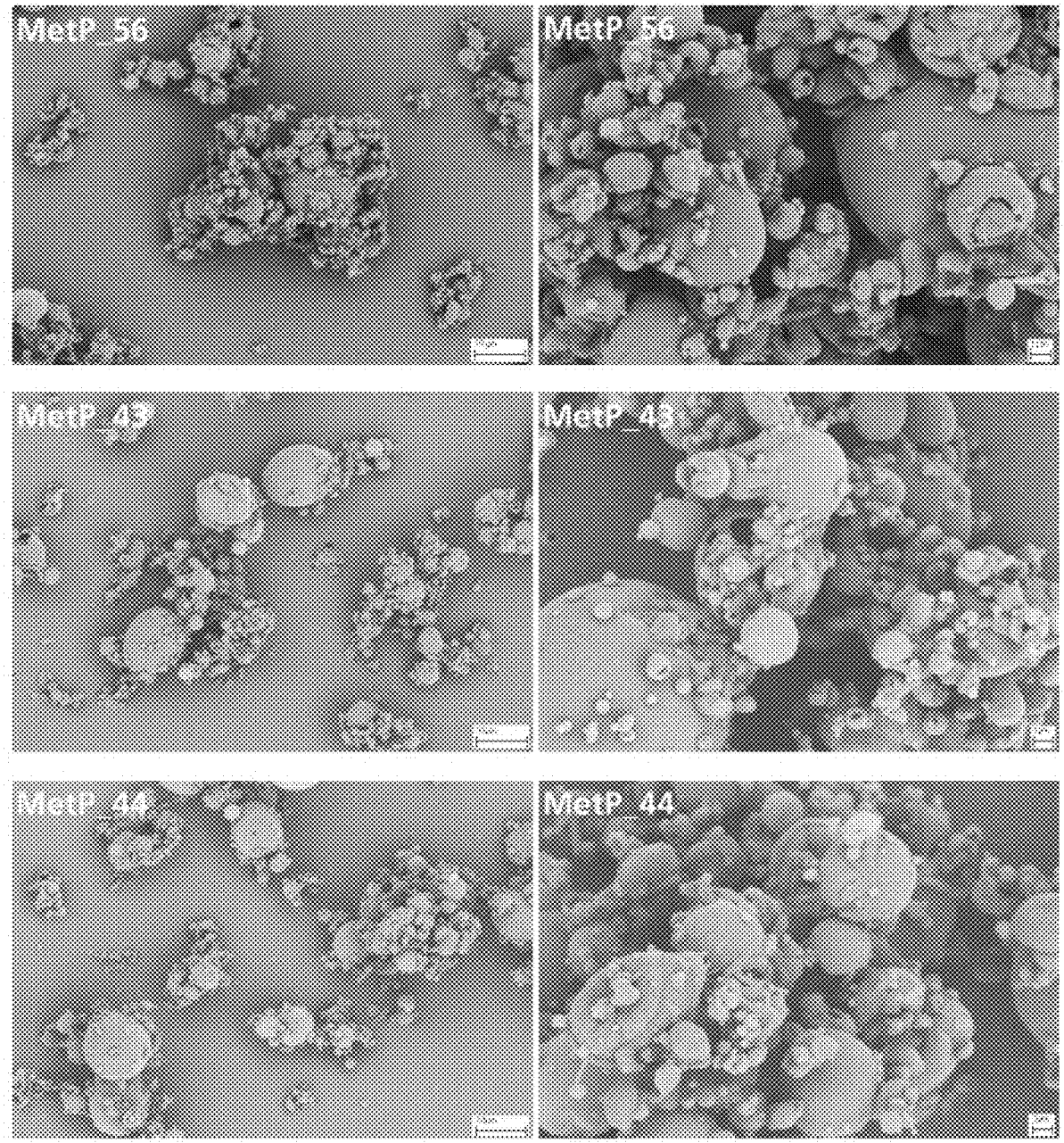
Figure 19E:
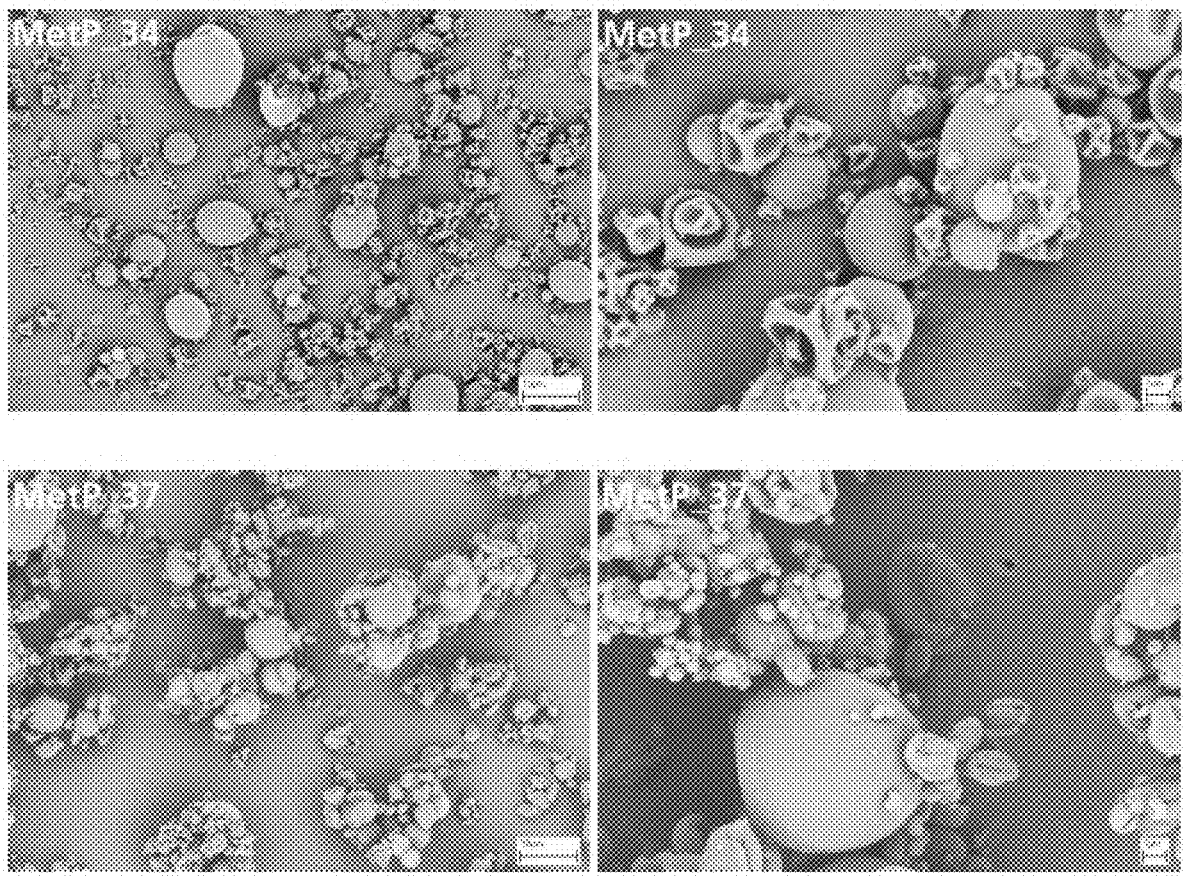

The reduction of TWEEN® 20 likewise had no influence on the morphology of the particles. The morphology of the particles with sodium oleate and LUTROL® are shown in the SEM images of FIG. 18.

Single Phase Spray Drying of Testosterone Compositions

To determine the optimal water/ethanol mixture for single-phase spraying of both testosterone and gelatin, which have differing solubility properties, compositions were sprayed in various ethanol/water mixtures. Gelatin solutions were sprayed in ethanol/water mixtures with ratios of 40/60 (v/v), 45/55 (v/v), and 50/50 (v/v). All gelatin batches were stable in the 40/60 and 45/55 mixtures. F15 gelatin was also stable at 50/50 (v/v), but the F20 and F25 gelatin-previously dissolved in water-precipitated out of solution at the 50/50 (v/v) ratio.

Each of the experiments summarized in Table 14 used 0.5 g gelatin. Differing quantities of water were added to the gelatin for the differing mixing ratios (20 mL for 40/60, 22.5 mL for 45/55, and 25 mL for 50/50). Dissolution of the gelatin took place at 37° C. in an incubating shaker at 200 rpm for a period of at least an hour. The solution was then brought to room temperature by stirring in a magnet stirrer at 500 rpm, and each of the necessary quantities of ethanol for establishing the correct mixing ratio was added. For loading of testosterone, a small quantity of ethanol was added to the gelatin solution and then the dissolved testosterone was added to obtain the correct mixing ratio.

The solutions were subsequently sprayed in the Mini Spray Dryer using a two-fluid nozzle in a closed system of suction. Settings remained constant with aspirator power 100%, dispersion gas 45 mm, nozzle cleaner at 1, pump power at 10%, and entry temperature $T_{in}$ of 135° C. The variable parameters are shown in Table 14.

TABLE 14

Parameters of the spray-drying experiments with gelatin in different ethanol-water mixtures.

| Batch | Gelatin | EtOH/H2O [v/v] | Theoretical loading (testosterone) [%] | Yield [%] |
|---|---|---|---|---|
| MetP__29 | F15 | 40/60 | — | 34.1 |
| MetP__30 | F20 | 40/60 | — | 59.1 |
| MetP__31 | F25 | 40/60 | — | 62.5 |
| MetP__32* | F15 | 40/60 | 10 | 28.1 |
| MetP__33 | F20 | 40/60 | 10 | 32.8 |
| MetP__26 | F25 | 40/60 | 10 | 46.6 |
| MetP__53 | F15 | 45/55 | — | 55.5 |
| MetP__54 | F20 | 45/55 | — | 51.6 |
| MetP__55 | F25 | 45/55 | — | 55.4 |
| MetP__56 | F15 | 45/55 | 20 | 29.1 |
| MetP__43 | F20 | 45/55 | 20 | 23.0 |
| MetP__44 | F25 | 45/55 | 20 | 31.3 |
| MetP__34 | F15 | 50/50 | — | 61.2 |
| MetP__37 | F15 | 50/50 | 30 | 5.4 |

*Note:
The spray dryer was leaking, so the spraying process was stopped before completion.

The yields were considerably increased as compared to spraying in emulsion form. The yields from unloaded gelatin particles were higher than those with testosterone-loaded gelatin particles.

Possibly due to the higher ethanol content of compositions with a 45/55 (v/v) ethanol/water ratio, a higher theoretical testosterone load of 20% was also able to be achieved. Only a 10% load of testosterone was possible in the 40/60 (v/v) ethanol/water mixture, potentially due to its poor solubility. In the case of F15 gelatin (MetP_34 and MetP_37), an ethanol/water mixture of 50/50 (v/v) could be employed and thus a theoretical load of 30% (MetP_37) achieved.

FIGS. 19A-E show the SEM images of the gelatin particles that were sprayed in ethanol/water. For the particles produced in the ethanol/water 40/60 (v/v) mixture, no clear differences were observed in the particle size distributions between the various experimental approaches. Only the particles from the unloaded approach using F15 gelatin (MetP_29) appeared to be somewhat smaller in size. Bacteria were detected in the SEM images of the testosterone-loaded particles produced with the 45/55 (v/v) ethanol/water mixture (MetP_56, MetP_43 and MetP_44), highlighting the importance of using sterile gelatin under sterile conditions. Compositions produced in ethanol/water 50/50 (v/v) show no significant differences compared to those particles produced using the other mixing ratios.

At all water/ethanol ratios, a broad particle size distribution was observed. A difference in the surface morphology between gelatin particles unloaded and loaded with testosterone was observed across all the ethanol/water mixing ratios. In particular, the smaller particles of the individual unloaded batches displayed denting, whereas this is not the case with the smaller particles of the testosterone-loaded batches.

Example 14—Loading of Testosterone in Porous Silica Microparticles

Figure 20A:
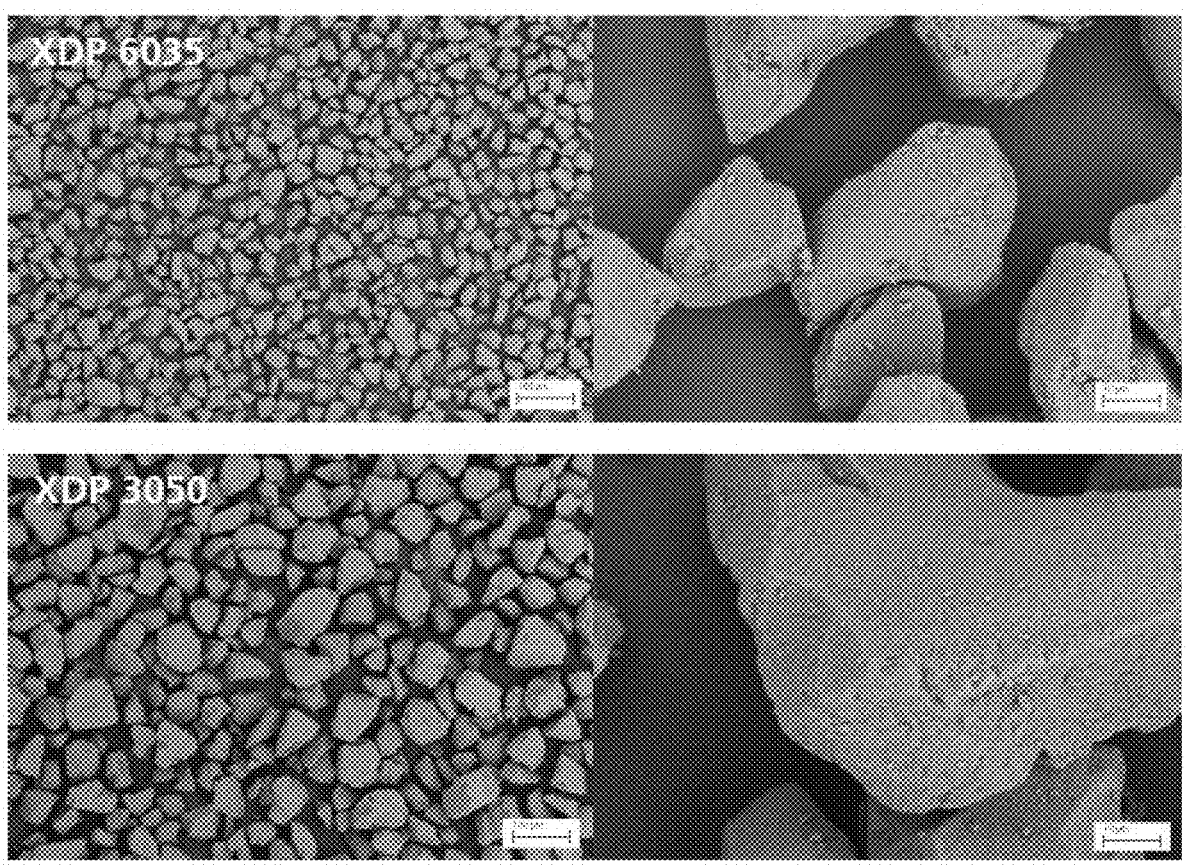
FIG. 20 (FIGS. 20A-B) shows scanning electron micrographs of spray dried mesoporous silica particles.
Figure 20B:
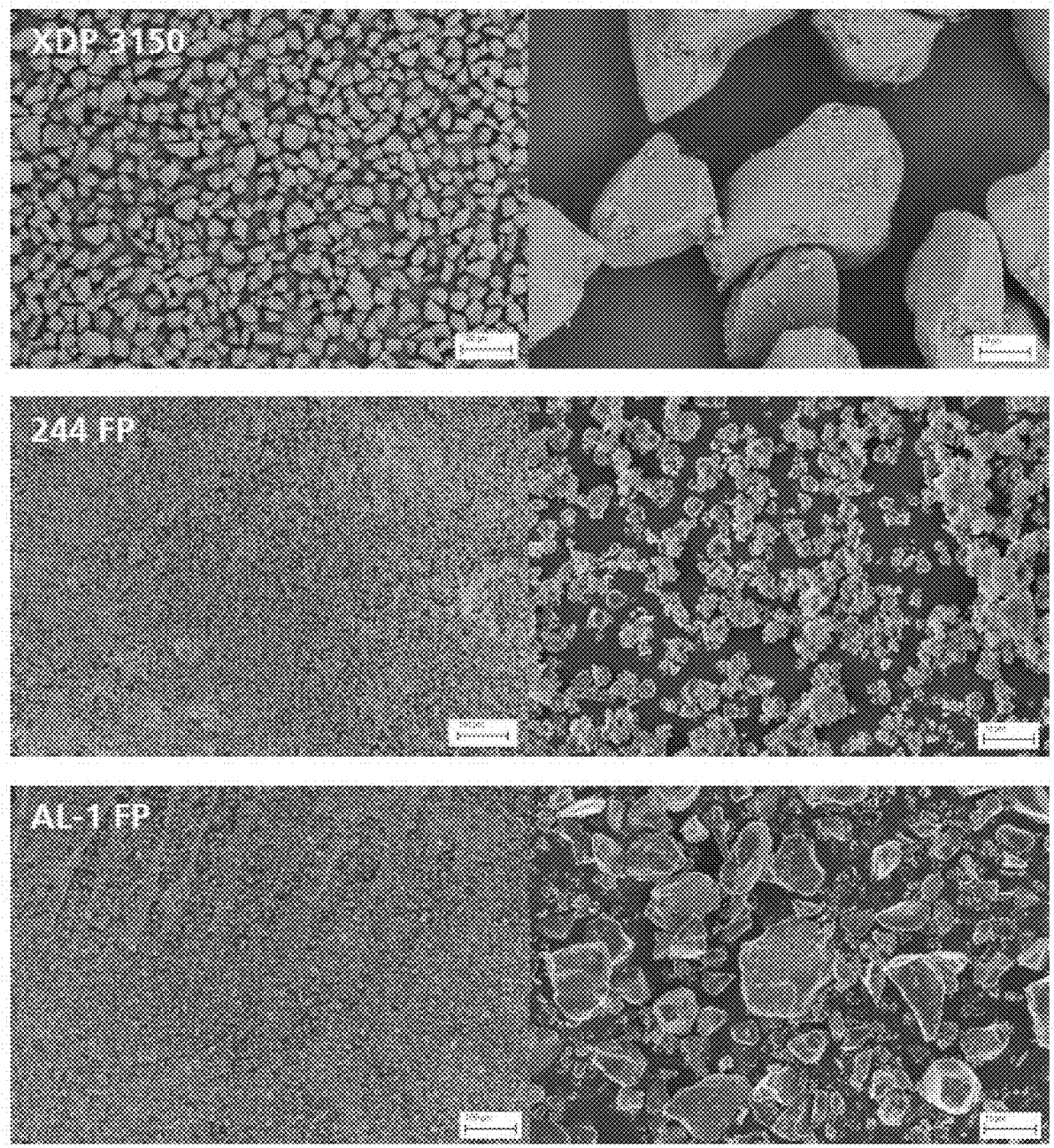
Figure 21A:
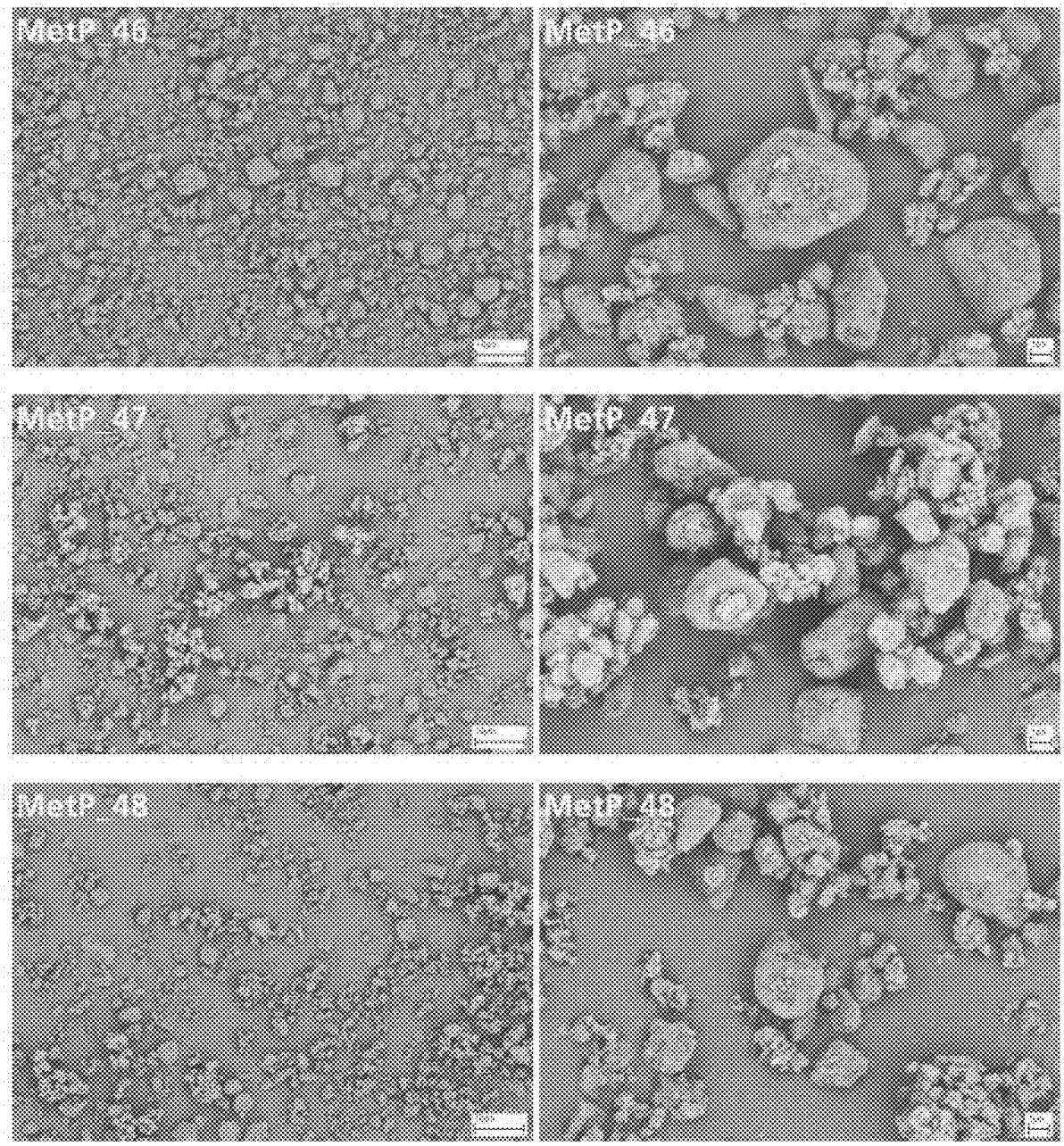
FIG. 21 (FIGS. 21A-E) shows scanning electron micrographs of spray dried mesoporous silica particles, some of which are loaded with testosterone as described herein.
Figure 21B:
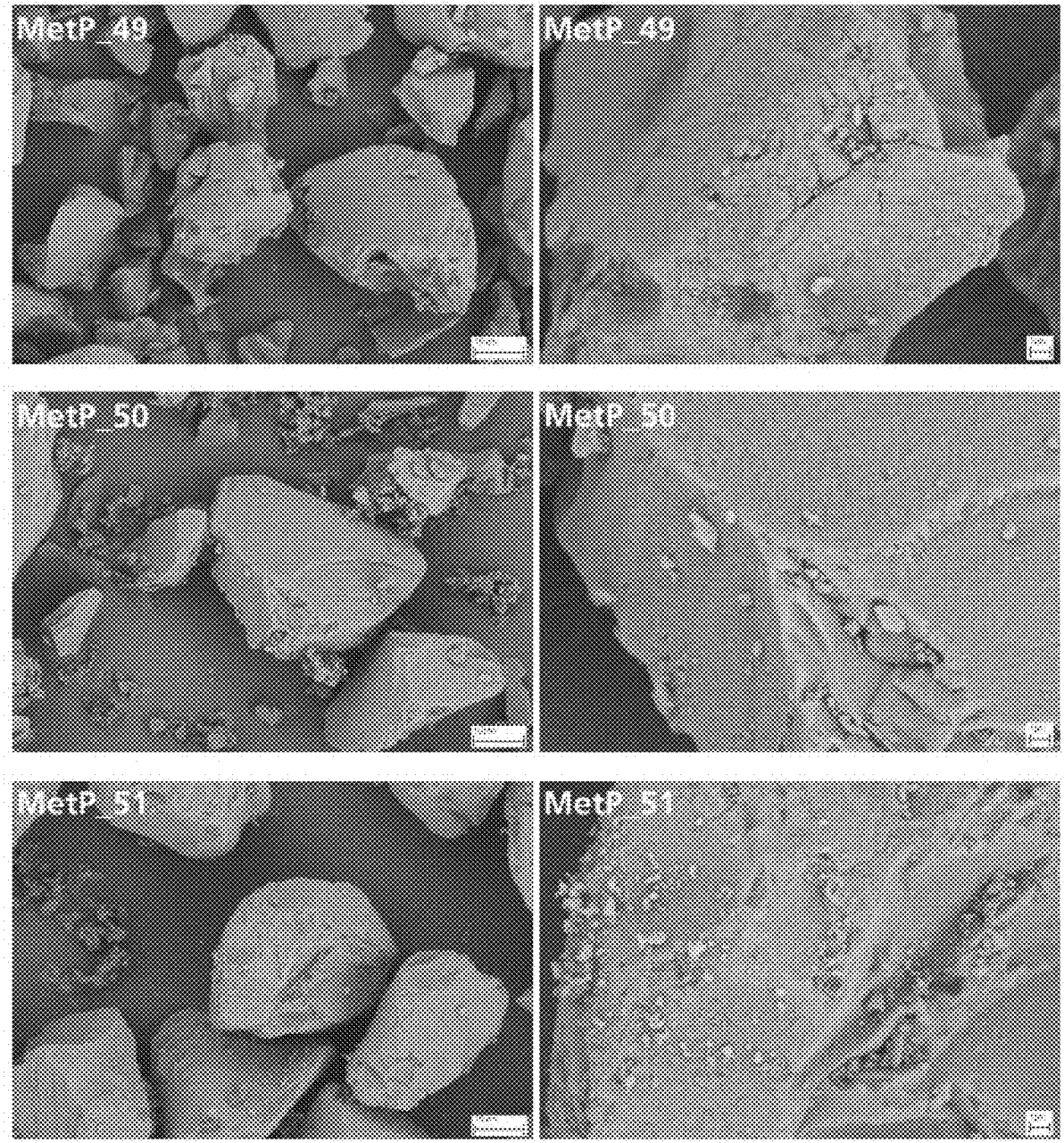
Figure 21C:
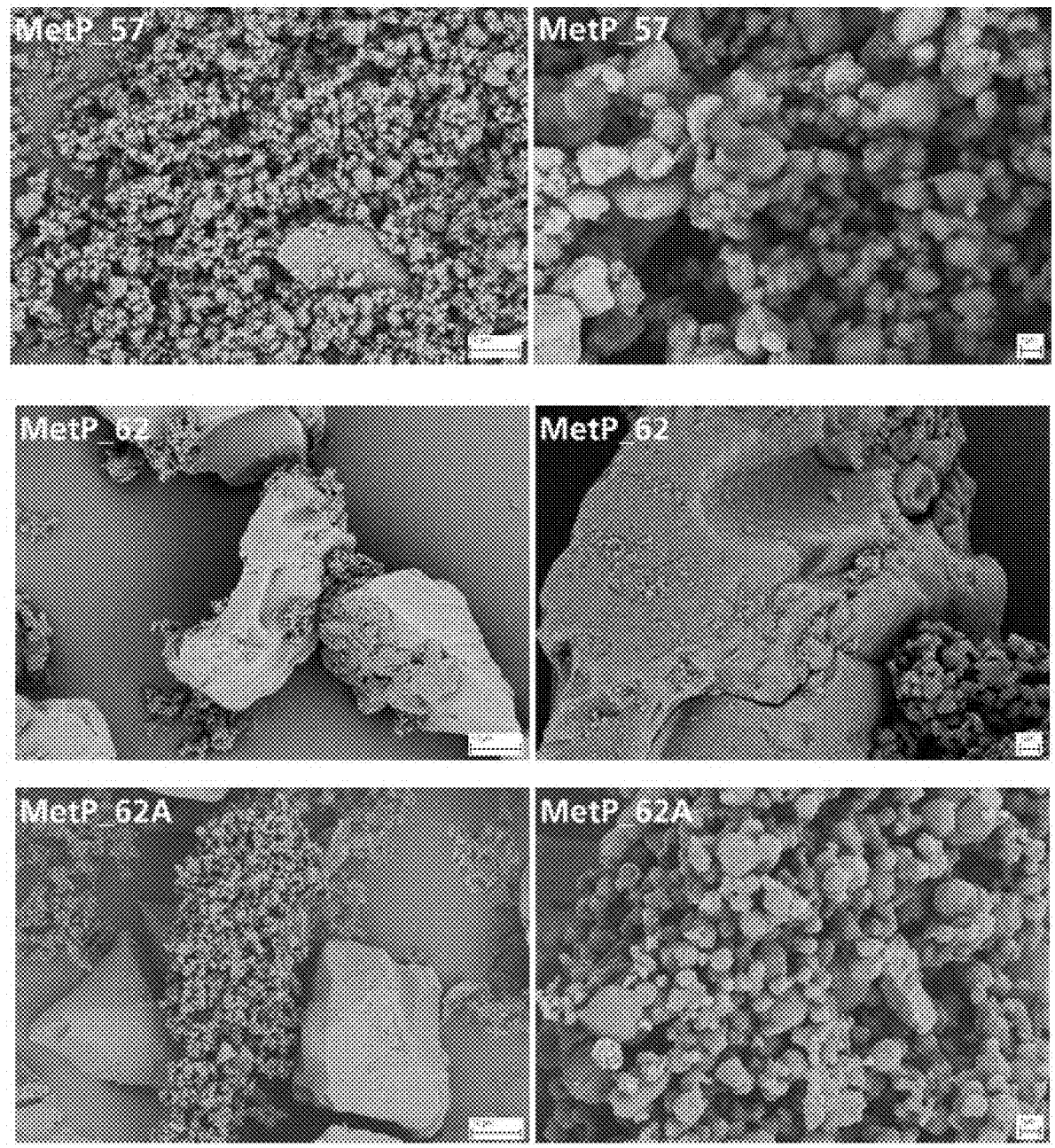
Figure 21D:
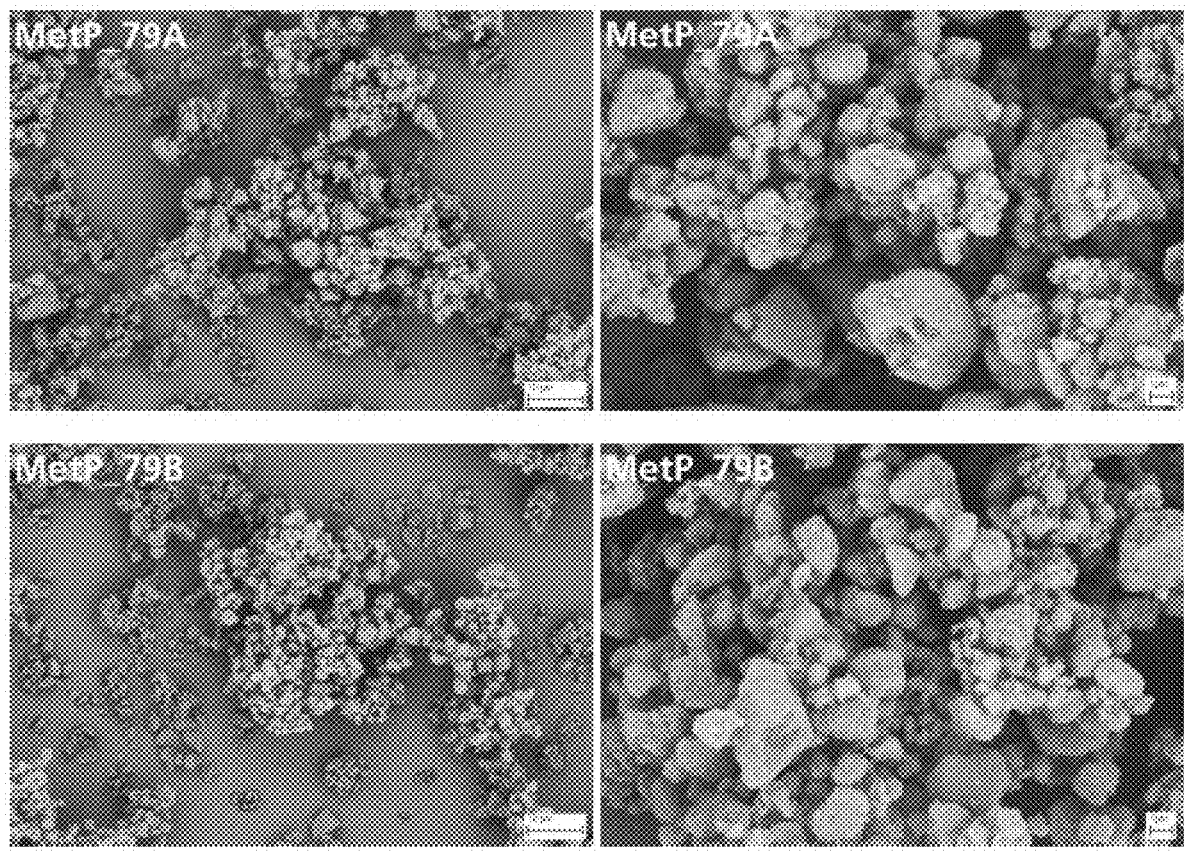
Figure 21E:
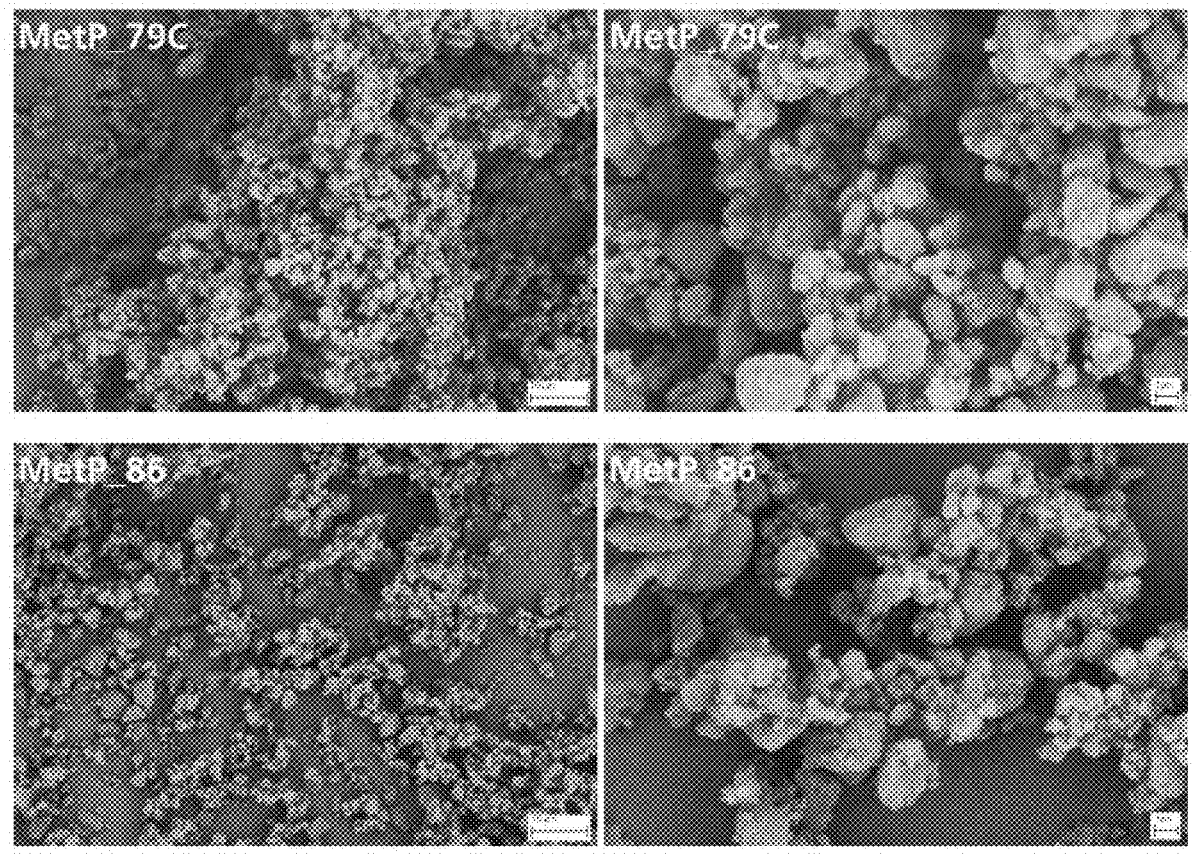

Various mesoporous silica particles (SYLOID®, from Grace) were used to encapsulate testosterone. Properties of the mesoporous silica particles are shown in Table 15. The morphology of the particles are shown in the SEM images of FIGS. 20A-B.

TABLE 15

SYLOID ® particles, particle size, pore volume and specific surface area.

| Particles | Average particle size (μm) | Average pore volume (mL/g) | Specific surface area (m²/g) |
|---|---|---|---|
| SYLOID ® XDP6035 | 35.1 | 0.98 | k.A. |
| SYLOID ® XDP3050 | 48-66 | >1.70 ml/g | 320 |
| SYLOID ® XDP3150 | 120-170 | >1.70 ml/g | 320 |
| SYLOID ® 244FP | 3.4 | 1.6 | 300 |
| AL-1FP/63 FP | 7.5 | 0.4 | 700 m2/g |

The active agent testosterone originated from two separate batches (termed "first delivery" and "second delivery"). Loading experiments were carried out with both of the deliveries. SYLOID® particles were dispersed in ethanol at a level of 1% (i.e. 1 g to 100 mL). In compositions with testosterone, the testosterone (either 100/% or 30% in relation to the total mass, i.e. testosterone+SYLOID®) was dissolved in a portion of the ethanol, and then subsequently added to the particle dispersion system. The particle mixtures were stirred with a magnetic stirrer at 500 rpm, and then sprayed with a two-fluid nozzle in a closed suction system using the B-290 Mini Spray Dryer (Büchi).

The parameters of the Mini Spray Dryer remained constant with an entry temperature of 110° C., 100% aspirator power, 100% aspirator power, dispersion gas at 45 mm and the nozzle cleaner at 1. The solution was stirred at 200 rpm during the spraying process. The variable parameters are shown in Table 16.

TABLE 16

Parameters of the spray-drying experiments with SYLOID ® particles and their yields.

| Batch | SYLOID ® | Volume of batch (mL) | Incubation time (h) | Theoretical testosterone loading (%) | Yield (%) |
|---|---|---|---|---|---|
| MetP_46 | 244FP | 50 | 1 | — | 60.1 |
| MetP_47 | 244FP | 50 | 1 | 10 | 62.8 |
| MetP_48 | 244FP | 50 | 1 | 30 | 62.0 |
| MetP_49 | XDP6035 | 50 | 1 | — | 54.8 |
| MetP_50 | XDP6035 | 50 | 1 | 10 | 94.7 |
| MetP_51 | XDP6035 | 50 | 1 | 30 | 63.0 |
| MetP_57 | 244FP | 100 | 1 | 30 | 56.1 |
| MetP_62 | XDP6035 | 100 | 1 | 30 | 66.0 |
| MetP_62A | XDP6035 | 100 | 1 | 30 | 66.2 |
| MetP_79A* | 244FP | 50 | 1:45 | 10 | 41.4 |
| MetP_79B | 244FP | 50 | 3:35 | 10 | 51.7 |
| MetP_79C | 244FP | 50 | 24:20 | 10 | 59.5 |
| MetP_86 | 244FP | 100 | ~24 | 30 | 63.2 |

*Could not be completely spray dried, because a test tube in the spray dryer was leaking.

With SYLOID® 244FP (MetP_46 to MetP_48), the presence of testosterone did not substantially impact the yield. With the larger SYLOID® XDP6035 particles (MetP_49 to MetP_51) particles, the yields were variable, but were still satisfactory.

With MetP_79A to MetP_79C, the incubation period of the SYLOID® particles with testosterone was varied prior to spray drying to allow additional time for adsorption of the testosterone if needed. MetP_62 and MetP_62A were spray dried under analogous conditions, and they demonstrate a high level of reproducibility of the spray drying process. The yields were 66.0% and 66.2%, respectively.

The morphology of the particles are shown in the SEM images of FIGS. 21A-E. In the SEM images of the SYLOID® XDP6035 particles sprayed in the presence of testosterone (MetP_50 and MetP_51) both large particles (characteristic of the particle batch) and smaller particles were observed. Without being bound by theory, it is believed that the smaller particles might result from fragments of SYLOID® particles generated by the spraying process or particulate testosterone. Due to the small size of the SYLOID® 244FP particles (MetP_46 to MetP_48), it was not feasible to determine from the SEM images whether testosterone was separately present. However, in differential scanning calorimetry experiments, MetP_51 was shown to contain crystalline testosterone.

Loading of Testosterone—Second Delivery (i.e., Second Batch)

SYLOID® 244FP particles and AEROSIL® 200 particles were used to encapsulate testosterone. The SYLOID® particles or AEROSIL® particles were dispersed in ethanol at a level of 1% (i.e. 1 g to 100 mL). In compositions with testosterone, the testosterone (either 30% or 40% in relation to the total mass, e.g., testosterone+SYLOID®) was dissolved in a portion of the ethanol, and then subsequently added to the particle dispersion system. The particle mixtures were stirred with a magnetic stirrer at 500 rpm, and then sprayed with a two-fluid nozzle in a closed suction system using the B-290 Mini Spray Dryer (Büchi). The entry temperature was varied and dropped to 81° C. In one experiment, a 50/50 ethanol/water mixture (v/v) was used as a continuous phase in place of ethanol to increase the adsorption of the testosterone if needed. The parameters of the Mini Spray Dryer remained constant with 10% pump power, 100% aspirator power, dispersion gas at 45 mm and the nozzle cleaner at 1. The solution was stirred at 200 rpm during the spraying process. The variable parameters are shown in Table 17.

TABLE 17

Parameters of the spray-drying experiments with testosterone (second delivery) and their yields.

| Batch | Particles | Solvent | Theoretical testosterone loading (%) | $T_{in}$ (° C.) | Yield (%) |
|---|---|---|---|---|---|
| MetP_92 | 244FP | Ethanol | 30 | 110 | 58.9 |
| MetP_93 | 244FP | Ethanol | 30 | 81 | 67.4 |
| MetP_94 | 244FP | Ethanol | 40 | 81 | 67.3 |
| MetP_95 | 244FP | Ethanol/H2O 50/50 (v/v) | 30 | 110 | 71.8 |
| MetP_102 | AEROSIL ® 200 | Ethanol | 30 | 81 | 45.2 |

Figure 22:
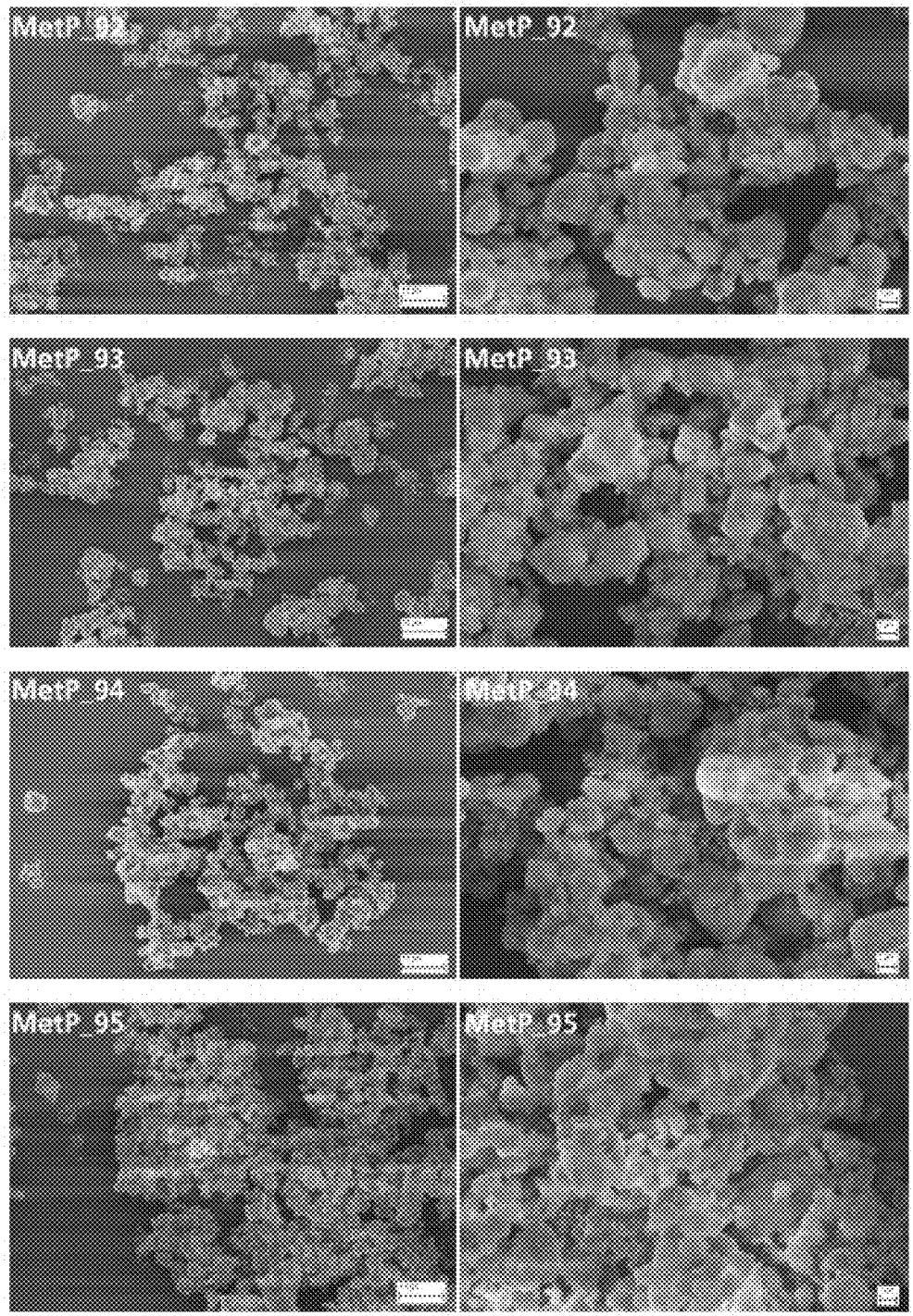
FIG. 22 shows scanning electron micrographs of compositions as described herein with testosterone and SYLOID® 244FP.
Figure 23:
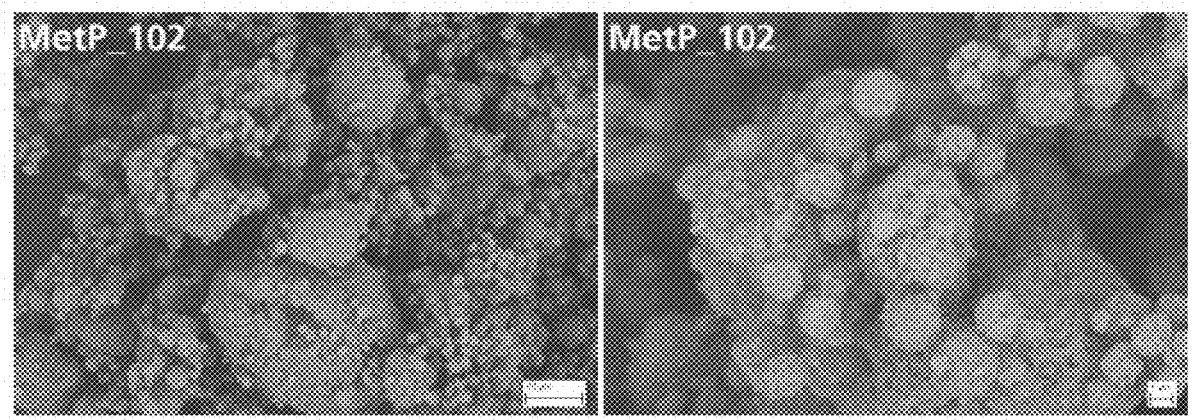
FIG. 23 shows scanning electron micrographs of compositions as described herein with testosterone and AEROSIL® 200.

Yields obtained with SYLOID® particles were between 58.9% and 71.8%, and the yield obtained with AEROSIL® 200 was 45.2%. The morphology of the loaded SYLOID® particles is shown in the scanning electron microscope images in FIG. 22. The particle morphology and particle size distribution of the two different particle batches show no significant differences. FIG. 23 shows the SEM images of testosterone in sprayed dried AEROSIL® 200 particles. The small AEROSIL® primary particles formed spherical agglomerates upon spray drying.

Loading of SYLOID® Particles Via Oil

244FP, XDP6035, and XDP3050 mesoporous silica particles (SYLOID®, from the Grace Company) were used to encapsulate testosterone. Various oils, in which testosterone displayed varying solubility, were used for loading these particles. Testosterone solubility in castor oil, linalool, TRANSCUTOL® HP, and CAPRYOL™ PGMC is set forth in Table 18.

TABLE 18

Solubility of testosterone in different oils.

| Oil | Solubility from oil (%) |
| --- | --- |
| Castor oil | 4.0 |
| Linalool | 12.5 |
| TRANSCUTOL® HP | 6.5 |
| CAPRYOL™ PGMC | 6.0 |

The miscibility of castor oil with each one of the other oils was tested. 50/50 mixtures were produced in initial experiments; that is to say, 1 g of castor oil was mixed with 1 g of each oil (linalool, CAPRYOL™, TRANSCUTOL®). It was determined that all three oils are miscible with castor oil. Spontaneous streaking occurred with all three samples, with only one phase being visible after about five minutes. Thus, the oils can also be employed as mixtures.

The adsorption ability of the SYLOID® particles was investigated by mixing SYLOID® 244FP, XDP3050, and XDP6035 with castor oil, linalool, TRANSCUTOL®, and CAPRYOL™. The maximally soluble amount of testosterone (under the conditions tested) was dissolved in 2.5 g of each oil using a vortex mixer and shaker at 1000 rpm. The periods for complete dissolving of the testosterone are shown in Table 19.

TABLE 19

Time of solubility of testosterone in different oils.

| Oil | Testosterone (g) | Time (min) |
| --- | --- | --- |
| Castor oil | 0.10 | >300 |
| Linalool | 0.31 | 15-20 |
| TRANSCUTOL® | 0.16 | ~5 |
| CAPRYOL™ | 0.15 | ~60 |

A particle/oil ratio of 1:1.5 was employed for testosterone loading the SYLOID® particles by means of oil. 0.75 g of each oil loaded with testosterone and 0.5 g of each of the SYLOID® particles were mixed and stirred with a magnetic stirrer at 700 rpm for ten minutes. The mixture was also manually mixed with a spatula, and then stirred again for 10 minutes at 700 rpm. Properties of different compositions are set forth in Table 20.

TABLE 20

Experimental batches of different particle/oil mixtures in a ratio of 1:1.5.

| Batch | Oil | SYLOID® | Texture after loading |
| --- | --- | --- | --- |
| MetP_80_R | Castor oil | 244FP | powder |
| MetP_80_L | Linalool | 244FP | powder |
| MetP_80_T | TRANSCUTOL® | 244FP | powder |
| MetP_80_C | CAPRYOL™ | 244FP | powder |
| MetP_81_R | Castor oil | XDP6035 | sticky |
| MetP_81_L | Linalool | XDP6035 | sticky |
| MetP_81_T | TRANSCUTOL® | XDP6035 | sticky |
| MetP_81_C | CAPRYOL™ | XDP6035 | sticky |
| MetP_82_R | Castor oil | XDP3050 | powder |
| MetP_82_L | Linalool | XDP3050 | powder |
| MetP_82_T | TRANSCUTOL® | XDP3050 | powder |
| MetP_82_C | CAPRYOL™ | XDP3050 | powder |

Figure 24:
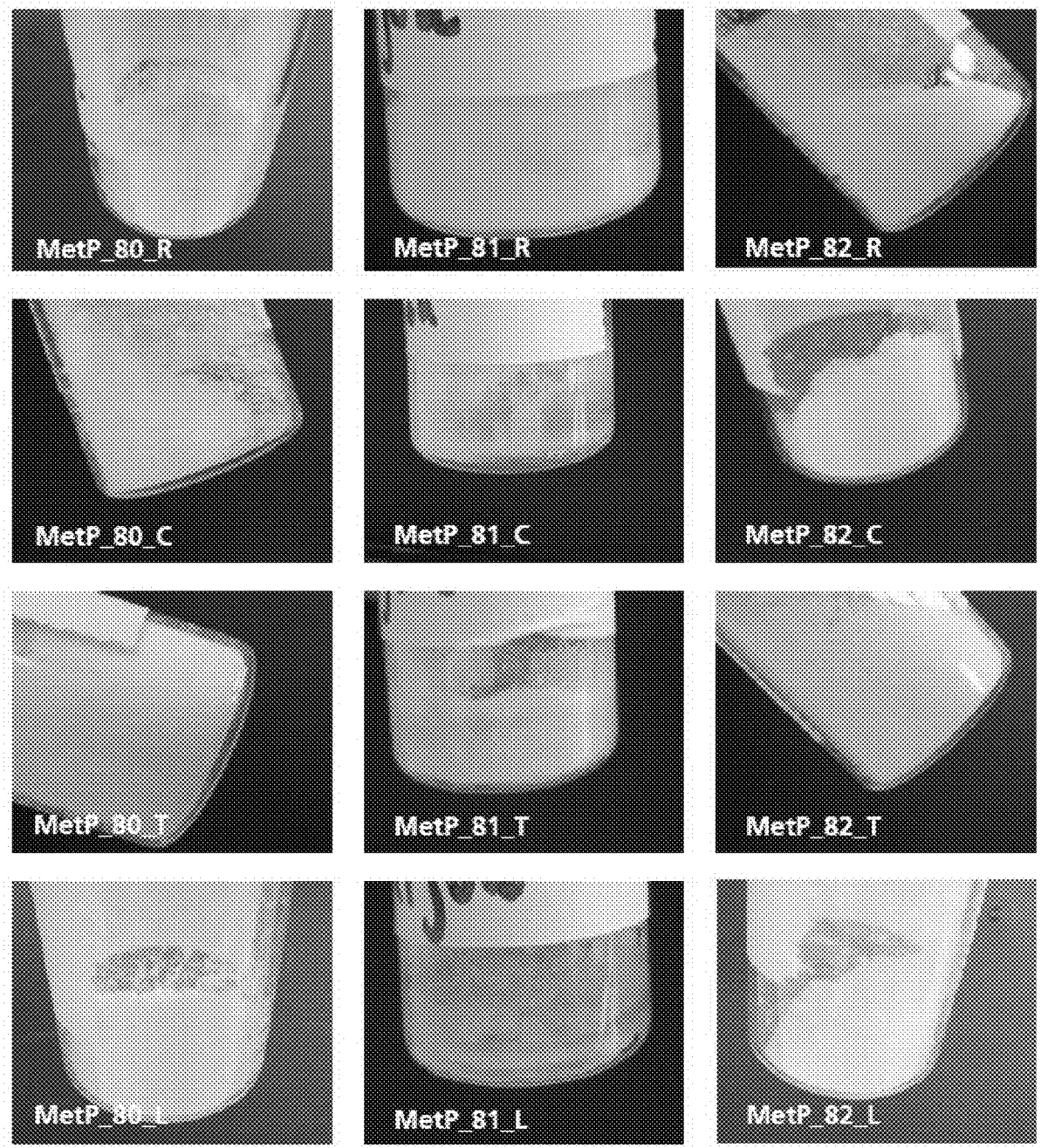
FIG. 24 sets forth pictures of various compositions as described herein with testosterone and mesoporous silica particles, and demonstrates textures associated with the various compositions.

The SYLOID® XDP6035 particles did not adsorb the oil completely and formed a sticky mass, perhaps due to their small pore volumes. The SYLOID® 244FP and XDP3050 particles were powder-like after testosterone loading. FIG. 24 demonstrates the textures of the compositions in Table 20.

To assess the effect of particle/oil ratio on degree of loading, 1.5 g of each oil was mixed with SYLOID® particles at a 1:3 particle:oil ratio and stirred in a magnetic stirrer at 700 rpm for ten minutes. The mixture was manually mixed with a spatula, and then stirred for ten more minutes of stirring at 700 rpm. Properties of different compositions are set forth in Table 21.

TABLE 21

Experimental batches of different particle/oil mixtures in the ratio 1:3.

| Batch | Oil | SYLOID® | Texture after loading |
| --- | --- | --- | --- |
| MetP_83_R | Castor oil | 244FP | sticky, glassy |
| MetP_83_L | Linalool | 244FP | sticky, clear |
| MetP_83_T | TRANSCUTOL® | 244FP | sticky, glassy |
| MetP_83_C | CAPRYOL™ | 244FP | sticky, glassy |
| MetP_84_R | Castor oil | XDP3050 | hard gel |
| MetP_84_L | Linalool | XDP3050 | clear gel |
| MetP_84_T | TRANSCUTOL® | XDP3050 | clear, hard gel |
| MetP_84_C | CAPRYOL™ | XDP3050 | clear, hard gel |

Figure 25:
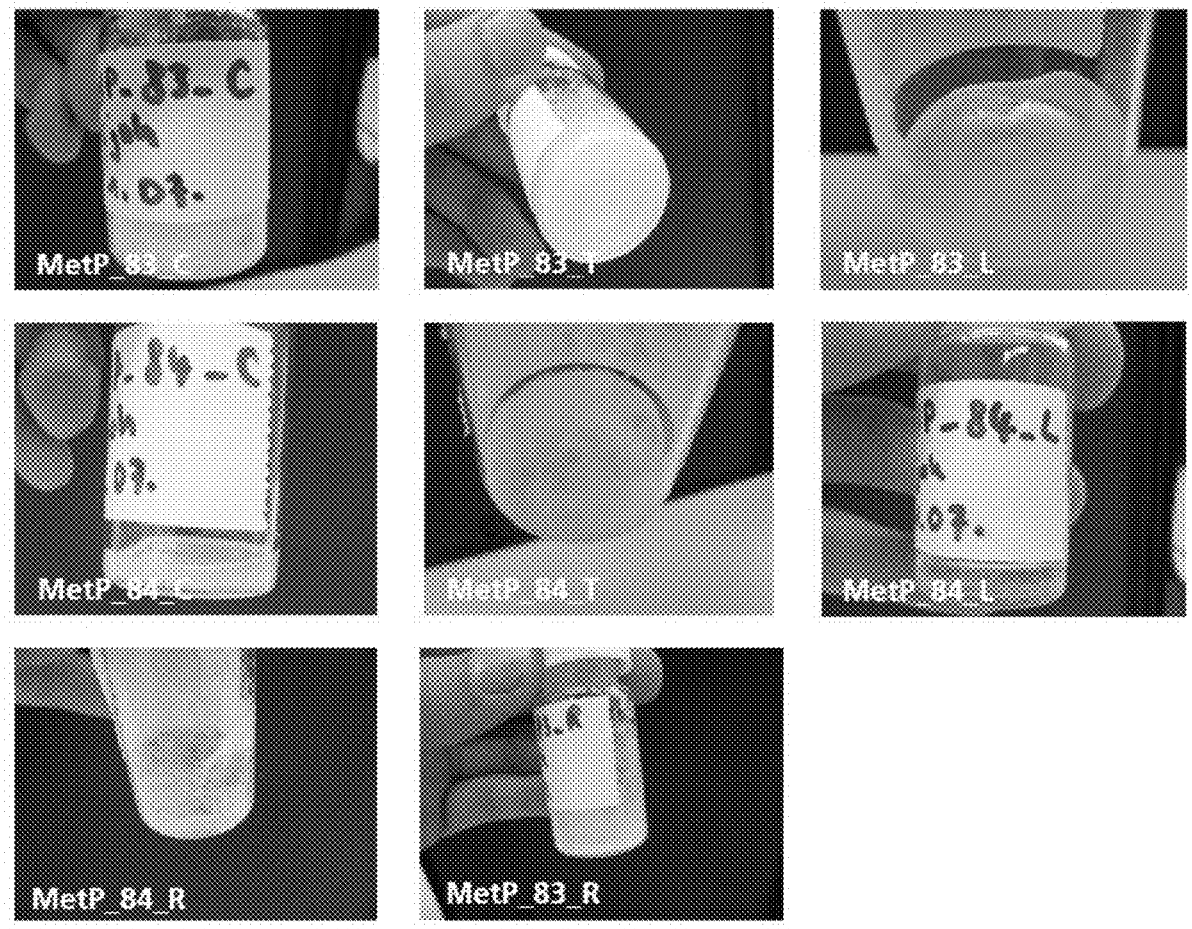
FIG. 25 sets forth pictures of various compositions as described herein with testosterone and mesoporous silica particles, and demonstrates textures associated with the various compositions.

At a particle/oil ratio of 1:3, the loaded particles were no longer powder-like, as shown in Table 21 and FIG. 25, and it is believed that the oil was not located in the particle pores. Moreover, a maximum loading level of only 9.4% testosterone was achieved with this particle:oil ratio due to the maximum solubility of testosterone in linalool.

Example 15—Synthesis of Testosterone-Loaded Core/Shell Particles

Core/shell particles of mesoporous silica particles and gelatin were synthesized to assess the ability to prepare particles with an enhanced retardation effect (i.e., delayed release of testosterone). Without being bound by theory, it is believed that unloaded gelatin can function as a barrier to delay testosterone release, while with testosterone-loaded gelatin, the gelatin can act as a substrate for the testosterone.

In the case of an unloaded gelatin matrix coating, 0.5 g of F15 gelatin was mixed with 27.5 mL of water and agitated at 200 rpm in an incubating shaker at 37° C. until completely dissolved. 22.5 mL of ethanol was added giving a 45/55 (v/v) ethanol/water ratio, the mixture was shaken for about an hour in the incubating shaker, stirred on a magnetic stirrer at 500 rpm, and then brought to room temperature. For a testosterone-loaded gelatin matrix, the gelatin was dissolved in water analogously to the unloaded gelatin. 0.125 g of testosterone was dissolved in 2 mL of ethanol and added to the gelatin mixture. 20.5 mL of ethanol was then added to the gelatin mixture.

Previously sprayed testosterone-loaded SYLOID® particles (0.25 g testosterone, from Example 1) with a 30% theoretical testosterone loading level were subsequently added to each of the gelatin solutions and stirred into the gelatin matrix. The suspension was stirred at 500 rpm until spray drying.

The particles were spray dried using a Mini Spray Dryer in a closed system in suction while stirring was continued at 500 rpm on the magnetic stirrer. The entry temperature $T_{in}$ of 135° C., the dispersion gas 45 mm, aspirator power level 100%, pump power level 10% and the nozzle cleaner at 1 were constant. The variable parameters are shown in Table 22.

TABLE 22

Parameters and results of the spray-drying experiments by using the two-fluid nozzle.

| Batch core/shell | SYLOID ®-partide | Batch SYLOID ® | Theoretical loading testosterone/ gelatin (%) | Yield (%) |
|---|---|---|---|---|
| MetP_58 | 244FP | MetP_57 | — | 70.9 |
| MetP_59 | 244FP | MetP_57 | 20 | 93.6 |
| MetP_63 | XDP6035 | MetP_62 | — | 68.7 |
| MetP_63A | XDP6035 | MetP_62 | — | 71.3 |
| MetP_64 | XDP6035 | MetP_62 | 20 | 69.1 |
| MetP_64A | XDP6035 | MetP_62 | 20 | 24.8 |
| MetP_88 | 244FP | MetP_57 | 20 | 41.3 |

Figure 26A:
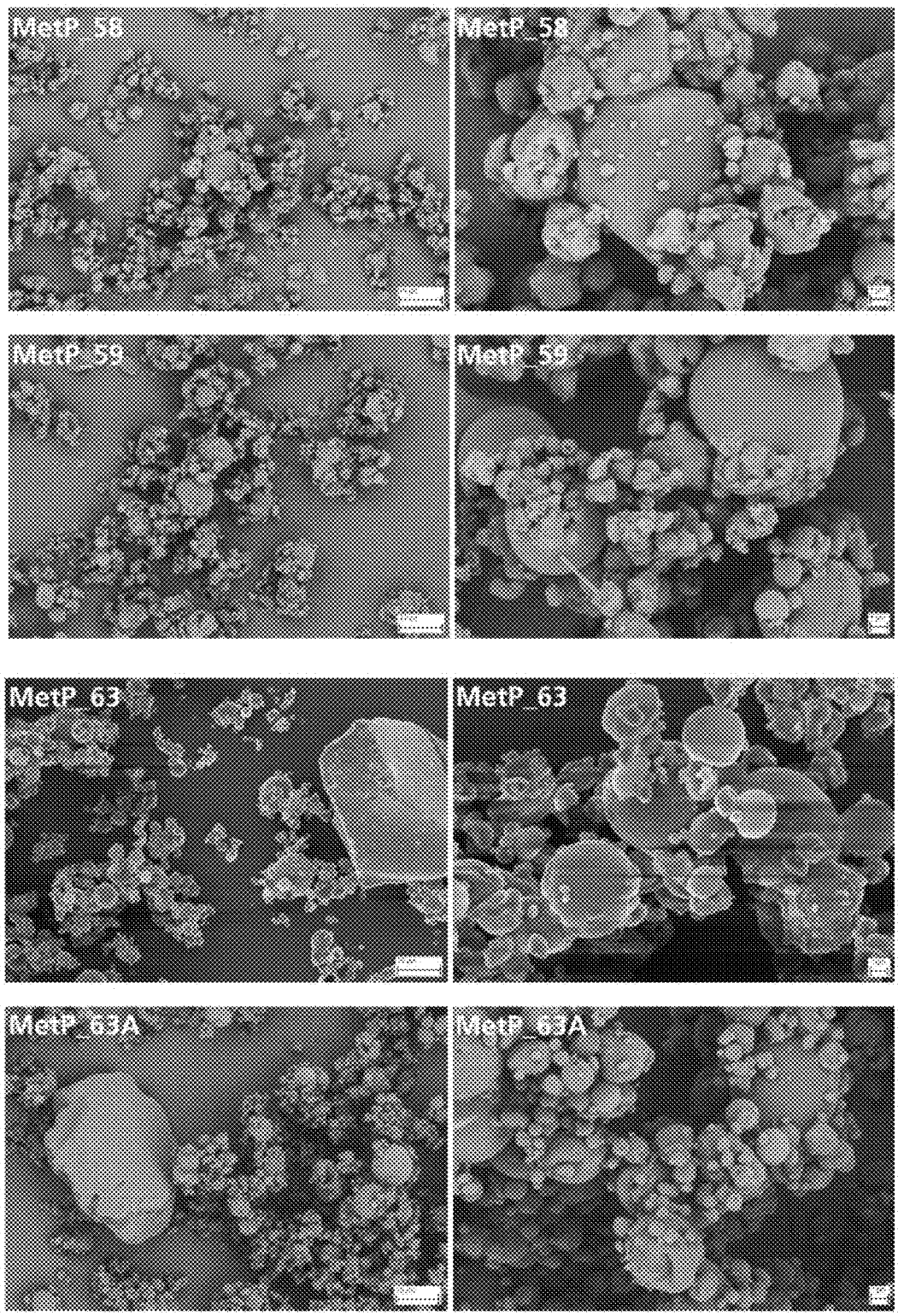
FIG. 26 (FIGS. 26A-B) shows scanning electron micrographs of mesoporous silica particles, some of which are loaded with testosterone, that were spray dried with a two-fluid nozzle.
Figure 26B:
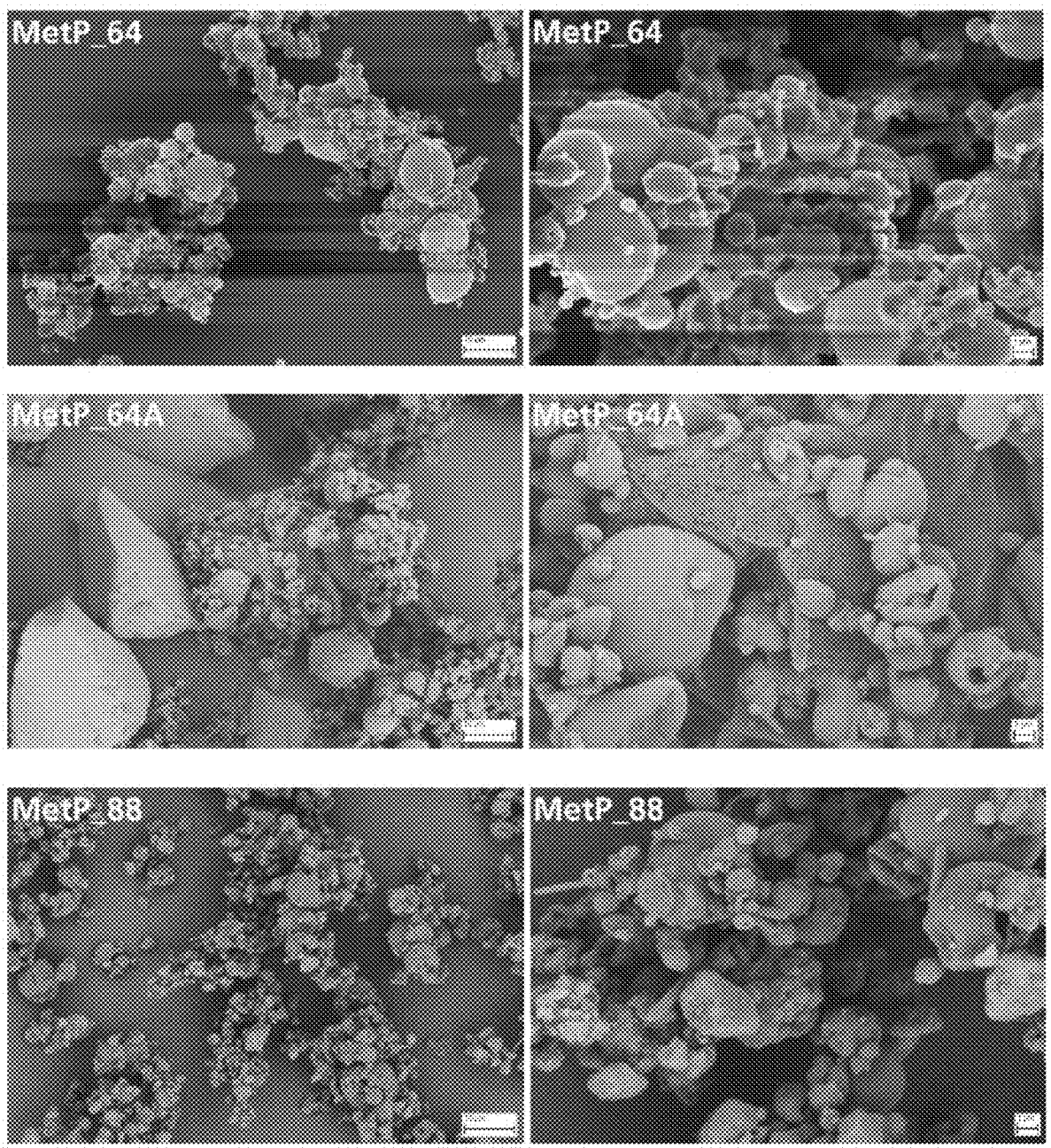

For MetP_64A and MetP_88, relatively large quantities of particles were adsorbed by the cyclone during spraying, possibly explaining the lower yields for these compositions (24.8% and 41.3%, respectively). The particles are depicted in the SEM images of FIGS. 26A-B. The differences compared to the pure testosterone-loaded SYLOID® particles (see Example 12; FIG. 14) are clear.

For spray-dried SYLOID® 244FP particles, primarily spherical particles were formed by spray drying in the presence of gelatin. Very few particles still displayed open pores, and irregularly shaped SYLOID® particles were evident to a small extent. It is believed that coating was successfully achieved through employment of the gelatin.

For spray-dried SYLOID® XDP6035 particles (MetP_63, 63A, 64, and 64A), large SYLOID® particles appeared separate from the gelatin particles. The SYLOID® particles size of 35.1 μm was therefore deemed unsuitable for spray drying or coating testosterone compositions under the conditions tested.

Rod-like structures also appeared in SEM images of some compositions (MetP_59, MetP_64A, and MetP_88), which suggested the presence of bacteria, thus highlighting the importance of using sterile raw materials and sterile production conditions.

Synthesis of Core/Shell Particles with a Three-Fluid Nozzle

Experiments for loading SYLOID® particles with testosterone and simultaneously coating them with gelatin were carried out in a single step process by means of a three-fluid nozzle.

For production of core particles, 0.5 g of SYLOID® particles in 50 mL of ethanol was stirred at 500 rpm for at least an hour. For testosterone-loaded particles, 0.214 g of testosterone was dissolved in ethanol.

For production of the shell, F15 gelatin was dissolved in a 45/55 (v/v) solution of ethanol and water. 82.5 mL of water was first added and the gelatin solution and shaken in an incubating shaker at 37° C. until completely dissolved. Then 67.5 mL of ethanol with 0.375 g of testosterone were added and stirred.

The SYLOID® particle suspension (core) was transported via an external pump while the gelatin solution (shell) was transported via an internal pump to the three-fluid nozzle. 50 mL of "core" solution was employed for each 150 mL of "shell" solution; excess shell solution was synthesized so that about 45 mL remained after spraying. For MetP_72, the solutions were sprayed via the corresponding other pump.

The parameters of the Mini Spray Dryer during the experiments with the three-fluid nozzle were held constant with a temperature of 135° C., aspirator power 100%, dispersion gas 45 mm, and nozzle cleaner 0 (since it was not available on the three-fluid nozzle). The spray drying took place in a closed system of suction. The SYLOID® suspensions were stirred at 200 rpm during the spray drying. The variable parameters are shown in Table 23.

TABLE 23

Parameters and results of the spray-drying experiments by using the three-fluid nozzle.

| Batch | SYLOID ® | Theoretical testosterone loading core (%) | Theoretical testosterone loading shell (%) | Feed rate intern (%) | Feed rate extern (mL/min) | Yield (%) |
|---|---|---|---|---|---|---|
| MetP_65 | 244FP | — | — | 12 (4 mL/min) | 2 | 72.0 |
| MetP_66 | XDP6035 | — | — | 12 | 2 | 53.0 |
| MetP_72 | XDP6035 | — | — | 6 (2 mL/min) | 4 | 43.1 |
| MetP_76 | 244FP | 30 | — | 12 | 2 | 67.3 |
| MetP_77 | 244FP | 30 | 20 | 12 | 2 | 61.2 |

There were no complications with the experiments using the SYLOID® 244FP. However, the somewhat larger SYLOID® XDP6035 particles (MetP_66) occluded the tube of the external peristaltic pump. For this reason, the solutions were each sprayed via the other pump (MetP_72). Despite the resultant spraying procedure running smoothly, the yield lower than for other compositions.

Figure 27A:
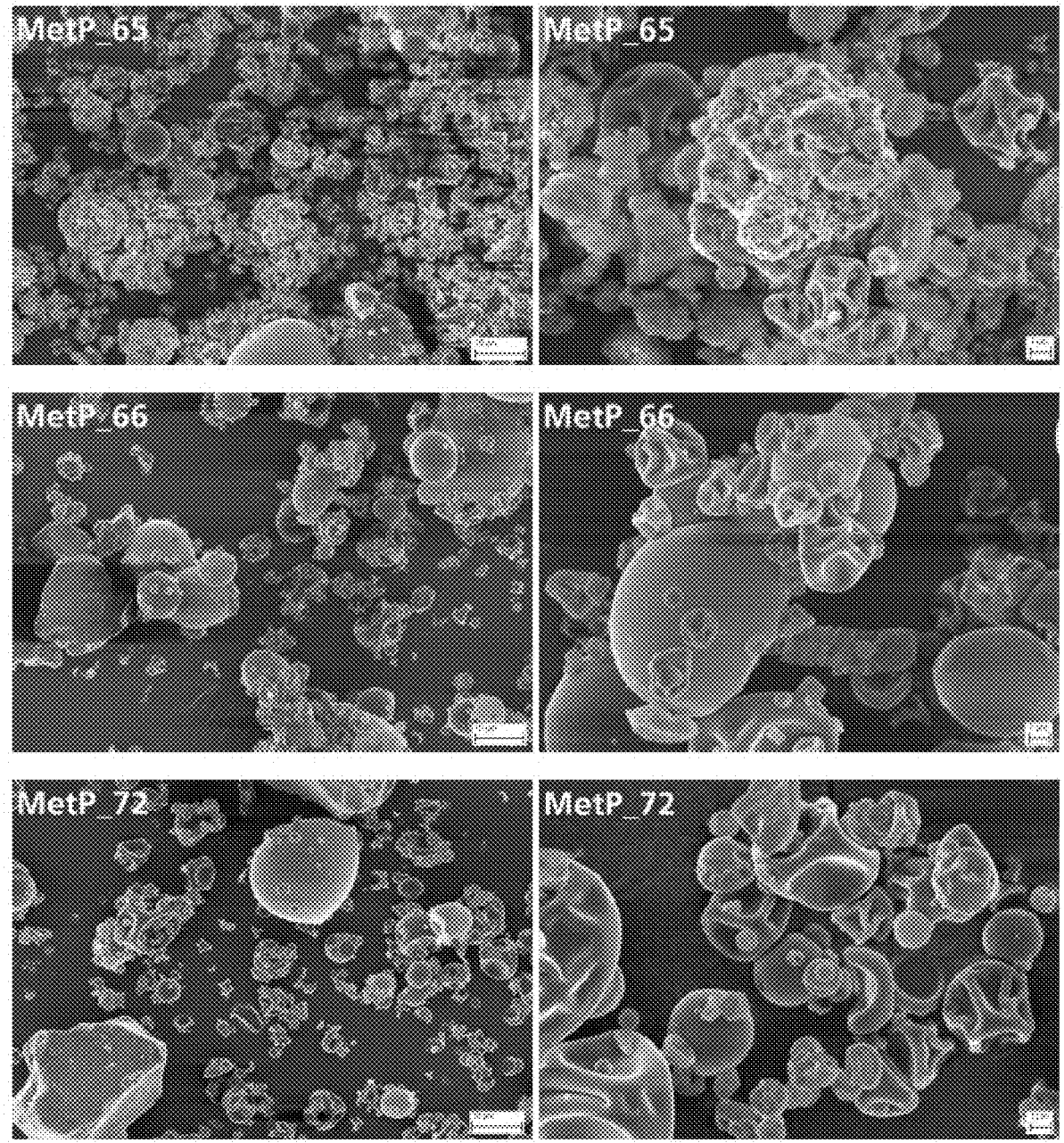
FIG. 27 (FIGS. 27A-B) shows scanning electron micrographs of mesoporous silica particles, some of which are loaded with testosterone, that were spray dried with a three-fluid nozzle.
Figure 27B:
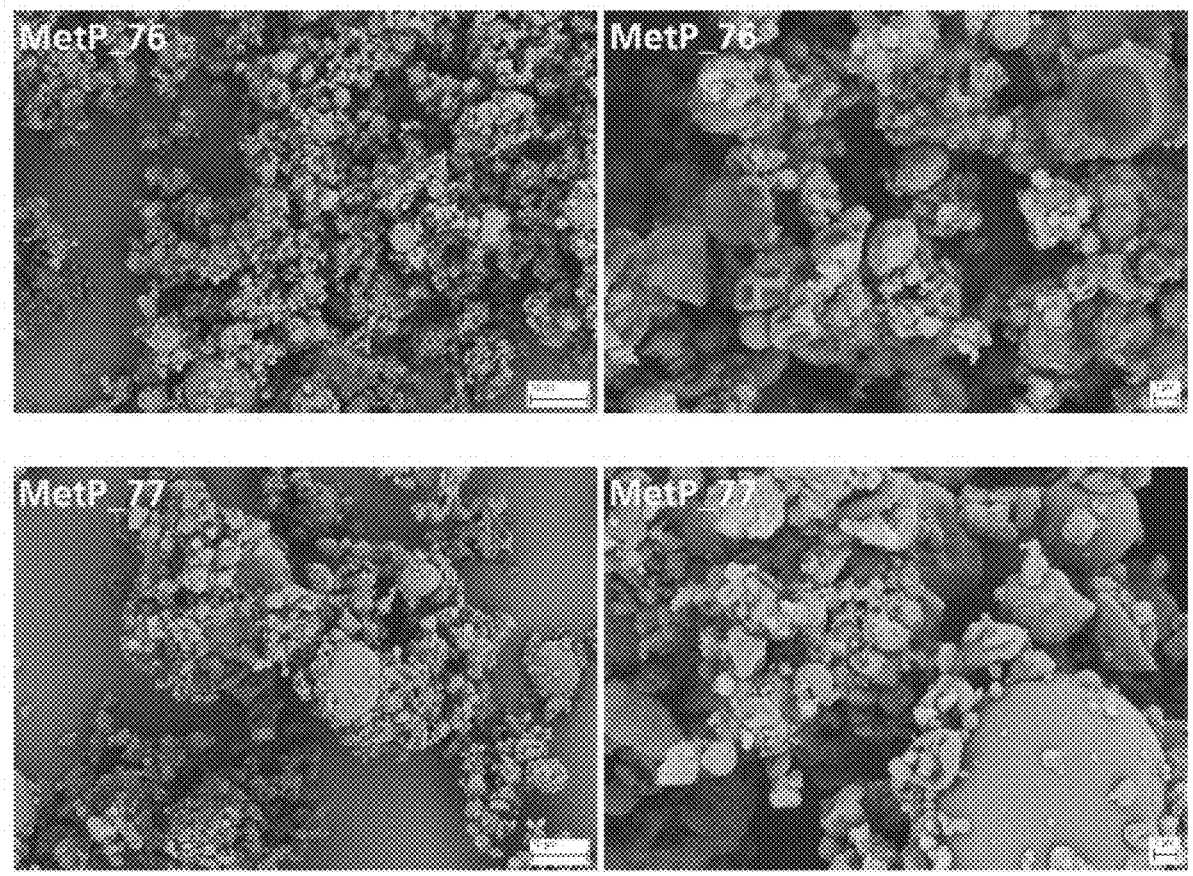

As shown in SEM images in FIGS. 27A-B, the MetP_66 and MetP_72 possessed larger fragments (SYLOID® XDP6035 particles) and smaller gelatin particles. The open-pore structure of the SYLOID® particles was still present, even for the smaller SYLOID® 244FP particles (see MetP_65, MetP_76, and MetP_77). The extent to which the particles were nevertheless coated by the gelatin was not assessed.

Determination of Particle Size by Laser Refraction

Particle sizes were measured for various compositions prepared in accordance with some of the preceding examples. The Scirocco dry measurement cell offers a means of surveying samples in the form of powder, but the necessary sample sizes are quite large and the measurement method is therefore unsuitable for our purposes. Thus, particle sizes were determined with the Mastersizer 2000 (Malvern). These compositions are shown in Table 24. Polylactide particles could not be characterized by means of the Mastersizer due to the dispersion behavior in ethanol. Samples were dispersed in ethanol and surveyed in the Hydro 2000 µP dispersion measurement cell (pump speed 2500 rpm, ultrasound 30%). Without being bound by theory, it is believed that the particles are in a swollen state caused by their dispersion in ethanol, thus impacting the observed particles sizes.

TABLE 24

Results of the particle size by laser diffraction (Hydro 2000 µP measuring cell).

| Batch | Material | d(0.1) (µm) | d(0.5) (µm) | d(0.9) (µm) |
|---|---|---|---|---|
| MetP_40 | Chitosan 95/200 | 0.194 | 5.143 | 15.437 |
|  | SYLOID ® 244FP | 0.106 | 0.831 | 4.177 |
| MetP_53 | Gelatin | 0.120 | 1.946 | 7.445 |

Determination of Particle Loading

The actual testosterone load of various spray-dried particles was determined. Since the loading material (silica) in testosterone-loaded SYLOID® particles cannot be removed by treatment with solvents, a release experiment was carried out over a longer period (>seven days). The calculation of the load percentage was carried out under the assumption that 100% of the testosterone was released over a period of >seven days.

About 10 mg of each of the loaded particles were weighed out in a small glass container with 20 mL of 45/55 (v/v) ethanol/water added using a volumetric pipette. This dispersion was subsequently stirred by means of a magnetic stirrer for a period (>seven days) at room temperature. Following the appropriate release period, samples were taken and centrifuged at 15,000 rpm by means of a tabletop centrifuge for 10 minutes to remove the SYLOID® particles from the solution. The samples were subsequently diluted so they were within the calibration interval.

The mass concentration of the standards and the samples were determined by means of UV/VIS spectroscopy (Synergy 2 multi-mode microplate reader from BIOTEK® Instruments). A quartz microtiter plate with 96 wells was used, in which 200 µL of standard or sample were pipetted into each well. The concentrations were determined by means of three assessments and a load level calculated under the assumption of 100% release. The load levels determined for the various testosterone-loaded particles are depicted in Table 25.

TABLE 25

Results of the testosterone-loading of particles.

| Batch | Material | Testosterone | Dried* | Theoretical loading (%) | Determined loading (%) |
|---|---|---|---|---|---|
| MetP_57 | SYLOID ® 244FP | first delivery | No | 29.9 | 25.3 |
| MetP_59 | MetP_57 in Gelatin F15 | first delivery | No | 22.9 | 18.2 |
| MetP_59 | MetP_57 in Gelatin F15 | first delivery | Yes | 22.9 | 20.4 |
| MetP_76 | SYLOID ® 244FP in Gelatin F15 | first delivery | Yes | 14.3 | 11.8 |
| MetP_77 | SYLOID ® 244FP in Gelatin F15 | first delivery | Yes | 26.7 | 24.6 |
| MetP_86 | SYLOID ® 244FP | first delivery | Yes | 30.0 | 28.0 |
| MetP_88 | MetP_86 in Gelatin F15 | first delivery | Yes | 22.9 | 22.6 |
| MetP_92 | SYLOID ® 244FP | second delivery | No | 30.0 | 27.0 |
| MetP_92 | SYLOID ® 244FP | second delivery | Yes | 30.0 | 23.9 |
| MetP_93 | SYLOID ® 244FP | second delivery | Yes | 29.9 | 26.5 |
| MetP_94 | SYLOID ® 244FP | second delivery | Yes | 40.0 | 34.2 |
| MetP_96 | Gelatin F15 | second delivery | No | 30.1 | 29.7 |
| MetP_102 | AEROSIL ® 200 | second delivery | Yes | 29.5 | 28.7 |

*Drying in a vacuum desiccator

Comparing the theoretical loading levels with the actual loading levels revealed a high recovery rate. The largest deviations from the theoretical value were in the cases of MetP_92 at 6.1% and Met_94 at 5.8%. For the rest of the samples, the absolute percentage differences were between 0.8% and 4.7%. The efficiency of the testosterone loading is thus quite high, lying between 79.5% and 98.7%.

Formulation of Nasal Gels

Nasal gels were prepared using castor oil, testosterone, LABRAFIL®, and AEROSIL® 200. For preparing the gels, castor oil and the corresponding quantities of testosterone, LABRAFIL®, and AEROSIL® 200 were added in sequence. The gels were produced by means of either a rotor/stator (up to 100 g) or in a ball mill (Precellys, 1-4 g). Experiments were also conducted with the Dispermat, which offers the means of preparing gels in the range of 30-40 g (data not shown). Various quantities of nasal gel were prepared through the various dispersion avenues.

Nasal gels were initially prepared according to the nasal gel formula in Table 26.

TABLE 26

Recipe of initial nasal gel composition.

| Amount castor oil (%) | Amount testosterone (%) | Amount LABRAFIL ® (%) | Amount AEROSIL ® 200 (%) |
|---|---|---|---|
| 89.70 | 2.30 | 4.00 | 4.00 |

The content of various prepared nasal gel compositions is shown in Table 27. Larger quantities were prepared by homogenizing with a rotor/stator mixing apparatus (nasal gel 03). Each sample was mixed at 13,000 rpm for 2×2 minutes following the addition of testosterone and LABRAFIL®. Following the addition of AEROSIL® 200, premixing was carried out first using a glass rod and afterwards by homogenizing at 13,000 rpm for a total of 20 minutes.

TABLE 27

Amounts of components in compositions prepared without SYLOID ® particles

| Nasal gel | Amount castor oil (g) | Amount testosterone (g) | Amount LABRAFIL ® (g) | Amount AEROSIL ® 200 (g) |
|---|---|---|---|---|
| 03 | 89.70 | 2.30 | 4.00 | 4.00 |
| 05 (A) | 2.240 | 0.060 | 0.100 | 0.100 |
| 05 (B) | 2.240 | 0.060 | 0.100 | 0.100 |
| 06 (A) | 3.360 | 0.090 | 0.150 | 0.150 |
| 06 (B) | 3.360 | 0.090 | 0.150 | 0.150 |

Smaller lots were prepared with a ball mill (Precellys) beginning with nasal gel lot 05, so that small quantities of loaded particles could be introduced. A quick and gentle mixing and dissolving process was used for preparing the gel: 7 mL plastic containers were used in this mixing process, which contained two zirconium oxide beads (diameter of 6.8 mm); a vortex mixer was used for pre-mixing the components (castor oil, testosterone, and LABRAFIL®) for 10 minutes; the AEROSIL® 200 was then added and the homogenization carried out in the ball mill at 4000 rpm within 3×30 minute periods with 2×30 s pauses. The percentage proportion of the substances in the nasal gel formula is shown in Table 28.

TABLE 28

Percentage of components in compositions prepared without SYLOID ® particles

| Component | Amount (%) |
|---|---|
| Castor oil | 90.00 |
| Testosterone | 2.00 |
| LABRAFIL ® | 4.00 |
| AEROSIL ® 200 | 4.00 |

Nasal gel lot 07 (A) in Table 29 was prepared according to the nasal gel formula in Table 28. SYLOID® particles were used to prepare nasal gel lots 07 (B) and 07 (C).

TABLE 29

Amounts of components in compositions prepared with SYLOID ® particles

| Nasal gel | Amount castor oil (g) | Amount testosterone (g) | Amount LABRAFIL ® (g) | Amount AEROSIL ® 200 (g) | Amount SYLOID ® 244FP (g) |
|---|---|---|---|---|---|
| 07 (A) | 3.375 | 0.075 | 0.150 | 0.150 | — |
| 07 (B) | 3.375 | 0.075 | 0.150 | — | 0.150 |
| 07 (C) | 3.375 | 0.075 | 0.150 | 0.150 | 0.150 |

Figure 28:
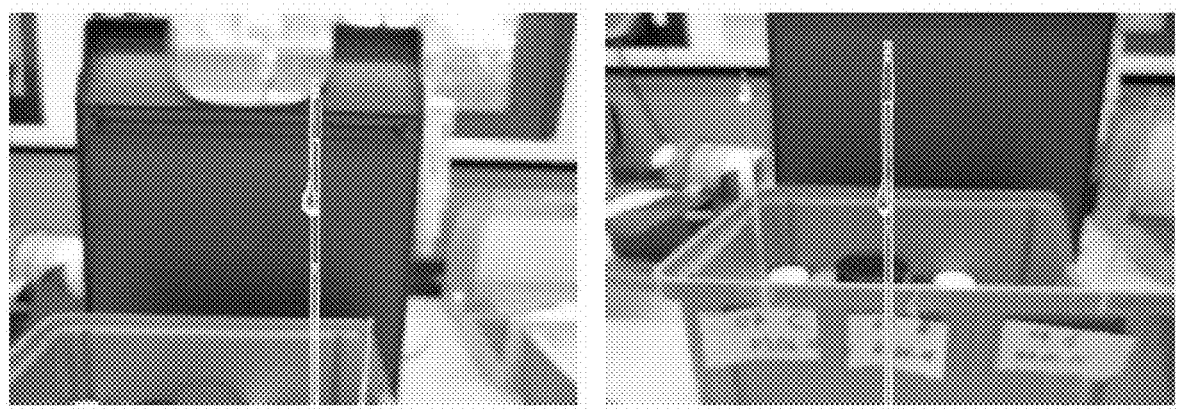
FIG. 28 sets forth photographs demonstrating a rod test conducted to assess flow behavior of various compositions.

The gelling behavior of SYLOID® 244FP was compared with that of AEROSIL® 200, based on compositions in Table 29. The flow behavior of the lots was determined by means of a rod test, in order to determine if AEROSIL® 200 can be replaced by SYLOID® 244FP. The rod test (see FIG. 28) showed that SYLOID® 244FP in quantities present in composition 07 (B) (on the right side of FIG. 28) was insufficient to cause comparable gelling behavior to 4% AEROSIL® 200 (on the left side of FIG. 28). Additional experiments showed that gelling behavior similar to 4% AEROSIL® 200 occurred at a proportion of 8-10% with SYLOID® 244FP.

Formulation of Nasal Gel with Testosterone-Loaded Particles

Nasal gels with testosterone-loaded porous particles (adsorbate) were formulated with 11 mg of testosterone adsorbate (6.75 mg in solution and 4.25 mg from adsorbate). The formula is set forth in Table 30, where the total quantity was held constant.

TABLE 30

Recipe of nasal gel (constant total volume).

| Component | Amount (%) |
|---|---|
| Castor oil | Varies (ad) |
| Testosterone (dissolved) | 4.50 |
| LARRAFIL ® | 4.00 |
| AEROSIL ® | 4.00 |
| Adsorbate | Varies |
| Testosterone (adsorbate) | 2.8 |

Nasal composition preparation must balance competing concerns: maintaining a constant total quantity versus maximizing active agent solubility. If the total quantity is held constant, incorporating the SYLOID® particles would reduce the quantity of castor oil added, which could impact solubility of the testosterone in castor oil. On the other hand, if the quantity of castor oil remains constant (and solubility of testosterone is not impacted), the addition of the SYLOID® would make it so the proportions would not remain constant, thereby altering the composition recipe.

With this in mind, nasal gels having constant quantities of castor oil were prepared under this feasibility study as a first step. These compositions are shown in Table 31 and were synthesized using a ball mill (Precellys).

TABLE 31

Nasal gel compositions with constant castor oil quantity.

| Gel | Amount castor oil (g) | Amount testosterone (g) | Amount LABRAFIL ® (g) | Amount AEROSIL ® 200 (g) | Loaded particles (Adsorbate) | | |
|---|---|---|---|---|---|---|---|
| | | | | | Charge | Amount (Matrix) (g) | Amount Theor. Test. (g) |
| 10.4 | 0.867 | 0.039 | 0.0347 | 0.0347 | MetP_88 | 0.0847 | 0.0246 |
| 10.5 | 0.867 | 0.039 | 0.0347 | 0.0347 | MetP_86 | 0.0578 | 0.0246 |

TABLE 31-continued

Nasal gel compositions with constant castor oil quantity.

| Gel | Amount castor oil (g) | Amount testosterone (g) | Amount LABRAFIL ® (g) | Amount AEROSIL ® 200 (g) | Loaded particles (Adsorbate) | | |
|---|---|---|---|---|---|---|---|
| | | | | | Charge | Amount (Matrix) (g) | Amount Theor. Test. (g) |
| 10.6 | 0.867 | 0.039 | 0.0347 | 0.0347 | MetP__87 | 0.0976 | 0.0246 |
| 10.7 | 0.867 | 0.039 | 0.0347 | 0.0347 | MetP__85 | 0.0578 | 0.0246 |

In the compositions in Table 31, all components of the nasal gels were held constant with respect to their masses except the matrix of the loaded particles. Composition 10.4 used SYLOID® 244FP particles theoretically loaded with 30% testosterone and subsequently coated with gelatin (MetP_88). Composition 10.5 used SYLOID® 244FP particles theoretically loaded with 30% testosterone (MetP_86). Loaded F15 gelatin particles (MetP_87, theoretical loading level 20%) were used in composition 10.6, while PLA (MetP_85, theoretical loading level 30%) was used in composition 10.7.

In separate experiments designed to maintain a constant total quantity of nasal gels for synthesis, gels were prepared based on the formula shown in Table 30, where compositions were homogenized with a ball mill (Precellys).

Nasal gel 11, with a formula shown in Table 32, was prepared as a reference, i.e. without addition of particles loaded with active ingredients (thus without adsorbate).

TABLE 32

Composition for reference nasal gel.

| Nasal gel | Amount castor oil (g) | Amount testosterone (g) | Amount LABRAFIL ® (g) | Amount AEROSIL ® 200 (g) |
|---|---|---|---|---|
| 11 | 2.625 | 0.135 | 0.120 | 0.120 |

Release experiments were also carried out with the nasal gel approaches listed in Table 33.

TABLE 33

Nasal gel compositions.

| Gel | Amount castor oil (g) | Amount testosterone (g) | Amount LABRAFIL ® (g) | Amount AEROSIL ® 200 (g) | Loaded particles (Adsorbate) | | |
|---|---|---|---|---|---|---|---|
| | | | | | Charge | Amount Matrix (g) | Amount Theor. Test. (g) |
| 12.1 | 0.78043 | 0.04500 | 0.04000 | 0.04000 | MetP__85 | 0.06623 | 0.02834 |
| 12.2 | 0.78059 | 0.04500 | 0.04000 | 0.04000 | MetP__86 | 0.06609 | 0.02832 |
| 12.3 | 0.73397 | 0.04500 | 0.04000 | 0.04000 | MetP__87 | 0.11282 | 0.02821 |
| 12.4 | 0.75133 | 0.04500 | 0.04000 | 0.04000 | MetP__88 | 0.09534 | 0.02833 |

Figure 29:
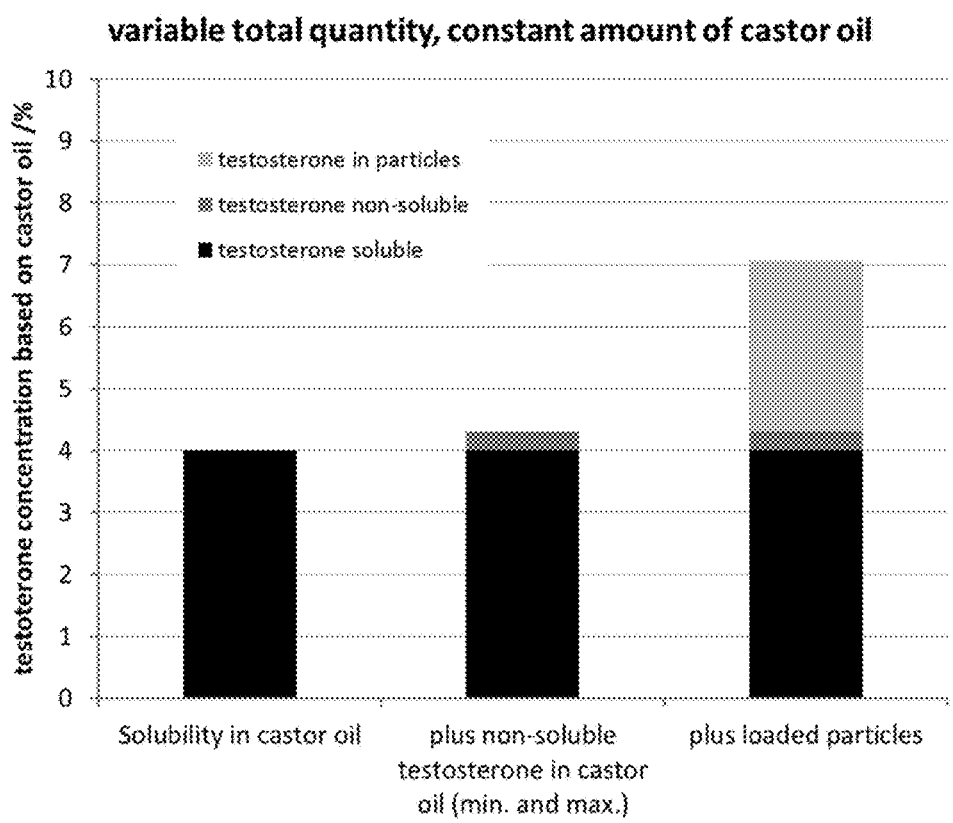
FIG. 29 shows solubility data associated with various testosterone compositions as described herein where the quantity of castor oil in the composition is held constant.

To illustrate the challenges in preparing the nasal gel, the composition of the two nasal gel formulation variants is shown in FIG. 29. Based on solubility results, testosterone displays a solubility of about 4% in castor oil (leftmost bar in FIG. 29). In the case of the variant illustrated in FIG. 29 with a constant quantity of castor oil, an insoluble portion of 0.3% testosterone (top portion of middle bar) would be present. The top portion of the rightmost bar corresponds to the quantity of testosterone contributed by the adsorbate (testosterone in particles).

Figure 30:
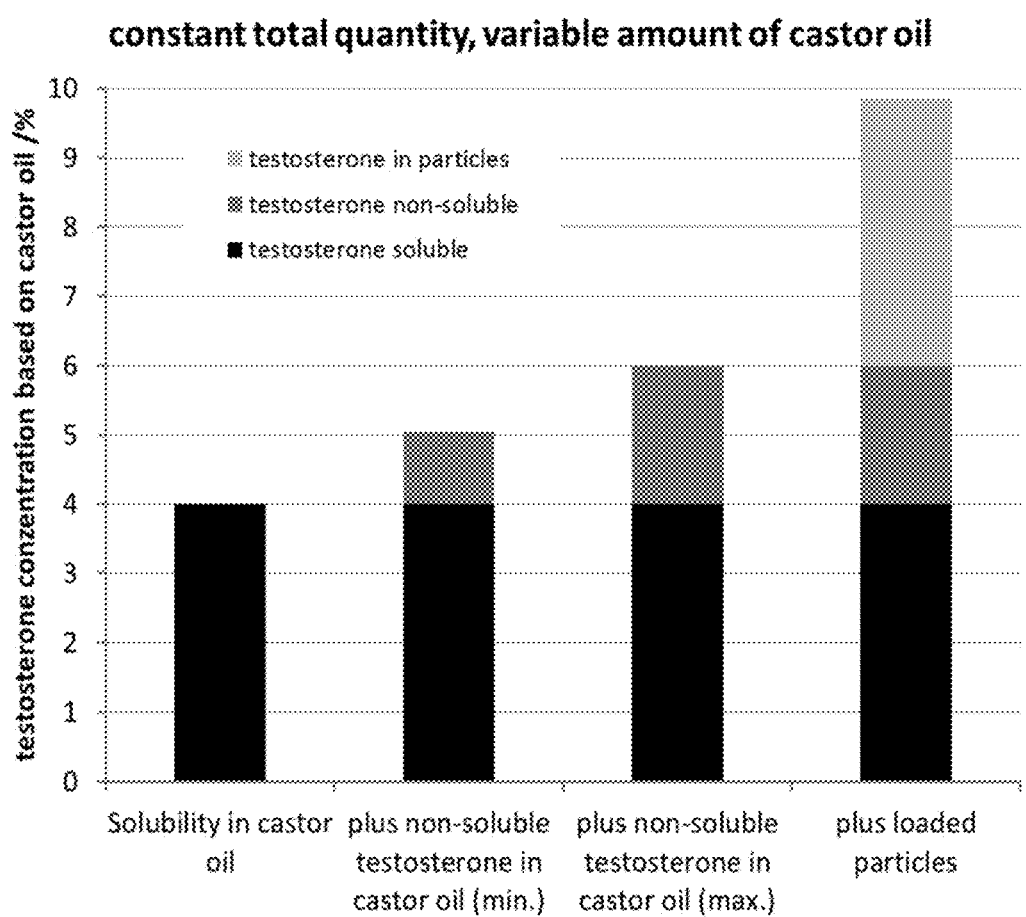
FIG. 30 shows solubility data associated with various testosterone compositions as described herein where the quantity of castor oil in the composition is varied.

If the total quantity is constant, however (see FIG. 30), the castor oil quantity must be reduced by an amount corresponding to the added quantity of adsorbate. That means the proportion of undissolved testosterone increases as a function of the particle loading in a range of 1% to 2% (top portion of middle two bars; middle portion of rightmost bar). FIGS. 29 and 30 together demonstrate that difficulty in preparing a formula that avoids undissolved testosterone.

Example 16—Differential Scanning Calorimetry Measurements

The melting behavior of the samples was investigated by dynamic differential scanning calorimetry to determine the crystallinity of the testosterone. Two heating curves (heating rate: 5 K/min/cooling rate: 20 K/min) were recorded for each on the DSC 200 F3 MAIA® dynamic differential calorimeter (Netzsch) over a temperature range of 0° C. to 200° C. in an inert atmosphere (nitrogen, 40 mL/min).

Without being bound by theory, it is believed that the thermal prehistory is influenced by the processing procedure—spray drying in this case—and can be discerned from the differences between the first and second heating curves. The second heating curve thereby provides the initial material specific data. In this project, however, the first heating demonstrates whether testosterone is present in crystalline or amorphous form in the individual particle compositions.

Figure 31:
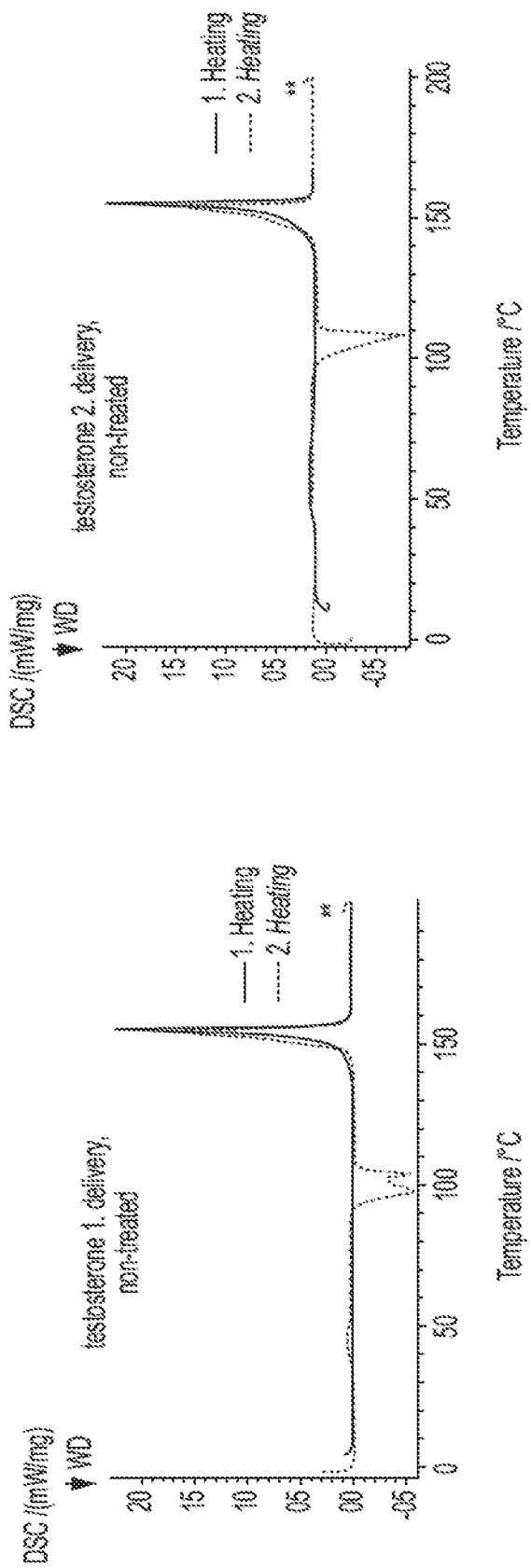
FIG. 31 shows differential scanning calorimetry measurements obtained with two different batches of testosterone.

The untreated testosterone batches from different deliveries were compared. These DSC curves are shown in FIG. 31. At the first heating a melting peak for testosterone at 155.3° C. (first delivery) and at 155.2° C. (second delivery) is seen. The melting peak at the second heating was slightly shifted to 154.4° C. (first delivery) and 154.2° C. (second delivery). In addition, a glass transition at approximately 40° C. and a recrystallization peak for testosterone (first delivery) at 97.9° C. (maximum) and second delivery at 108.4° C. (maximum) were detected.

Figure 32:
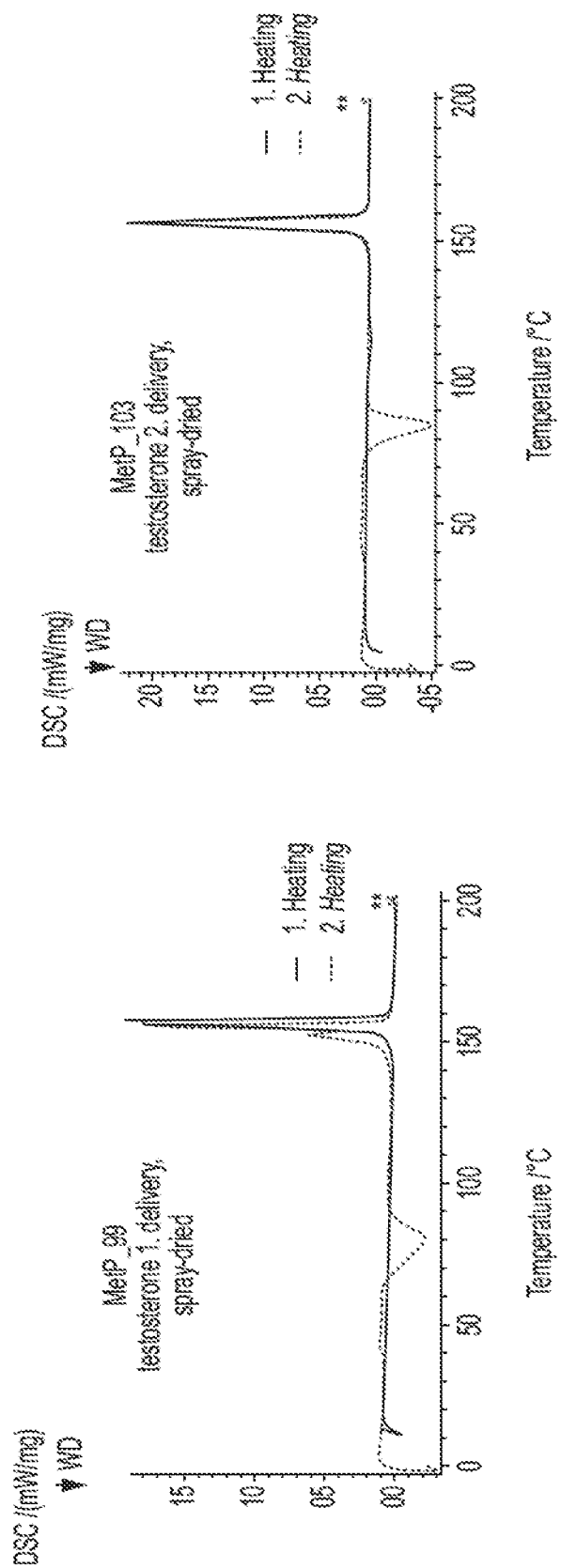
FIG. 32 shows differential scanning calorimetry measurements obtained on two different batches of testosterone spray dried in ethanol.

In order to investigate the influence of spray drying on the testosterone, both testosterone batches were sprayed in pure ethanol and likewise surveyed. These results are shown in FIG. 32. The recrystallization peak (at 80.4° C. and 84.5° C.) of the second heating is considerably shifted compared to the untreated testosterone samples.

Figure 33:
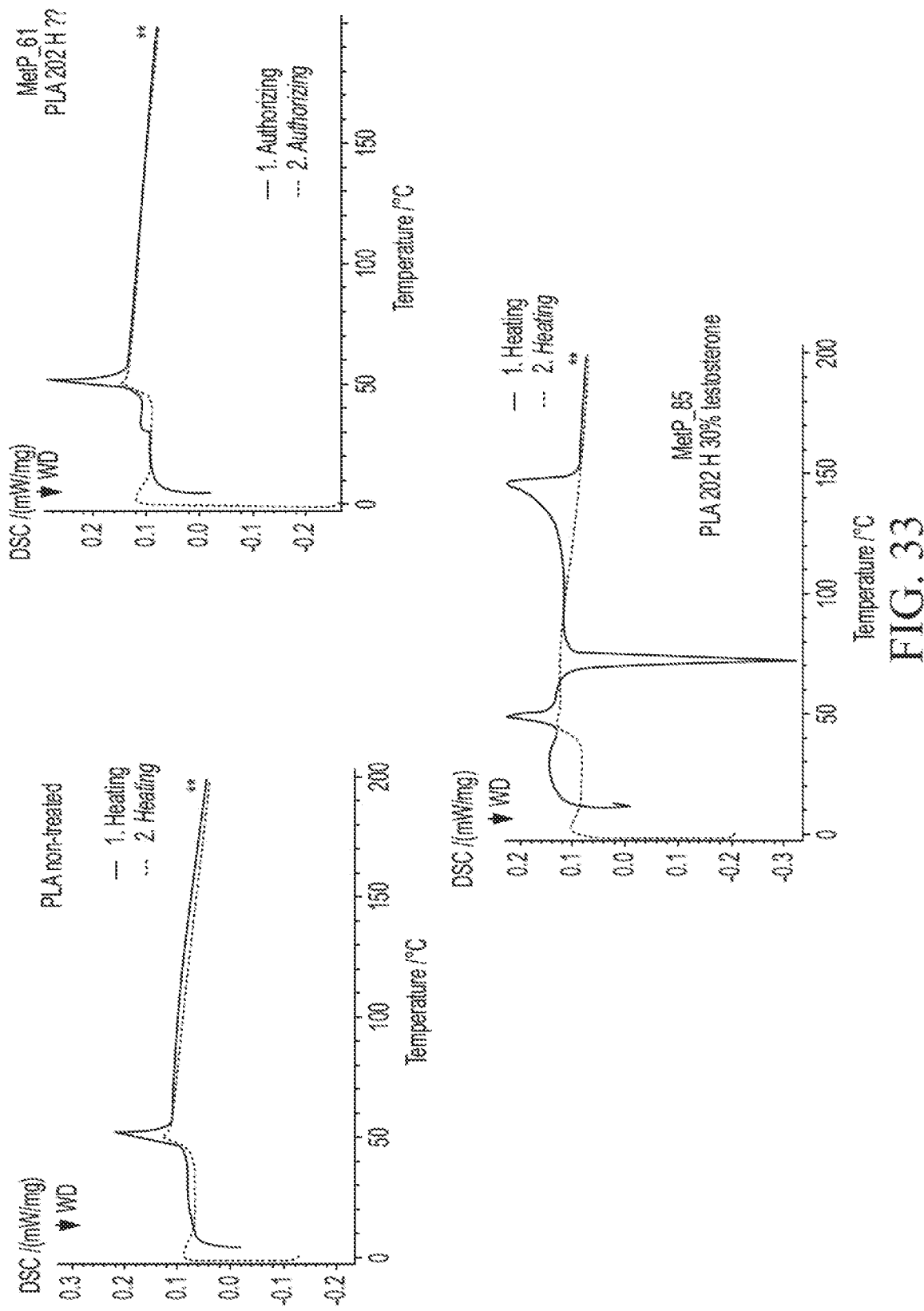
FIG. 33 shows differential scanning calorimetry measurements obtained with various compositions with polylactic acid.

Polylactide (PLA) is an amorphous polymer and therefore there is no melting peak present for this polymer. Only a glass transition in the neighborhood of 50° C. was detected, as shown in FIG. 33. The DSC curves of both PLA samples (PLA unsprayed and MetP_61) differ only slightly in the first heating; however, no difference was established in the curves for the second heating. For the testosterone-loaded particles, a somewhat different procession in the curves is evident for the first heating. A broad melting peak and a recrystallization peak are detectable; however, these are shifted somewhat in comparison to pure testosterone (melting peak maximum at 146° C. and recrystallization peak maximum at 73.5° C.). The presence of the melting peak for testosterone shows that this active agent is still present in crystalline form after spray drying.

Figure 34:
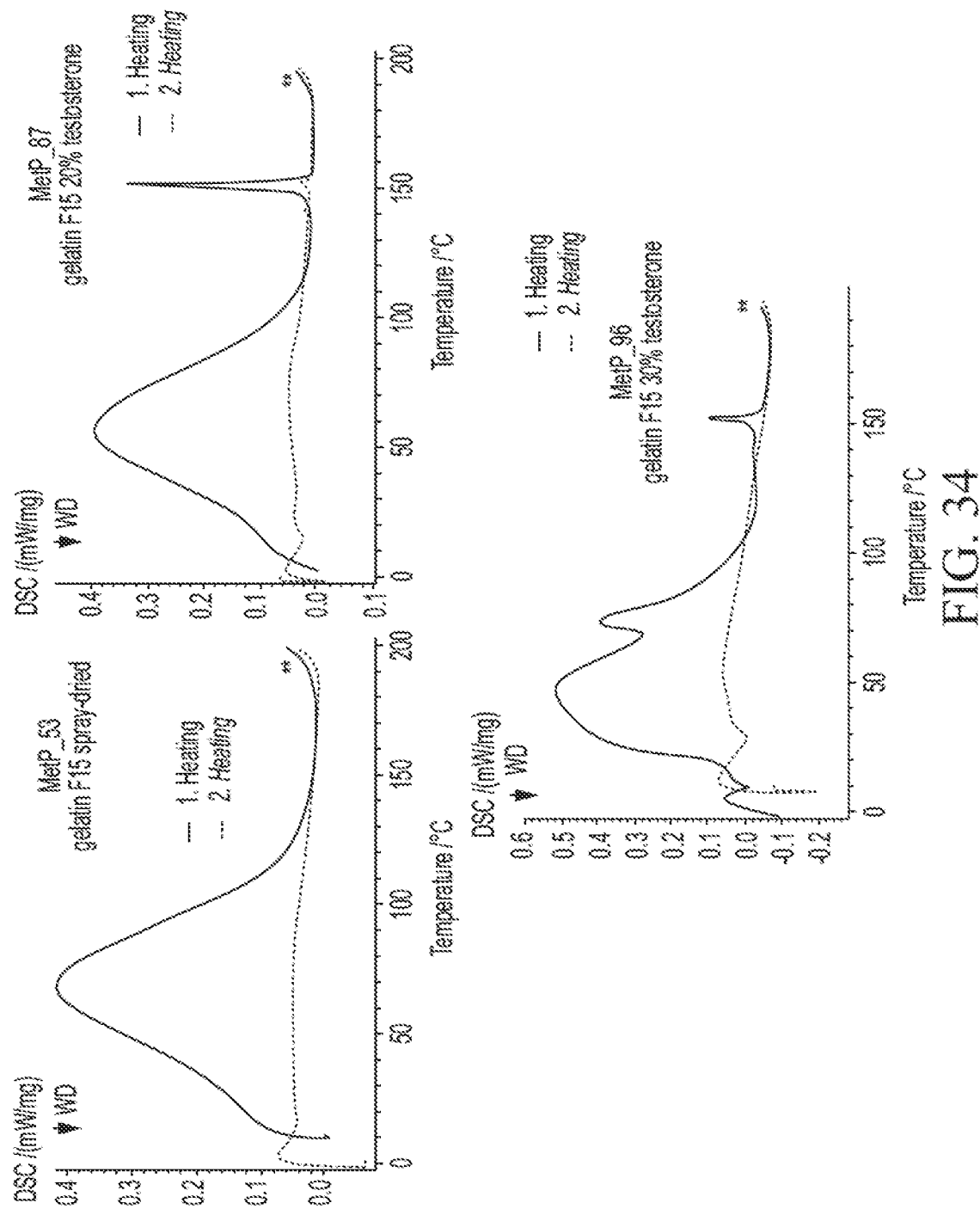
FIG. 34 shows differential scanning calorimetry measurements obtained with various compositions with gelatin.

The DSC curves of spray-dried unloaded (MetP_53) and testosterone-loaded F15 gelatin (theoretical loading level for MetP_87:20%/theoretical loading level for MetP_96:30%) are shown in FIG. 34. Gelatin displays a broad endothermic peak that results from the evaporation of adsorbed water. A base line rise is evident at 200° C. that very probably represents the beginning helix-coil transition.

A clear testosterone melting point during the first heating is evident for the loaded gelatin particle batch MetP_87 that is sharply reduced in the second heating. A smaller additional peak emerged at <150° C. For the approach with a higher theoretical testosterone loading of 30% (MetP_96), a melting peak is detected that is smaller in comparison to MetP_87.

Figure 35:
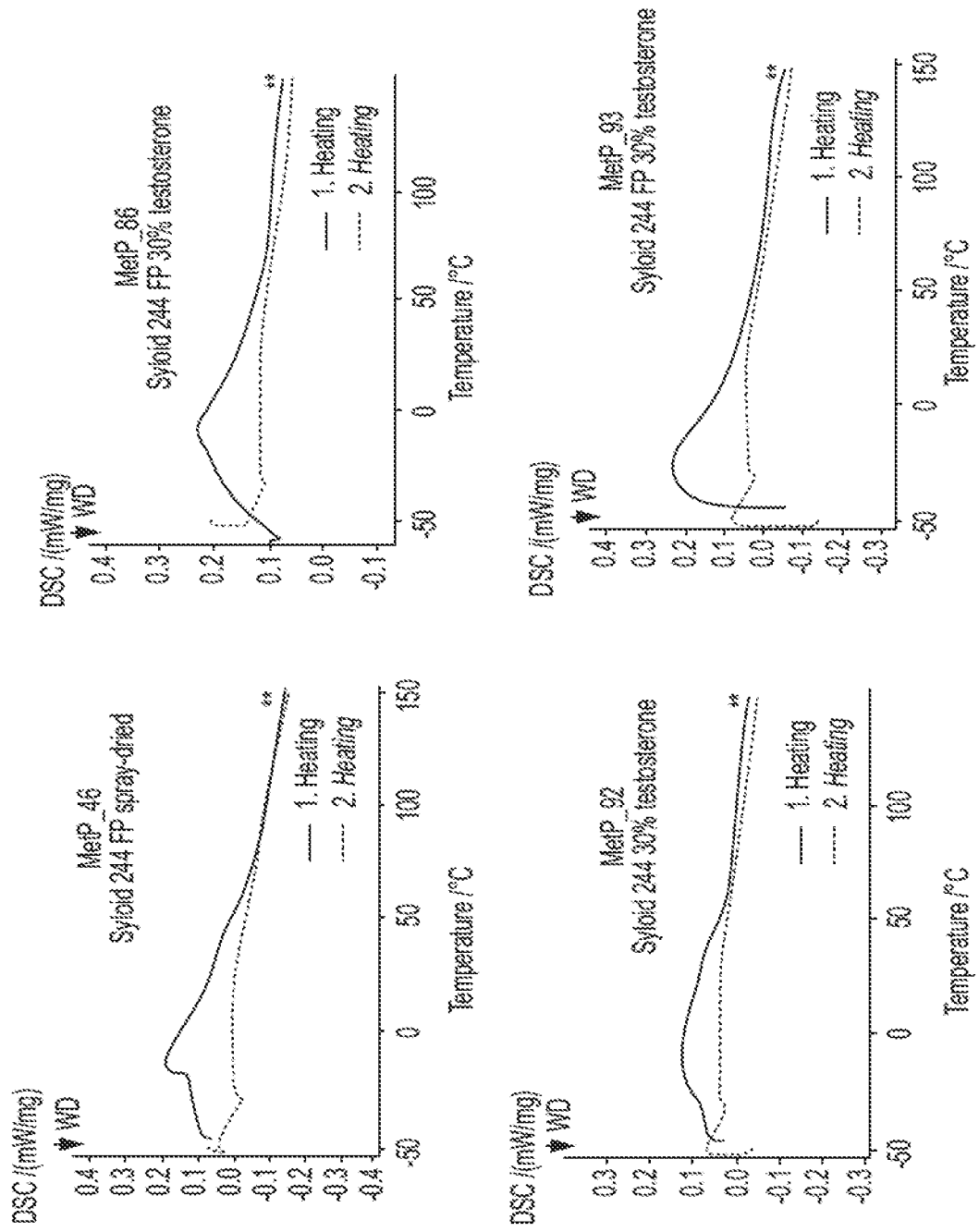
FIG. 35 shows differential scanning calorimetry measurements obtained with compositions having SYLOID® 244FP particles.

For the testosterone-loaded mesoporous silica particles (SYLOID® 244FP), no testosterone melting peak in the neighborhood of 150° C. could be detected either for the first or second heating, which is evident from the DSC curves in FIG. 35. All curves here displayed a broad endothermic peak as well that likely emerges analogous to gelatin on account of evaporation of adsorbed water.

It was assumed that testosterone was not present in crystalline form, but instead amorphous (this could be substantiated through further investigations, e.g., synthesis of testosterone and SYLOID® mixtures, and employment of higher testosterone proportions analogous to the procedure with progesterone).

Figure 36:
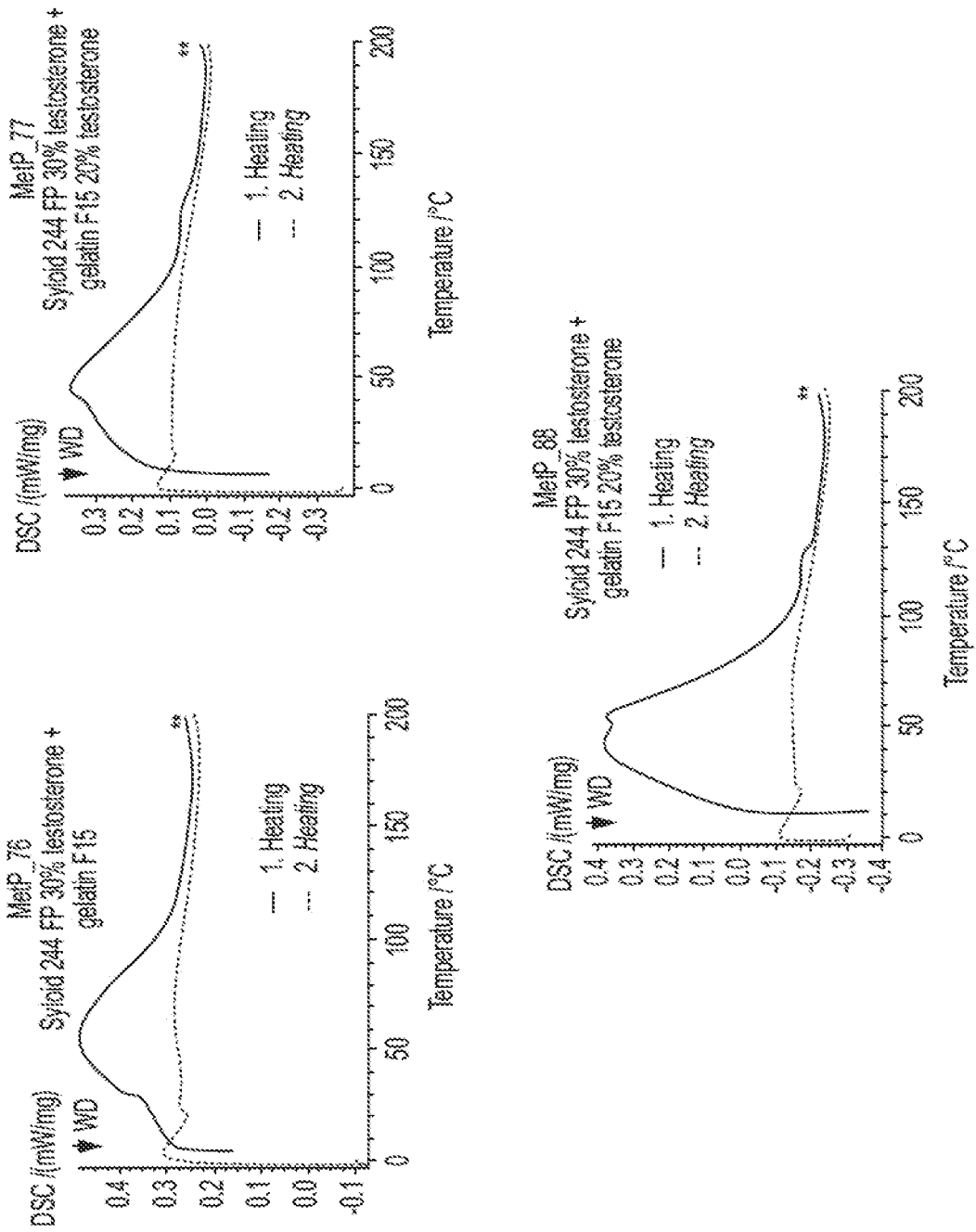
FIG. 36 shows differential scanning calorimetry measurements obtained with compositions having SYLOID® 244FP particles provided with a gelatin shell.

The DSC curves of the silica/gelatin core/shell particles are shown in FIG. 36. The intensity of the evaporation peak clearly increased in comparison to the pure mesoporous silica particles due to the presence of the gelatin. MetP_76 and MetP_77 were synthesized by means of a three-component jet, i.e. in a single-step process. If the curves are now compared, that of the testosterone-loaded SYLOID® particles with unloaded gelatin as coating material (MetP_76) synthesized by means of a three-component jet, with the pure testosterone-loaded SYLOID® particles (MetP_86, 92, and 93, FIG. 42), they differ by the more strongly defined evaporation peak. No melt peak was detected. By implication, this means that testosterone is likely in amorphous form. In the presence of a loaded gelatin matrix (Met_77), the DSC curve displays a clear shoulder in the region of 120° C. to 125° C. This shoulder can also be detected in Met_88. MetP_88 exhibited a similar composition to MetP_77, but was synthesized in two steps by means of a two-component jet. Moreover, it appears here as though two further effects may be superposed. As a result, an additional suggested peak was discerned between 53.7° C.

Figure 37:
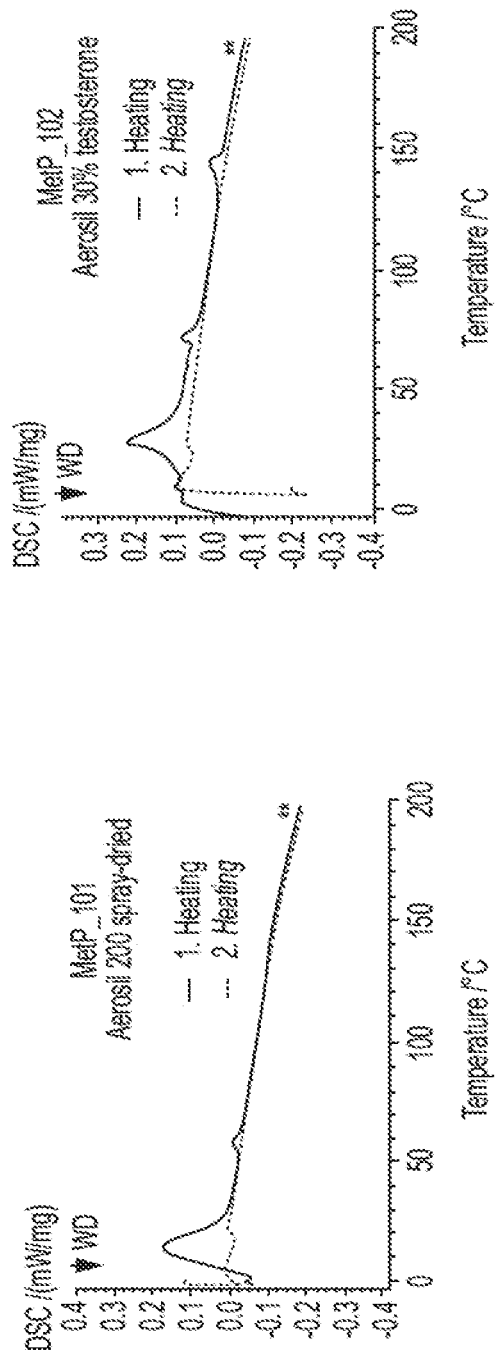
FIG. 37 shows differential scanning calorimetry measurements obtained with compositions having AEROSIL® 200 particles.

Non-porous silica particles (AEROSIL® 200) were spray-dried as references both as pure particles and in the presence of testosterone (theoretical loading level of 30%). The DSC curves of these samples are shown in FIG. 37. A small, somewhat broader melting peak just below 150° C. for the loaded particles is evident here. This is also understandable, since the primary particles do not exhibit a porous structure.

Figure 38:
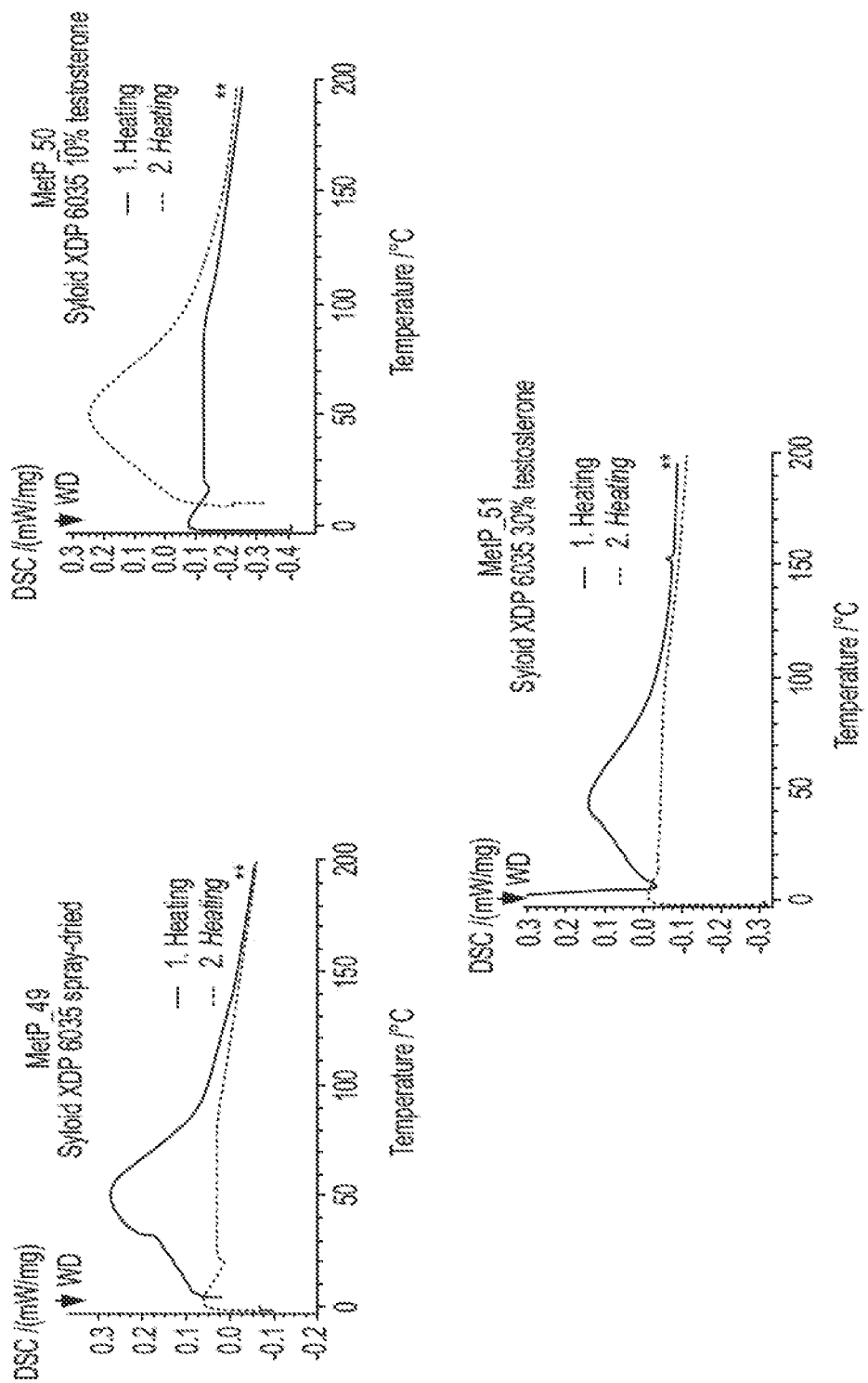
FIG. 38 shows differential scanning calorimetry measurements obtained with compositions having SYLOID® XDP6035 particles.

No melting peak in the neighborhood of 150° C. was discerned for the testosterone-loaded SYLOID® XDP6035 particles, as shown in FIG. 38, at a theoretical loading level of 10% (MetP_50). This becomes detectable beginning at a theoretical loading level of 30% (MetP_51).

Example 17—Summary of Testosterone Experiments

Various methods for loading testosterone were evaluated. The loading of testosterone in polymeric matrices by means of spray drying is feasible. Specifically, loading levels of approx. 30% and yields of approx. 50% were achieved by means of RESOMER® 202H particles. Likewise, loading levels of approx. 30% and yields of approx. 70% were achieved with chitosan 95/500 as an encapsulating material. F15 gelatin was also loaded with approx. 20% testosterone and achieved a yield of 30%.

Mesoporous silica particles were also able to be loaded by means of spray drying, e.g., with SYLOID® 244FP particles. Loading levels of approx. 40% and yields of approx. 70% were achieved. The SYLOID® 244FP particles can likewise be loaded by means of oil; however, the loading level was limited to 9.4% on account of the relatively poor solubility of testosterone in linalool.

Coating of the particles was carried out with a two-fluid nozzle as well as with a three-fluid nozzle. In this procedure, SYLOID® 244FP particles were employed as the core material and F15 gelatin as the coating material, achieving a loading level of about 23%. A yield of 90% was achieved by means of a two-fluid nozzle, while a yield of 60% was achieved by means of a three-fluid nozzle.

The DSC measurements established that the testosterone in the polymeric matrices was still present at least partially in crystalline form. No crystallite melting point at 150° C. could be discerned for the testosterone-loaded SYLOID® 244FP particles.

Example 18—Scaled-Up Production of Testosterone Compositions

Scaled-up batches of testosterone compositions were prepared using SILSOL™ 6035. In particular, 21 g of testosterone were dissolved in 118 g ethanol. The testosterone solution was added at 50-55° C. in a stepwise fashion via a pump (Master Flex) to a stirred SILSOL™ 6035 solution, to achieve a 25-30% testosterone loading. The resultant mixture was substantially free of lumps. The resultant mixture was dried under vacuum in a drying chamber at a pressure of about 8 mbar and a temperature that was escalated from about 50° C. to about 80° C. by the end of drying. For some batches, 3% polyvinylpyrrolidone (PVP) was added to the composition.

Compositions were further scaled up using the protocol discussed above. In particular, compositions with a 800 g batch size were produced, as shown in Table 34.

TABLE 34

Compositions with testosterone + SILSOL ™ 6035

| Batch | Batch Size | Active Agent Weight | Theoretical Loading | Yield |
|---|---|---|---|---|
| Batch 1 | 800 g | 240.1 g | 30% | 88% |
| Batch 2 | 800 g | 216.3 g | 27% (+3% PVP) | 88% |

Scaled-up batches produced with Silica XDP 3050 or 3150 as a porous excipients (instead of SILSOL™ 6035) yielded similar results.

Example 19—Stability of Scaled-Up Batches of Testosterone Compositions

Scaled-up batches of testosterone compositions were prepared using SILSOL™6035 in accordance with Example 18. Compositions were stored for 1 month at either 25° C./60% relative humidity or 30° C./65% relative humidity. Stability of the compositions following 1 month of storage were tested via differential scanning calorimetry. In all cases, degradation-related impurities in the compositions remained substantially unchanged after 1 month of storage. Moreover, the crystalline testosterone ratio (e.g., the percentage of testosterone that is in the crystalline state) in both formulations could be assumed to be below 0.5% by release, even after 1 month of storage. Moreover, the composition contained substantially no crystalline polymorphs of testosterone.

What is claimed is:

1. A nasal pharmaceutical composition in the form of a gel adapted for nasal administration, comprising a loaded porous excipient dispersed in a pharmaceutically acceptable vehicle, wherein:
   the loaded porous excipient comprises mesoporous silica particles wherein active agent in an amorphous state is loaded onto surfaces of the mesoporous silica particles located inside pores of the mesoporous silica particles, wherein the composition comprises from about 0.5% to about 50% w/w of the mesoporous silica based on the weight of the composition, and
   the vehicle comprises an oil or mixture of oils in an amount from about 50% to about 90% w/w of the composition,
   the composition comprises a therapeutically effective amount of the active agent of from 10% w/w to 50% w/w based on the weight of the composition, in a volume suitable for nasal application, and
   the composition has a viscosity of from about 2000 to about 6000 mPa·sec.

2. The composition of claim 1, wherein silica particles have pores with a longest diameter in any dimension selected from about 2 nm to about 50 nm.

3. The composition of claim 1, wherein the loaded porous excipient is coated with a polymer that forms a shell around the porous excipient, wherein the polymer is selected from a linear polymer, a cellulose-containing polymer, a copolymer, a cross-linked polymer, a collagen-containing polymer, and combinations of any two or more thereof.

4. The composition of claim 1, wherein pores in the loaded porous excipient are capped with a coating.

5. The composition of claim 1, wherein the active agent is selected from aripiprazol, quetiapin, paliperidon, duloxetine, dopamine, testosterone, glatirameracetat, interferon beta-1a, interferon beta-1b, fingolimod, natalizumab, dimethylfumarat, pregnenolone, memantine, rivastigmin, donepezil, desvenlafaxine, progesterone, eszopiclone, eszopiclone, atomoxetin, guanfacine, methylphenidate, lisdexamfetamine, recombinant tissue plasminogen activator (rt-PA), methotrexate, raltitrexed, 5-fluorouracil, telomerase inhibitor, monoclonal antibodies, midazolam, lacosamide, levetiracetam, lamotrigine, valproic acid, oxycodone, pregabalin, buprenorphine, hydrocodone, fentanyl, safinamide, ropinirole, pramipexole, L-DOPA, selegiline, cabergoline, istradefylline, and combinations of two or more thereof.

6. The composition of claim 1, wherein the composition is a vaccine and the active agent comprises an immunogen.

7. The composition of claim 1, wherein the composition comprises from 10% to about 40% (w/w) active agent based on the weight of the composition.

8. The composition of claim 1, wherein the vehicle comprises castor oil.

9. The composition of claim 1, further comprising a surfactant.

10. The composition of claim 9, wherein the surfactant comprises an oleoyl macrogolglyceride.

11. The composition of claim 1, wherein the composition comprises from about 6% to about 11% w/w of the mesoporous silica based on the weight of the composition.

12. A method of making a nasal pharmaceutical composition according to claim 1, wherein the method comprises loading the active agent onto the porous excipient, wherein the active agent is loaded via oil absorption onto a surface of the porous excipient located inside pores of the porous excipient.

13. The method of claim 12, further comprising spray drying together the active agent and the porous excipient after the active agent is loaded onto the porous excipient.

14. A method for vaccinating a subject against a condition comprising nasally administering the composition of claim 1 to a subject in need thereof, wherein:
   (a) the condition is influenza, and the active agent is live attenuated influenza virus, inactivated virus, or viral antigens;
   (b) The condition is hepatitis B, and the active agent is Hepatitis B virus (HBV), surface hepatitis B antigens (HBsAg), and/or core hepatitis B antigens (HBcAg); or
   (c) The condition is meningitis, and the active agent is meningococcal polysaccharide vaccine (MPSV4, polysaccharide from the surface of the meningococcal bacteria), meningococcal conjugate vaccine (MCV4, polysaccharide chemically bonded to protein) and/or meningococcal serogroup B vaccine (MenB, which contains four proteins taken from group B *Neisseria meningitidis* bacteria).

15. A method for treating a condition comprising nasally administering the composition of claim 1 to a subject in need thereof, wherein:
   (a) the condition is hypogonadism, female sexual dysfunction, female arousal disorder, anorgasmia, or hypoactive sexual desire disorder, and the active agent is testosterone;
   (b) the condition is a brain injury, and the active agent is progesterone;
   (c) the condition is schizophrenia, and the active agent is aripiprazol, auetiapin, or paliperidon;
   (d) the condition is anxiety, and the active agent is duloxetine or dopamine;
   (e) the condition is multiple sclerosis, and the active agent is testosterone, glatirameracetat, interferon beta-1a, interferon beta-1b, fingolimod, natalizumab, or dimethylfumarat;

(f) the condition is Alzheimer's disease, and the active agent is pregnenolone, memantine, rivastigmin, or donepezil;

(g) the condition is depression, and the active agent is desvenlafaxine, duloxetine, or dopamine;

(h) the condition is insomnia, and the active agent is progesterone, eszopiclone or eszopiclone;

(i) the condition is attention deficit hyperactive disorder, and the active agent is tomoxetin, guanfacine, methylphenidate, lisdexamfetamine, or dopamine;

(j) the condition is traumatic brain injury, and the active agent progesterone or recombinant tissue plasminogen activator (rt-PA);

(k) the condition is a brain tumor, and the active agent is methotrexate, raltitrexed, 5-fluorouracil, telomerase inhibitor, or monoclonal antibodies;

(l) the condition is epilepsy, and the active agent is midazolam, lacosamide, levetiracetam, lamotrigine, or valproic acid;

(m) the condition is pain, and the active agent is oxycodone, pregabalin, buprenorphine, hydrocodone, or fentanyl; or (n) the condition is Parkinson's disease, and the active agent is safinamide, ropinirole, pramipexole, dopamine, L-DOPA, selegiline, cabergoline, or istradefylline.

16. A method for treating nasal congestion comprising administering the composition of claim 1 to a subject in need thereof, wherein the active agent comprises one or more of a corticosteroid, naphazoline, oxymetazoline, adrenaline, phenylephrine, nasal saline spray, brompheniramine, chlorpheniramine, clemastine, diphenhydramine, desloratadine, fexofenadine, loratadine, cromolyn, ectoin, and plant and anthroposophical substances.

17. A nasal pharmaceutical composition in the form of a gel adapted for nasal administration, comprising:
(a) a loaded porous excipient comprising mesoporous silica particles wherein active agent in an amorphous state is loaded onto surfaces of the mesoporous silica particles located inside pores of the mesoporous silica particles, wherein the composition comprises from about 0.5% to about 50% w/w of the mesoporous silica based on the weight of the composition;
(b) a lipophilic or partly lipophilic vehicle comprising an oil or mixture of oils in an amount from about 50% to about 90% w/w of the composition and a viscosity-regulating agent,
wherein the loaded porous excipient is dispersed in the vehicle, and
wherein the composition comprises a therapeutically effective amount of the active agent of from 10% w/w to 50% w/w based on the weight of the composition, in a volume suitable for nasal application, and wherein the composition has a viscosity of from about 2000 to about 6000 mPa·sec.

18. The nasal pharmaceutical composition of claim 17, comprising:
(a) from about 6% to about 50% w/w of the mesoporous silica, based on the weight of the composition;
(b) from 10% to about 40% w/w of the active agent, based on the weight of the composition;
(c) from about 50% to about 90% w/w of castor oil, based on the weight of the composition; and
(d) from about 0.5% to about 20% w/w of colloidal silicon dioxide, based on the weight of the composition.

19. The pharmaceutical composition of claim 17, wherein the active agent is testosterone or progesterone.

* * * * *